US009676832B2

(12) United States Patent
Austyn et al.

(10) Patent No.: US 9,676,832 B2
(45) Date of Patent: Jun. 13, 2017

(54) DENDRITIC CELL INHIBITORY PROTEINS FROM TICKS

(75) Inventors: Jonathan M. Austyn, Oxford (GB); Guido Paesen, Oxford (GB); Stephen Preston, Oxford (GB); Patricia Nuttal, Oxfordshire (GB)

(73) Assignees: Jon Austyn, Richmond (GB); Patricia Nuttall, Culham, Abingdon (GB)

( * ) Notice: Subject to any disclaimer, the term of this patent is extended or adjusted under 35 U.S.C. 154(b) by 291 days.

(21) Appl. No.: 13/636,469

(22) PCT Filed: Mar. 23, 2011

(86) PCT No.: PCT/GB2011/000419
§ 371 (c)(1),
(2), (4) Date: Feb. 22, 2013

(87) PCT Pub. No.: WO2011/117582
PCT Pub. Date: Sep. 29, 2011

(65) Prior Publication Data
US 2013/0156778 A1    Jun. 20, 2013

(30) Foreign Application Priority Data
Mar. 23, 2010  (GB) .................. 1004850.2

(51) Int. Cl.
| C07K 1/00 | (2006.01) |
| C07K 14/00 | (2006.01) |
| C12N 5/00 | (2006.01) |
| C12N 5/02 | (2006.01) |
| C07K 17/00 | (2006.01) |
| C07K 14/435 | (2006.01) |
| C07K 14/47 | (2006.01) |
| A61K 38/17 | (2006.01) |
| A61K 35/15 | (2015.01) |
| A61K 39/00 | (2006.01) |
| A61K 39/395 | (2006.01) |
| A61K 45/06 | (2006.01) |
| C07K 16/18 | (2006.01) |
| C12N 5/0784 | (2010.01) |

(52) U.S. Cl.
CPC ........ *C07K 14/43527* (2013.01); *A61K 35/15* (2013.01); *A61K 38/1767* (2013.01); *A61K 39/0003* (2013.01); *A61K 39/3955* (2013.01); *A61K 45/06* (2013.01); *C07K 14/4702* (2013.01); *C07K 16/18* (2013.01); *C12N 5/0639* (2013.01)

(58) Field of Classification Search
None
See application file for complete search history.

(56) References Cited

U.S. PATENT DOCUMENTS 6,617,312 B1   9/2003  Paesen et al.

2012/0070460 A1   3/2012  Austyn et al.

FOREIGN PATENT DOCUMENTS

| WO | 84/03564 A1 | 9/1984 |
| WO | 01/58941 A1 | 8/2001 |
| WO | 03/075953 A2 | 9/2003 |
| WO | 2006/077012 A2 | 7/2006 |
| WO | 2010/032008 A2 | 3/2010 |

OTHER PUBLICATIONS

Veillette et al., 1993, J. Biol. Chem. vol. 268: 17547-17553.*
Ganea et al., 2011, Clin. Lipidol. vol. 6: 277-291.*
Ganguly et al., 2013, Nat. Rev. Immunol. vol. 13: 566-577.*
Oliveira et al., 2008, Int. J. Parasit. vol. 38: 705-716.*
Juncadella et al., 2010, Biochem Biophys Res Commun. vol. 402: 105-109.*
Wang et al., 2001, J. Biol. Chem. vol. 276: 49213-49220.*
Whisstock et al.2003, Quart. Rev. Biophys. vol. 36: 307-340.*
Cambi et al., 2005, Cell. Micro. vol. 7: 481-488.*
Anguita, Juan et al., "Salp15, an *Ixodes scapularis* Salivary Protein, Inhibits CD4+ T Cell Activation," *Immunity* (Jun. 2002) 16:849-859.
Bergman, Douglas K. et al., "Isolation and Molecular Cloning of a Secreted Immunosuppressant Protein from *Dermacentor andersoni* Salivary Gland," *J. Parasitol.* (2000) 86(3):516-525.
Hannier, Sigrid et al., "Characterization of the B-cell inhibitory protein factor in *Ixodes ricinus* tick saliva: a potential role in enhanced *Borrelia burgdoferi* transmission," *Immunology* (2004) 113:401-408.
Hovius, J.W.R. et al., "Identification of Salp15 Homologues in *Ixodes ricinus* Ticks," *Vector-Borne and Zoonotic Diseases* (2007) 7(3):296-303.
Hovius, Joppe W. R. et al., "Salp15 Binding to DC-SIGN Inhibits Cytokine Expression by Impairing both Nucleosome Remodeling and mRNA Stabilization," *PLOS Pathogens* (Feb. 2008) 4(2) 0001-0014 (e31).
Lambson, B. et al., "Identification of candidate sialome components expressed in ixodid tick salivary glands using secretion signal complementation in mammalian cells," *Insect Molecular Biology* (2005) 14(4):403-414.
Leboulle, Gerard et al., "Characterization of a Novel Salivary Immunosuppressive Protein from *Ixodes ricinus* Ticks," *The Journal of Biological Chemistry* (Mar. 22, 2002) 277(12):10083-10089.
Mans, Ben J. et al., "The Major Tick Salivary Gland Proteins and Toxins from the Soft Tick, *Ornithodoros savignyi*, are part of the tick Lipocalin family: implications for the origins of tick toxicoses," *Mol. Biol. Evol.* (2003) 20:1158-1167.
Mans, Ben.J. et al., "Exon-intron structure of outlier tick lipocalins indicate a monophyletic origin within the larger lipocalin family," *Insect Biochem. Mol. Biol.* (2004) 34:585-594.

(Continued)

*Primary Examiner* — Amy Juedes
(74) *Attorney, Agent, or Firm* — Kilpatrick Townsend & Stockton LLP

(57) ABSTRACT

The present invention provides a dendritic cell modulatory protein which modulates, and preferably inhibits, the differentiation and/or maturation of mammalian dendritic cells. The invention also provides proteins comprising conserved motifs found in such proteins as well as pharmaceutical compositions comprising the dendritic cell modulatory protein and homologs and active fragments thereof, antibodies thereto and methods of treatment which utilize such proteins, homologs, fragments and antibodies.

4 Claims, 8 Drawing Sheets

(56) References Cited

OTHER PUBLICATIONS

Mans, Ben J. et al., "Tick histamine-binding proteins and related lipocalins: Potential as therapeutic agents," *Curr. Opin. Invest. Drugs* (2005) 6:1131-1135.

Oliveira, Carlo Jose F. et al., "Deconstructing Tick Saliva Non-Protein Molecules with Potent Immunomodulatory Properties," *The Journal of Biological Chemistry* (Apr. 1, 2011) 286(13):10960-10969.

Perrin-Cocon, Laure et al., "Secretory phospholipase $A_2$ induces dendritic cell maturation," *Eur. J. Immunol.* (2004) 34:2293-2302.

Preston, Stephen G. et al., "Novel Immunomodulators from Hard Ticks Selectively Reprogramme Human Dendritic Cell Responses," *PLOS Pathogens* (Jun. 2013) 9(6); 13 pages (e1003450).

Ribeiro, Jose M. C., "Blood-Feeding Arthropods: Live Syringes or Invertebrate Pharmacologists?" *Infectious Agents and Disease* (1995) 4:143-152.

Rolnikova, Terezia et al., "Modulation of human lymphocyte proliferation by salivary gland extracts of ixodid ticks (Acari: Ixodidae): effect of feeding stage and sex," *Folia Parasitoligica* (2003) 50:305-312.

Sa-Nunes, Anderson et al., "The Immunomodulatory Action of Sialostatin L on Dendritic Cells Reveals Its Potential to Interfere with Autoimmunity," *The Journal of Immunology* (2009) 182:7422-7429.

Yu, Da et al., "A tick B-cell inhibitory protein from salivary glands of the hard tick, *Hyalomma asiaticum asiaticum*," *Biochemical and Biophysical Research Communications* (2006) 343:585-590.

Cavassani et al., "Tick saliva inhibits differentiation, maturation and function of murine bone-marrow-derived dendritic cells," Immunology, 2005, vol. 114, No. 2, pp. 235-245.

Sa-Nunes et al., "Prostaglandin $E_2$ is a major inhibitor of dendritic cell maturation and function in *Ixodes scapularis* saliva," Journal of Immunology, 2007, vol. 179, pp. 1497-1505.

Skallova et al., "Tick saliva inhibits dendritic cell migration, maturation and function while promoting development of Th2 responses," Journal of Immunology, 2008, vol. 180, pp. 6186-6192.

International Search Report and Written Opinion, May 24, 2011, PCT Application No. PCT/GB2011/000419, 8 pages.

* cited by examiner

Figure 1

```
ggacactcacgttcactgaaactaacgaacgttgcgtgcgtaatatcgacctacagaggc
 G  H  S  R  S  L  K  L  T  N  V  A  C  V  I  S  T  Y  R  G
caaaaggatggatgggtcgagaggaatatgaattacgccttttctgttggaaaaccctgg
 Q  K  D  G  W  V  E  R  N  M  N  Y  A  F  S  V  G  K  P  W
cgaggacagtcctcaactattcatgtgcaatggcgaccatatgctgcattaatgaatgcg
 R  G  Q  S  S  T  I  H  V  Q  W  R  P  Y  A  A  L  M  N  A
aggacttcagatatcgtgagacatgatttgcaaacaaagccacagtacgtggtacgaaat
 R  T  S  D  I  V  R  H  D  L  Q  T  K  P  Q  Y  V  V  R  N
tacgatgataactctttggttctctcagacgtgaaagacgaatcgtcgccatgctcactc
 Y  D  D  N  S  L  V  L  S  D  V  K  D  E  S  S  P  C  S  L
tgggtgacaagaaagtatctggataatatcccagagacgacaaacagaacattttatcac
 W  V  T  R  K  Y  L  D  N  I  P  E  T  T  N  R  T  F  Y  H
caatgcccagaacctatctacactactatt
 Q  C  P  E  P  I  Y  T  T  I
```

Figure 2

```
                  10         20         30         40         50         60
                   |          |          |          |          |          |
japanin    MKVLRCLVCSFYIIVSLITTMTIGTPSMPAINTQTLYLAGHSSKLFERNVGCVKTRYLNQ
RaA        ---------------------------------------GHSRSLKLTNVACVISTYRGQ
                                                  ***  *   **.**  :  *  *

70         80         90        100        110        120
                   |          |          |          |          |          |
japanin    TGDWVTRSLIYVFTFDTEPWVTQAGAFQVKWEPYSPLLRVKASDYVRDNLGAKPDYFIRT
RaA        KDGWVERNMNYAFSVG-KPWRGQSSTIHVQWRPYAALMNARTSDIVRHDLQTKPQYVVRN
           ...** *.: *.*:..  :**   *:.:::*:*.**:..*:...:** **..* :**:*.:*.

130        140        150        160        170
                   |          |          |          |          |
japanin    YDNDFLLLSDLKEVRSTCSLWVTLKYVDRIPETINRTFYTICPDPVPVPFDERCYP
RaA        YDDNSLVLSDVKDESSPCSLWVTRKYLDNIPETTNRTFYHQCPEPIYTTI------
           **:: *:***:*: *.****** **:*.**** **** *:* ..:
```

Figure 3

```
ggatactcatctaaaatgaagataccaaacgttgtgtgcatcaactcaagatacttaagc
        G  Y  S  S  K  M  K  I  P  N  V  V  C  I  N  S  R  Y  L  S
agcgaaggcggctgggtgaagaggagtgtgaattacatgtttcccattgataaaccctgg
 S  E  G  G  W  V  K  R  S  V  N  Y  M  F  P  I  D  K  P  W
cgaggaaagtcctcaaccgttgaagtgaaatgggaaccatatgctgtattactgcatatg
 R  G  K  S  S  T  V  E  V  K  W  E  P  Y  A  V  L  L  H  M
aagacttcatatgatgtgagccgtgatttgcaaacaaagtcgcaatacgtagtacggaat
 K  T  S  Y  D  V  S  R  D  L  Q  T  K  S  Q  Y  V  V  R  N
tacgacgataactctttagttctctcagacctaaatgaagtatcatcatgctcactctgg
 Y  D  D  N  S  L  V  L  S  D  L  N  E  V  S  S  C  S  L  W
gtgacaaaggagtatctggataaaattccagagacgacaaaccgtacattttatcacctg
 V  T  K  E  Y  L  D  K  I  P  E  T  T  N  R  T  F  Y  H  L
tgcccagatcctgtctacacaccgtttgatgagaactgttatgtgaattaataaaagcag
 C  P  D  P  V  Y  T  P  F  D  E  N  C  Y  V  N  -
```

Figure 4

```
                    10         20         30         40         50         60
                    |          |          |          |          |          |
japanin    MKVLRCLVCSFYIIVSLITTMTIGTPSMPAINTQTLYLAGHSSKLFERNVGCVKTRYLNQ
RaB        ------------------------------------GYSSKMKIPNVVCINSRYLSS
                                               *:***:  ** *:::***..

70         80         90        100        110        120
                    |          |          |          |          |          |
japanin    TGDWVTRSLIYVFTFDTEPWVTQAGAFQVKWEPYSPLLRVKASDYVRDNLGAKPDYFIRT
RaB        EGGWVKRSVNYMFPID-KPWRGKSSTVEVKWEPYAVLLHMKTSYDVSRDLQTKSQYVVRN
           *.**.**: *:*.:* :** ::..:.:******: **::*:* * :* :*..:*.:*.

130        140        150        160        170
                    |          |          |          |          |
japanin    YDNDFLLLSDLKEVRSTCSLWVTLKYVDRIPETINRTFYTICPDPVPVPFDERCYP-
RaB        YDDNSLVLSDLNEV-SSCSLWVTKEYLDKIPETTNRTFYHLCPDPVYTPFDENCYVN
           **:: *:****:** :*:****** :*:*:**** *****  :***** .****.**
```

Figure 5

```
gcatattcatcgaagctgttctcatggaatgtggggtgcgtcaaaacaagacacttaagc
          A  Y  S  S  K  L  F  S  W  N  V  G  C  V  K  T  R  H  L  S
caagaaggagattgggtgacaaggagtctgatttacgtgtttaccttcgacaaaaaaccc
 Q  E  G  D  W  V  T  R  S  L  I  Y  V  F  T  F  D  K  K  P
tgggaaacaaaggccgatgcttttaaagtaaagtgggaaccatattctccactgctgcgt
 W  E  T  K  A  D  A  F  K  V  K  W  E  P  Y  S  P  L  L  R
gtgcaggcttcagattacgtgaaatataatttgagggcgaagccggaatatttatacgg
 V  Q  A  S  D  Y  V  K  Y  N  L  R  A  K  P  E  Y  F  I  R
acatacgacgacgactttttacttctatcagatgtgaaagagtcacgatcaccatgctcg
 T  Y  D  D  D  F  L  L  L  S  D  V  K  E  S  R  S  P  C  S
ctctgggtgacactaaagtacgtggagagaattccagagactataaacagaacatttat
 L  W  V  T  L  K  Y  V  E  R  I  P  E  T  I  N  R  T  F  Y
gcgaactgcccagatcctgtcaccgttccttttg
 A  N  C  P  D  P  V  T  V  P  F
```

Figure 6

```
                    10        20        30        40        50        60
                     |         |         |         |         |         |
japanin    MKVLRCLVCSFYIIVSLITTMTIGTPSMPAINTQTLYLAGHSSKLFBRNVGCVKTRYLNQ
Rs1        ---------------------------------------AYSSKLFSWNVGCVKTRHLSQ
                                                  .:*****. ********:*.*

70        80        90       100       110       120
                     |         |         |         |         |         |
japanin    TGDWVTRSLIYVFTFDTEPWVTQAGAFQVKWEPYSPLLRVKASDYVRDNLGAKPDYFIRT
Rs1        EGDWVTRSLIYVFTFDKKPWETKADAFKVKWEPYSPLLRVQASDYVKYNLRAKPEYFIRT
           **************** :** *:*.**:*************:*****: ** ***:*****

130       140       150       160       170
                     |         |         |         |         |
japanin    YDNDFLLLSDLKEVRSTCSLWVTLKYVDRIPETINRTFYTICPDPVPVPFDERCYP
Rs1        YDDDFLLLSDVKESRSPCSLWVTLKYVERIPETINRTFYANCPDPVTVPF------
           **.*******:** **.**********:*********: ***** .***.***
```

Figure 7

```
                10        20        30        40        50        60
                 |         |         |         |         |         |
japanin    MKVLRCLVCSFYIIVSLITTMTIGTPSMPAINTQTLYLAGHSSKLFERNVGCVKTRYLNQ
Rs1        --------------------------------------AYSSKLFSWNVGCVKTRHLSQ
RaA        --------------------------------------GHSRSLKLTNVACVISTYRGQ
RaB        --------------------------------------GYSSKMKIPNVVCINSRYLSS
                                                 .:*  .:   ** *:  :  ..

70        80        90       100       110       120
                 |         |         |         |         |         |
japanin    TGDWVTRSLIYVFTFDTEPWVTQAGAFQVKWEPYSPLLRVKASDYVRDNLGAKPDYFIRT
Rs1        EGDWVTRSLIYVFTFDKKPWETKADAFKVKWEPYSPLLRVQASDYVKYNLRAKPEYFIRT
RaA        KDGWVERNMNYAFSVG-KPWRGQSSTIHVQWRPYAALMNARTSDIVRHDLQTKPQYVVRN
RaB        EGGWVKRSVNYMFPID-KPWRGKSSTVEVKWEPYAVLLHMKTSYDVSRDLQTKSQYVVRN
            ..** *.: * *... :**  ::.:..*:*.**: *:. ::*  *  :* :*.:*.:*.

130       140       150       160       170
                 |         |         |         |         |
japanin    YDNDFLLLSDLKEVRSTCSLWVTLKYVDRIPETINRTFYTICPDPVPVPFDERCYP-
Rs1        YDDDFLLLSDVKESRSPCSLWVTLKYVERIPETINRTFYANCPDPVTVPF-------
RaA        YDDNSLVLSDVKDESSPCSLWVTRKYLDNIPETTNRTFYHQCPEPIYTTI-------
RaB        YDDNSLVLSDLNEVSS-CSLWVTKEYLDKIPETTNRTFYHLCPDPVYTPFDENCYVN
           **:: *:***::: * ****** :*::.**** ***** **:*:   ..:
```

Figure 8

```
                  10        20        30        40        50        60
                   |         |         |         |         |         |
japanin  MKVLRCLVCSFYIIVSLITTMTIGTPSMPAINTQTLYLAGHSSKLFERNVGCVKTRYLNQTG
Rs1      ----------------------------------------AYSSKLFSWNVGCVKTRHLSQEG
RaA      ----------------------------------------GHSRSLKLTNVACVISTYRGQKD
RaB      ----------------------------------------GYSSKMKIPNVVCINSRYLSSEG
Da       -----------MTYVETSNESPPFYELPANSTDTLYLVGHSVDLFRWMLTCVRTNYTSRQG
                                                 .:*  .:   : *: : : . .

72        82        92       102       112       122
                   |         |         |         |         |         |
japanin  DWVTRSLIYVFTFDT-EPWVTQAGAFQVKWEPYSPLLRVKA--SDYVRDNLGAKPDYFIRTY
Rs1      DWVTRSLIYVFTFDK-KPWETKADAFKVKWEPYSPLLRVQA--SDYVKYNLRAKPEYFIRTY
RaA      GWVERNMNYAFSVG--KPWRGQSSTIHVQWRPYAALMNART--SDIVRHDLQTKPQYVVRNY
RaB      GWVKRSVNYMFPID--KPWRGKSSTVEVKWEPYAVLLHMKT--SYDVSRDLQTKSQYVVRNY
Da       EVVNRTLIFNYSKEFNETPEEMSFPFQVTVPDVPIMFDLELNVTDSLVNYTGAQSTYHIIYY
                 * *.: : :.    :.    :...*   . ::  .  : :    ::. * : *

134       144       154       164       174       184
                   |         |         |         |         |         |
japanin  DNDFLLLSDLKEVRST---CSLWVTLKY--VDRIPETINRTFYTICPDPVPVPFDERCYP-
Rs1      DDDFLLLSDVKESRSP---CSLWVTLKY--VERIPETINRTFYANCPDPVTVPF------
RaA      DDNSLVLSDVKDESSP---CSLWVTRKY--LDNIPETTNRTFYHQCPEPIYTTI------
RaB      DDNSLVLSDLNEVSS----CSLWVTKEY--LDKIPETTNRTFYHLCPDPVYTPFDENCYVN
Da       NDESMVLGDKMPTVSERAICSLWVKENFTLEHQIPFMANLSFHTSCKNALYYGYLDTCSK-
         :::  ::*.*    *      *****. ::  ..**   *  *:  *  :.:
```

DENDRITIC CELL INHIBITORY PROTEINS FROM TICKS

This application is a U.S. National Phase under 35 USC 371 of PCT Application No. PCT/GB2011/000419 filed Mar. 23, 2011, which claims priority to GB Application No. 1004850.2, filed Mar. 23, 2010, the disclosures of which are incorporated by reference herein.

REFERENCE TO A "SEQUENCE LISTING" A TABLE, OR A COMPUTER PROGRAM LISTING APPENDIX SUBMITTED AS AN ASCII TEXT FILE

The Sequence Listing written in file 27914-24.TXT. created on Oct. 15, 2012, 77,824 bytes, machine format IBM-PC, MS-Windows operating system, is hereby incorporated by reference in its entirety for all purposes.

FIELD OF THE INVENTION

The present invention relates to dendritic cell (DC) modulatory proteins. In particular, the invention relates to proteins which modulate, and preferably inhibit, the differentiation and/or maturation of mammalian DCs and to the identification of motifs and features of such proteins which may be important for their structure and function. Such proteins can be isolated from arthropod saliva, and more specifically from tick saliva. The invention also relates to the use of such proteins in therapy, and specifically to the use of such proteins in treating autoimmune disorders, allergies, auto-inflammatory diseases and other immune-related sensitivities, also known as hypersensitivity diseases, transplant reactions such as transplant rejection and graft-versus-host disease, infectious diseases including those transmitted by ticks, cancers including haematological malignancies, and acute and chronic inflammatory diseases including inflammation associated with the aforementioned diseases.

BACKGROUND TO THE INVENTION

The mammalian, and particularly the human, immune system is comprised of two arms, the innate and the adaptive immune systems. The cells of the innate immune system recognise, and respond to, infectious agents in a generic manner. Although the innate immune system is a vital immediate barrier to infection, it does not confer specific, long-lasting protection against foreign entities, such as invading pathogens. In contrast, the cells of the adaptive immune system recognise specific foreign entities, and induce immunological memory to these specific entities in the host.

DCs interact with components of the innate immune system soon after infection by a pathogen and also form a central part of the mammalian adaptive immune response. DCs differentiate from precursor cells into immature DCs. Immature DCs are present throughout the body and, although other cells of the immune system also participate in this role, they are the major cell type responsible for initiation of adaptive immune responses, primarily through their capacity to trigger T cell activation.

Immature DCs constantly sample their surrounding environment for infectious agents such as viruses, bacteria and parasites, through pattern recognition receptors (PRRs) such as toll-like receptors (TLRs) which recognise specific chemical signals on the foreign entity, e.g. on a pathogen's surface. Once an entity such as a pathogen has been identified as foreign, the immature DC internalises the entity or fragments of it and degrades the protein and lipid antigens into peptides and glycopeptides or lipid fragments which are presented on the DC surface.

In response to foreign entity recognition, and/or other signals within the cell's environment (e.g. inflammatory cytokines), the immature DC undergoes several changes collectively termed 'maturation' and starts to develop into a mature DC. The maturing DC up-regulates expression of major histocompatability complex (MHC), and MHC-related molecules such as CD1, which bind the foreign entity-derived peptides and glycopeptides, and lipids or glycolipids, respectively, and allow them to be displayed on the DC surface. Simultaneously, the DC up-regulates expression of cell surface receptors known as costimulatory molecules including CD80, CD86 and CD40, which act as co-receptors for T lymphocyte activation. In addition, the DC begins to migrate to lymphoid tissues such as the lymph nodes and/or spleen, following chemotactic signals. Once in the lymphoid tissues, the DC activates T lymphocytes, by presenting them with the peptides and glycopeptides or lipid fragments derived from the foreign entity and delivering the appropriate co-stimulatory signals. Such activated T lymphocytes are responsible for propagating the adaptive immune response. The foreign entity may be a pathogen, an allergen, a transplantation antigen such as a major transplant antigen or a minor transplant antigen, a blood group antigen or, in the case of an autoimmune response, a self-antigen incorrectly identified by the body as foreign.

As well as having a role in triggering T cell activation by antigen presentation and costimulation, mature DCs are involved in T cell regulation, such as polarisation of helper T cells into Th1, Th2, Th17 or regulatory (Treg) cells, the activation of cytotoxic T cells, and modulation of T cell homing, e.g. into the skin or gut and other mucosal sites.

The central role played by DCs in the adaptive immune response has led to interest in the modulation of DC function for therapeutic purposes, and there have been indications from animal models that DC modulators may be useful in the treatment of autoimmune and other inflammatory diseases (Subklewe et al, Human Immunology, 2007, 68(3), 147-155). It has also been suggested that DC modulators may be useful in the treatment of cancer (Banchereau, J. et al, Ann N Y Acad Sci, 2003, 987, 180-187 and Figdor, C. G. et al, Nature medicine, 2004, 10 (5), 475-480).

Ticks and some other haematophagous arthropods attach to their hosts, including mammals such as humans, and feed for extended periods of time. The components that haematophagous arthropods deliver to the hosts, including components in saliva, can potentially induce host immune responses. Such responses may be deleterious to the arthropods and therefore the arthropods may need to suppress them. Given the central role of DCs in triggering immunity, it may be advantageous to the arthropods to produce proteins that inhibit their function.

Haematophagous arthropods, and particularly ticks, may inhibit the host's immune system by inoculating the host with a variety of anti-inflammatory and immunomodulatory components (Ribeiro et al, Infectious Agents and Disease, 1992, 4(3), 143-152).

Several immunomodulatory molecules have been identified in tick saliva, including a homologue of macrophage migration inhibitory factor (MIF) (Jaworski et al, Insect Molecular Biology, 2001, 10(4), 323-331), a homologue of leukocyte elastase inhibitor which is secreted by human macrophages, monocytes and neutrophils (Leboulle et al, The Journal of Biological Chemistry, 2002, 277(12), 10083-

10089), glycosylated protein p36, which is thought to suppress mitogen driven in vitro proliferation of murine spleen cells (Bergman et al, Journal of Parasitology, 2000, 86, 516-525), B cell inhibitory protein (BIP) (Hannier et al, Immunology, 2004, 113, 401-408), and B cell inhibitory factor (BIF) (Yu et al, Biochemical and Biophysical Research Communications, 2006, 343, 585-590).

Salp15 is a protein present in tick saliva which has been found to act on immature human DCs (Anguita et al, Immunity, 2002, 16, 849-859 and Hovius et al, Vector borne and Zoonotic diseases, 2007, 7(3), 296-302). However, assays involving the incubation of immature human DCs with Salp15 in the presence of an immune stimulus have shown that Salp15 does not inhibit the upregulation of costimulatory molecules (e.g. CD86). Salp15 does not therefore inhibit the maturation of human DCs.

Prostaglandin $E_2$ ($PGE_2$) is a non-protein molecule present in tick saliva that may modulate the activity of immature murine DCs, but has a minimal effect on maturation of these murine DCs (Sa-Nunes et al, The Journal of Immunology, 2007, 179, 1497-1505). $PGE_2$ is capable of enhancing the maturation of human DCs but there is no evidence that it can act to inhibit the differentiation and maturation of human DCs.

It has also been suggested that tick saliva and salivary gland extract (SGE) may possess the ability to modulate the differentiation and maturation of murine DCs (Cavassani et al, Immunology, 2005, 114, 235-245, and Skallova et al, Journal of Immunology, 2008, 180, 6186-6192).

A DC modulatory molecule has been isolated from the tick *Rhipicephalus appendiculatus*, and shown to modulate the differentiation and maturation of mammalian DCs (PCT/GB2009/002219). In particular, this molecule has been shown to alter the development of differentiation cultures by inhibiting upregulation of CD1a and downregulation of CD14, a signature of differentiation into DCs, and to inhibit T cell proliferation. This molecule is known as Japanin (SEQ ID NO: 8) and a limited number of homologues of Japanin have also been identified in other tick species (SEQ ID NOs: 10, 12, 14 and 16). It would be advantageous to identify further homologues of Japanin which act as DC modulators for therapeutic purposes. It would also be advantageous to identify the key motifs and features of such DC modulatory proteins which are responsible for their function.

SUMMARY OF THE INVENTION

Surprisingly, the inventors have now identified a number of further tick proteins which are homologous to Japanin, suggesting conserved function. Through the identification of these proteins, the inventors have been able to determine the motifs and features of the DC modulatory proteins which may be important for their function in DC modulation.

Accordingly, the present invention provides a DC modulatory protein, wherein said protein modulates, and preferably inhibits, mammalian DC differentiation and/or maturation, and preferably includes at least one of a number of conserved motifs and features that have been identified across a number of such proteins, and which are believed to be important to the function of such proteins.

Proteins of the Invention

In a first aspect, the present invention includes a DC modulatory protein, wherein said protein modulates DC differentiation and/or maturation and comprises:
i) the amino acid sequence of any one of SEQ ID NOs 2 (RaA), 4 (RaB) or 6 (Rs1);
ii) a homologue of a protein as defined in i) having at least 20% identity thereto; or
iii) an active fragment of a protein as defined in i) above or of a homologue as defined in ii) above.

In a further aspect, the present invention provides a dendritic cell (DC) modulatory protein, wherein said protein modulates mammalian DC differentiation and maturation and comprises:
i) the amino acid sequence of any one of a) SEQ ID NOs: 2, 25 or 28 (RaA); b) SEQ ID NOs: 4, 26 or 29 (RaB); or c) SEQ ID NOs: 6, 24 or 27 (Rs1);
ii) a homologue of a protein as defined in i) having at least 40% identity thereto; or
iii) an active fragment of a protein as defined in i) above or of a homologue as defined in ii) above.

In one embodiment, the protein of the invention may consist of the amino acid sequence of any one of a) SEQ ID NOs: 2, 25 or 28 (RaA); b) SEQ ID NOs: 4, 26 or 29 (RaB); or c) SEQ ID NOs: 6, 24 or 27 (Rs1). In one embodiment the protein of the invention may consist of the amino acid sequence of any one of SEQ ID NOs: 2, 4 or 6.

Activities of the Proteins of the Invention

The proteins of the invention "modulate", i.e. alter, or "inhibit", i.e. reduce, the differentiation and/or maturation of mammalian DCs. In some embodiments, the proteins of the invention "modulate", i.e. alter, or "inhibit", i.e. reduce, both the differentiation and maturation of mammalian DCs. In one embodiment, these may be human DCs. In a further embodiment, the proteins of the invention may additionally modulate or inhibit the differentiation and/or maturation of reptile and/or fish DCs as well as mammalian DCs. Suitable assays for assessing modulation or inhibition of DC differentiation and maturation are described below. It will be apparent to the skilled person that the markers described here for the assessment of modulation or inhibition of differentiation and maturation are provided by way of example only, and are not intended to be limiting. In one embodiment, the protein of the invention reduces both DC differentiation and maturation by at least 20% as measured, for example, by the assays discussed below. In further embodiments, the inhibition of DC differentiation and/or maturation may be 30%, 40%, 50%, 60%, 70%, 80%, 90% or more.

By "DC differentiation" is meant the development of a cell precursor, such as a bone marrow derived progenitor or a blood monocyte, into an immature DC. Modulation, for example inhibition, of DC differentiation can be assessed phenotypically and, ultimately functionally, using standard assays known in the art. These include the assessment of CD14 and CD1a expression, which are regulated during DC differentiation. Further methods for assessing the inhibition of DC differentiation will be known to a person skilled in the art.

Inhibition of phenotypic differentiation of precursors into immature DCs can be assessed using cellular markers whose expression is altered as the precursor cell differentiates into an immature DC. For example, monocytes are DC precursors which are CD14-positive and CD1a-negative. Immature DCs are CD14-low, and in some embodiments CD14-negative, and CD1a-positive. Hence, differentiation of monocytes into immature DCs may be detected by a decrease in CD14 and an increase in CD1a. Inhibition of differentiation of precursor cells into immature DCs by the proteins of the invention may be detected by the continued presence of precursor cells that are CD14-high, and in some embodiments CD14-positive, and CD1a-negative.

Functional differentiation of precursor cells and developed DCs can be assessed using any assay which distinguishes between precursor cells and differentiated DCs based on their activities. For example, unlike precursor cells, developed DCs, particularly after stimulation as described below, are capable of triggering T cell proliferation in an in vitro assay. Typical T cell proliferation assays include the allogeneic mixed leukocyte reaction (MLR) and oxidative mitogenesis.

By "DC maturation" is meant the process which occurs after a precursor cell has differentiated into an immature DC. Specifically, this term relates to the changes which occur when a differentiated, immature DC encounters a stimulus, and is converted into a mature DC. The stimulus may be a component of an infectious agent such as a pathogen, which is sensed via PRR such as TLR, certain cytokines which act through cytokine receptors, and/or specialised cell surface molecules of other cell types such as CD154 of activated T cells. The changes associated with maturation of immature DCs typically include the up-regulation of expression of costimulatory molecules e.g. CD80 and CD86 and the presentation of antigens from the pathogenic-derived component on the DC's surface, typically as peptide-MHC and lipid-CD1 complexes. Maturation of immature DCs may also be associated with migration of the DC to the secondary lymphoid tissues.

The proteins of the invention may act to modulate or inhibit any of these changes associated with maturation of immature DCs. The ability of the molecules of the invention to inhibit immature DC maturation may thus be assessed by their ability to decrease the expression of CD86 and/or CD80 and/or MHC molecules. The ability of the proteins of the invention to inhibit immature DC maturation may be assessed by their ability to decrease the expression and/or the secretion of TNFα. The ability of the proteins of the invention to modulate DC maturation may be assessed by their ability to increase levels of B7 homolog 1 (B7-H1 or C274) expression. The ability of the proteins of the invention to inhibit DC maturation may optionally be assessed following poly(I:C), LPS or IFNγ stimulation. The ability of the proteins of the invention to inhibit DC maturation may optionally be assessed following CD40L, IFNα, or a TLR7 or TLR8 ligand (e.g. CL097) stimulation. Further methods for assessing the inhibition of immature DC maturation will be known to a person skilled in the art.

As described above, the proteins of the invention act to modulate, and preferably inhibit, differentiation of precursor cells into immature DCs and to modulate, and preferably inhibit, the subsequent maturation of immature DCs into mature DCs. Such modulation or inhibition of both DC differentiation and maturation is likely to have downstream modulatory effects on the immune system as a whole, as described in more detail below.

Prior to activation by an antigen presenting cell, T lymphocytes are referred to as "naïve". Each T lymphocyte is specific for a particular antigen, and can only be activated by a 'specialised' antigen presenting cell, such as a DC, which is presenting this cognate antigen. Conventional T lymphocytes recognise the antigen-MHC complex through the T cell receptor (TCR), which is a heterodimeric structure, comprising α and β chains. However, signalling through the TCR, in the absence of costimulation, results in a state of antigen-unresponsiveness or anergy, or abortive activation and cell death. Therefore, the costimulatory molecules, which are upregulated on the surface of immature DCs during the maturation process, and are recognised by receptor molecules such as CD28 (in the case of CD80 and CD86) or CD154 (for CD40) on the T lymphocyte's surface, are vital for the activation of T lymphocytes.

In one aspect of the invention, the inhibition of DC differentiation and/or maturation afforded by the proteins of the invention, results in a decrease in T lymphocyte activation. By "T lymphocyte activation" is meant activation of helper T cells, including Th1, Th2, Th17 or Treg cells, and optionally the activation of cytotoxic T cells which is often dependent on prior activation of helper T cells.

A decrease in T cell activation may be assessed by methods known in the art. By way of example, and not limitation, T cell activation may be assessed by in vitro assays of cytokine secretion [e.g. interleukin (IL)-2 production] or T cell proliferation triggered by DC (e.g. allogeneic MLR or oxidative mitogenesis) or by in vivo assays of T cell responses to model antigens (e.g. ovalbumin) in normal or transgenic animals using similar assays of T cells isolated ex vivo before and after antigen re-stimulation.

In one embodiment, the proteins of the invention will reduce T lymphocyte activation by at least about 20% compared to a standard assay in the absence of a DC differentiation and/or maturation inhibiting protein. In further embodiments, the inhibition of DC differentiation and maturation may reduce T lymphocyte activation by at least about 30%, 40%, 50%, 60%, 70%, 80%, 90% or more.

In one aspect of the invention, the modulation or inhibition of DC differentiation and/or maturation afforded by the proteins of the invention, results in a modulation in T lymphocyte regulation. In particular, the proteins of the invention may modulate the polarisation of T lymphocytes into Th1 versus Th2 versus Th17 versus regulatory T (Treg) or follicular helper T (Thf) cells. Modulation of T lymphocyte polarisation by the proteins of the invention may be assessed by measuring T-lymphocyte-derived cytokines typically associated with different types of CD4 and CD8 T lymphocytes in in vitro assays. For Th1 cells, these include IFN-γ; for Th2 cells, IL-4, IL-5, and IL-13; for Th17 cells, IL-17; and for Treg cells, IL-10 and TGFβ. The respective types of CD4 cell can also be assayed by measuring expression of T-bet, GATA-3, ROR-γ-t or ROR-γ-c and FoxP3 respectively, or by measuring expression of Bcl6 for Thf cells. Alternatively, the phenotype of the different cells can be assessed phenotypically, e.g. by assessing the chemokine receptors and other phenotypic markers that they express.

T lymphocytes are one of the major facilitators of the mammalian immune response. Therefore, a reduction in the activation of T lymphocytes by the proteins of the invention or a change in the polarisation of such T lymphocytes, as described above, will result in an overall modulation of the immune response and in particular in changes in the levels of cytokines associated with the immune response. For example, the proteins of the invention may have a generally immunosuppressant effect.

It will be apparent to a person skilled in the art that a modulation in the immune response, such as an immunosuppressant effect, can be measured using any one of a variety of methods known in the art. A decrease in, or modulation of, the overall immune response can be measured by looking for a reduction in the levels of pro-inflammatory cytokines produced most rapidly in response to TLR stimulation, e.g. interleukin-1 and tumour necrosis factor α (TNFα), interferon-α, interferon β, or cytokines such as IL-6 or IL-12 typically produced at intermediate times after infection. The proteins of the invention may also lead to an increase in the level of anti-inflammatory cytokines e.g. IL-10 or TGF-β.

In one embodiment, the proteins of the invention will reduce the levels of pro-inflammatory cytokines or increase the levels of anti-inflammatory cytokines by at least about 20% compared to a standard assay in the absence of a DC differentiation and/or maturation inhibiting protein. In further embodiments, the inhibition of DC differentiation and/or maturation may reduce the levels of pro-inflammatory cytokines or increase the levels of anti-inflammatory cytokines by at least about 30%, 40%, 50%, 60%, 70%, 80%, 90% or more.

An immunosuppressant effect may also be assessed by a variety of other methods, for example a localised reduction in inflammation or a reduction in the size or activity of generated antigen-specific T and B cell pools.

Arthropods from which the Proteins of the Invention May be Isolated

The proteins of the invention may be isolated from an arthropod. An "arthropod" is defined as an animal belonging to the phylum Arthropoda, and includes insects, crustaceans and arachnids. Arthropods are characterised by a segmented body and a hard exoskeleton made of chitin.

Within one aspect of the invention, the proteins of the invention may be isolated from a haematophagous arthropod. The term "haematophagous arthropod" includes all arthropods that take a blood meal from a suitable host. This includes ticks, mites, and insects such as lice, fleas and mosquitoes. They are commonly known as blood feeding arthropods, and these two terms will be used interchangeably throughout this specification.

Within a further aspect of the invention, the isolated haematophagous arthropod may be a tick. The term "tick" is the common name given to small arachnids in the superfamily Ixodoidea, which is included within the haematophagous arthropods. Ticks are ectoparasites, and live on the blood of mammals, birds, and reptiles. Ticks may also live on the blood of amphibians.

There are approximately 900 species of tick, which are found throughout the world. Different tick species are characterised by their preferential habitat and by their geographical distribution. Most tick species can feed on a variety of host species, including humans. As discussed above, arthropods, and particularly ticks may inhibit the host's immune system by inoculating the host with a variety of anti-inflammatory and immunomodulatory components.

The DC modulatory proteins of the present invention may be isolated from any known tick species, including species within the groups Ixodinae, Bothriocrotoninae, Amblyomminae, Haemaphysalinae, Rhipicephalinae, Hyalomminae, Nuttalliellidae, Argasinae, Otobinae, Antricolinae, Nothoaspinae and Ornithodorinae, for example, any one of the following tick species: *Rhipicephalus appendiculatus, Rhipicephalus sanguineus, Rhipicephalus bursa, Amblyomma americanum, Amblyomma cajennense, Amblyomma hebraeum, Amblyomma variegatum, Rhipicephalus (Boophilus) microplus, Rhipicephalus (Boophilus) annulatus, Rhipicephalus (Boophilus) decoloratus, Dermacentor reticulatus, Dermacentor andersoni, Dermacentor marginatus, Dermacentor variabilis, Haemaphysalis inermis, Haemaphysalis leachii, Haemaphysalis punctata, Hyalomma anatolicum anatolicum, Hyalomma dromedarii, Hyalomma marginatum marginatum, Ixodes ricinus, Ixodes persulcatus, Ixodes scapularis, Ixodes hexagonus, Argas persicus, Argas reflexus, Ornithodoros erraticus, Ornithodoros moubata moubata, Ornithodoros moubata porcinus,* and *Ornithodoros savignyi.*

Homologues

The present invention includes homologues and active fragments of proteins having the amino acid sequence of any one of a) SEQ ID NOs: 2, 25 or 28 (RaA); b) SEQ ID NOs: 4, 26 or 29 (RaB); or c) SEQ ID NOs: 6, 24 or 27 (Rs1). The present invention includes homologues and active fragments of proteins having the amino acid sequence of any one of SEQ ID NOs: 2, 4 or 6.

The term "homologue" is intended to include reference to paralogues and orthologues of the proteins of the invention disclosed in SEQ ID NOs: 2, 4 and 6, or SEQ ID NOs: 24, 25, 26, 27, 28 or 29 that retain the ability to modulate, and preferably inhibit, the differentiation and/or maturation of DCs. Homologues may possess the ability to modulate, and preferably inhibit, the differentiation and/or maturation of DCs, resulting in a decrease in T lymphocyte activation or modulation of T lymphocyte polarisation, as described above.

In one embodiment, the invention includes a protein comprising or consisting of an amino acid sequence having at least 20% sequence identity to any one of SEQ ID NO: 2, 25 or 28. In other embodiments the invention includes proteins comprising or consisting of an amino acid sequence having at least 40%, 50%, 60%, 70%, 80%, 81%, 82%, 85%, 90%, 95%, 98%, 99% or more to any one of SEQ ID NO: 2, 25 or 28. In one embodiment, the invention includes a protein comprising or consisting of an amino acid sequence having at least 20% sequence identity to SEQ ID NO: 2. In other embodiments the invention includes proteins comprising or consisting of an amino acid sequence having at least 40%, 47%, 48%, 50%, 60%, 70%, 80%, 85%, 90%, 95%, 98%, 99% or more to SEQ ID NO: 2. Percentage identity, as referred to herein, is as determined using clustalW with the following options: gap extension penalty=0.1; gap opening penalty=10.0; hydrophilic residues=G, P, S, N, D, Q, E, R or K; matrix=gonnet. Alternatively, percentage identity values can be determined using BLAST version 2.1.3 using the default parameters specified by the NCBI (the National Centre for Biotechnology Information; http://www.ncbi.nlm.nih.gov/) [Blosum 62 matrix; gap open penalty=11 and gap extension penalty=1].

In one embodiment, the invention includes a protein comprising or consisting of an amino acid sequence having at least 20% sequence identity to SEQ ID NO: 4, 26 or 29. In other embodiments the invention includes proteins comprising or consisting of an amino acid sequence having at least 40%, 50%, 60%, 70%, 80%, 81%, 82%, 85%, 90%, 95%, 98%, 99% or more to SEQ ID NO: 4, 26 or 29.

In one embodiment, the invention includes a protein comprising or consisting of an amino acid sequence having at least 20% sequence identity to SEQ ID NO: 4. In other embodiments the invention includes proteins comprising or consisting of an amino acid sequence having at least 40%, 50%, 53%, 54%, 60%, 70%, 80%, 85%, 90%, 95%, 98%, 99% or more to SEQ ID NO: 4.

In one embodiment, the invention includes a protein comprising or consisting of an amino acid sequence having at least 20% sequence identity to SEQ ID NOs: 6, 24 or 27. In other embodiments the invention includes proteins comprising or consisting of an amino acid sequence having at least 40%, 50%, 60%, 70%, 80%, 81%, 82%, 85%, 90%, 95%, 98%, 99% or more to SEQ ID NOs: 6, 24 or 27.

In one embodiment, the invention includes a protein comprising or consisting of an amino acid sequence having at least 20% sequence identity to SEQ ID NO: 6. In other embodiments the invention includes proteins comprising or consisting of an amino acid sequence having at least 40%, 50%, 60%, 70%, 80%, 81%, 82%, 85%, 90%, 95%, 98%, 99% or more to SEQ ID NO: 6.

Homologues of the proteins of the invention also include mutants containing amino acid substitutions, insertions or deletions from the sequences of SEQ ID NOs: 2, 4, 6, 24, 25, 26, 27, 28 or 29 and fragments thereof, provided that the ability to modulate, and preferably inhibit, the differentiation and/or maturation of DCs is retained. Mutants may possess the ability to modulate, and preferably inhibit, the differentiation and/or maturation of DCs, resulting in a decrease in T lymphocyte activation or modulation of T lymphocyte polarisation, as described above. In a further embodiment, mutants may possess the ability to modulate, and preferably inhibit, the differentiation and/or maturation of DCs, resulting in an inhibition of the immune response, as described above.

Mutants thus include proteins containing conservative amino acid substitutions that do not affect the function or activity of the protein in an adverse manner. This term is also intended to include natural biological variants (e.g. allelic variants or geographical variations within the species from which the isolated arthropod proteins of the invention are derived). Mutants with improved activity in the modulation or inhibition of the differentiation and/or maturation of DCs compared to that of the wild type protein sequence may also be designed through the systematic or directed mutation of specific residues in the protein sequence.

Homologues may be derived from tick species including but not limited to *Rhipicephalus appendiculatus*, including *Rhipicephalus sanguineus, Rhipicephalus bursa, Amblyomma americanum, Amblyomma cajennense, Amblyomma hebraeum, Ambylomma variegatum, Rhicephalus (Boophilus) microplus, Rhicephalus (Boophilus) annulatus, Rhicephalus (Boophilus) decoloratus, Dermacentor reticulatus, Dermacentor andersoni, Dermacentor marginatus, Dermacentor variabilis, Haemaphysalis inermis, Haemaphysalis leachii, Haemaphysalis punctata, Hyalomma anatolicum anatolicum, Hyalomma dromedarii, Hyalomma marginatum marginatum, Ixodes ricinus, Ixodes persulcatus, Ixodes scapularis, Ixodes hexagonus, Argas persicus, Argas reflexus, Ornithodoros erraticus, Ornithodoros moubata moubata, Ornithodoros moubata porcinus*, and *Ornithodoros savignyi*. Homologues may also be derived from mosquito species, including those of the *Culex, Anopheles* and *Aedes* genera, particularly *Culex quinquefasciatus, Aedes aegypti* and *Anopheles gambiae*; flea species, such as *Ctenocephalides felts* (the cat flea); horseflies; sandflies; blackflies; tsetse flies; lice; and mites.

In general, homologues may be derived from any known tick species, for example those within the groups Ixodinae, Bothriocrotoninae, Amblyomminae, Haemaphysalinae, Rhipicephalinae (including Hyalomminae), Nuttalliellidae, Argasinae, Otobinae, Antricolinae, and Ornithodorinae.

Methods for the identification of homologues of the proteins of the invention will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database, the EMBL database, the DDBJ database, the SWISS-PROT protein database, PIR, TrEMBL, the TIGR databases, the NRL-3D database, the Protein Data Bank, the NRDB database, the OWL database and the secondary databases PROSITE, PRINTS, Profiles, Pfam, Identify and Blocks. Examples of commercially-available databases or private databases include PathoGenome (Genome Therapeutics Inc.) and PathoSeq (Incyte Pharmaceuticals Inc.).

Although the inventors do not wish to be bound by theory, it is postulated that the amino acid sequences of SEQ ID NOs: 2, 4 and 6 may not be full-length sequences. The invention thus provides that further amino acids may be present at the N-terminus and/or the C-terminus of proteins comprising the amino acid sequences of SEQ ID NOs: 2, 4 or 6. In one embodiment the invention includes proteins comprising the addition of 1, 2, 3, 4, 5, 6, 7, 8, 9, 10, 15, 20, 25, 30, 35, 40, 45, 50, 60, 70, 80, 90, 100, 150 or 200 amino acid at the N-terminus and/or the C-terminus of the sequences of any one of SEQ ID NOs: 2, 4 or 6.

The amino acid sequences of SEQ ID NOs: 24, 25 and 26 are believed to represent full-length proteins. Amino acid sequences of SEQ ID NO: 27, 28 and 29 are predicted to represent the mature proteins (with which is meant the proteins without the signal sequences typical for secretion products). The invention also provides that further amino acids may be present at the N-terminus and/or C-terminus of proteins comprising the amino acid sequences of a) SEQ ID NOs: 2, 25 or 28 (RaA); b) SEQ ID NOs: 4, 26 or 29 (RaB); or c) SEQ ID NOs: 6, 24 or 27 (Rs1). In one embodiment the invention includes proteins comprising the addition of 1, 2, 3, 4, 5, 6, 7, 8, 9, 10, 15, 20, 25, 30, 35, 40, 45, 50, 60, 70, 80, 90, 100, 150 or 200 amino acid at the N-terminus and/or the C-terminus of the sequences of any one of a) SEQ ID NOs: 2, 25 or 28 (RaA); b) SEQ ID NOs: 4, 26 or 29 (RaB); or c) SEQ ID NOs: 6, 24 or 27 (Rs1).

In one embodiment the invention also includes functional equivalents of the proteins of the invention. The term "functional equivalent" is used herein to describe any molecule possessing the ability to modulate, and preferably inhibit, the differentiation and/or maturation of DCs in a manner corresponding to proteins of the invention. This includes synthetically produced proteins, synthetic variants of the protein, protein molecules of a different sequence which confer corresponding activity, naturally occurring non-protein molecules with corresponding activity, and synthetic non-protein molecules with corresponding activity. It also includes semi-synthetically produced proteins, semi-synthetic variants of the protein and semi-synthetic non-protein molecules with corresponding activity. Also included are antibodies that mimic the ability of proteins of the invention to modulate, and preferably inhibit, the differentiation and/or maturation of DCs.

In particular, synthetic molecules that are designed to mimic the tertiary structure or active site(s) of the proteins of the invention are considered to be functional equivalents. In one embodiment, functional equivalents possess the ability to modulate, and preferably inhibit, the differentiation and/or maturation of DCs, resulting in a decrease in T lymphocyte activation or modulation of T lymphocyte polarisation, as described above. In a further embodiment, functional equivalents possess the ability to modulate, and preferably inhibit, the differentiation and/or maturation of DCs, resulting in an inhibition of the immune response, as described above.

In one embodiment, homologues may retain one or more of the conserved motifs and features of the DC modulatory proteins of SEQ ID NOs: 2, 4 and 6 or SEQ ID NOs: 24, 25, 26, 27, 28 or 29. As described below, these include a conserved glycosylation site containing sequence, cysteine distribution pattern, CXXW (SEQ ID NO:33) motif, lipid binding ability, and receptor binding ability.

In certain embodiments, the proteins of the invention or homologues thereof do not have the amino acid sequence of any one of SEQ ID NOs: 8, 10, 12, 14, or 16. These sequences correspond to SEQ ID NOs: 2, 4, 6, 8 and 10 of PCT/GB2009/002219, respectively.

Fragments

The present invention also provides "active fragments" of the proteins of the invention and of homologues of these sequences. Included within this definition are any fragments which retain the ability to modulate or inhibit mammalian DC differentiation and/or modulation.

Included as such fragments are not only fragments of amino acid sequences of SEQ ID NOs: 2, 4 and 6 or SEQ ID NOs: 24, 25, 26, 27, 28 or 29, but also fragments of homologues of this protein, as described above. Such fragments of homologues will typically possess greater than 20% identity with fragments of the amino acid sequences of any one of SEQ ID NOs: 2, 4 or 6.

Said fragments of homologues will typically possess greater than 20% identity with fragments of the amino acid sequence of any one of i) SEQ ID NOs: 2, 25 or 28, ii) SEQ ID NOs: 4, 26 or 29 or iii) SEQ ID NOs: 6, 24 or 27.

In certain embodiments fragments of homologues will display degrees of identity of greater than 30%, 40%, 47%, 48%, 50%, 52%, 53% 60%, 70%, 80%, 81%, 82%, 90%, 95%, 98% or 99%, respectively with fragments of the isolated arthropod proteins of SEQ ID NOs: 2, 4 or 6.

In further embodiments fragments of homologues will display degrees of identity of greater than 30%, 40%, 47%, 48%, 50%, 52%, 53% 60%, 70%, 80%, 81%, 82%, 90%, 95%, 98% or 99%, respectively with fragments of the isolated arthropod proteins of any one of i) SEQ ID NOs: 2, 25 or 28, ii) SEQ ID NOs: 4, 26 or 29 or iii) SEQ ID NOs: 6, 24 or 27.

Protein fragments of the invention are preferably active fragments of SEQ ID NOs: 2, 4 or 6 or SEQ ID NOs: 24, 25, 26, 26, 28 or 29 and homologues thereof as described above. These fragments preferably modulate, and more preferably inhibit, the differentiation and/or maturation of DCs. In one embodiment, fragments of the proteins of the invention modulate, and preferably inhibit, the differentiation and/or maturation of DCs resulting in a decrease in T lymphocyte activation or modulation of T lymphocyte polarisation, as described above. In a further embodiment, fragments of the proteins of the invention modulate, and preferably inhibit, the differentiation and/or maturation of DCs, resulting in an inhibition of the immune response, as described above. Fragments with improved activity in modulating or inhibiting the differentiation and/or maturation of DCs may, of course, be rationally designed by the systematic mutation or fragmentation of the amino acid sequences of any one of SEQ ID NOs: 2, 4 or 6 or SEQ ID NOs: 24, 25, 26, 27, 28 or 29.

In one embodiment, fragments of the proteins of the invention or homologues thereof may be at least 5, 6, 7, 8, 9, 10, 15, 20, 25, 30, 40, 50, 60, 70, 80, 90, 100 or more amino acids in length. Fragments of the invention may comprise at least 5, 6, 7, 8, 9, 10, 15, 20, 25, 30, 40, 50, 60, 70, 80, 90, 100 or more consecutive amino acids from the amino acid sequence of any one of SEQ ID NOs: 2, 4 or 6 or homologues thereof.

Fragments of the invention may comprise at least 5, 6, 7, 8, 9, 10, 15, 20, 25, 30, 40, 50, 60, 70, 80, 90, 100 or more consecutive amino acids from the amino acid sequence of any one of i) SEQ ID NOs: 2, 25 or 28, ii) SEQ ID NOs: 4, 26 or 29 or iii) SEQ ID NOs: 6, 24 or 27, or homologues thereof.

Protein fragments of the invention may retain one or more of the conserved motifs and features of the DC modulatory proteins of SEQ ID NOs: 2, 4, 6, 24, 25, 26, 27, 28 and 29. In one embodiment, protein fragments of the invention may retain one or more of the conserved motifs and features of the DC modulatory proteins of SEQ ID NOs: 2, 4 and 6. As described below, these include a conserved glycosylation site containing sequence, cysteine distribution pattern, CXXW (SEQ ID NO:33) motif, lipid binding ability, and receptor binding ability.

Glycosylation

The inventors have discovered that DC modulatory proteins are glycosylated at one or more positions. Therefore, in one aspect the proteins of the invention may be glycosylated at one or more positions. In one embodiment, the protein may be glycosylated at one, two, three or more positions. The proteins of the invention are preferably N-glycosylated, (i.e. a polysaccharide is attached to an asparagine amino acid residue) although the protein may also be O-glycosylated (i.e. N-acetyl-galactosamine is attached to a serine or threonine residue) at one or more positions. In one embodiment the carbohydrate moiety may include one or more mannose or fucose or galactose units.

The inventors have also discovered that DC modulatory proteins of the inventions have a consensus sequence around the glycosylation site. This consensus sequence has the amino acid residue to be glycosylated at a conserved position. In one embodiment the amino acid residue to be glycosylated is an asparagine residue (in the case of N-glycosylation) or a serine or threonine residue (in the case of O-glycosylation). The proteins of the invention have the amino acid residue asparagine at amino acid position 115 of RaA (SEQ ID NO: 2), 113 of RaB (SEQ ID NO: 4) and 116 of Rs1 (SEQ ID NO: 6). Further, the proteins of the invention have the amino acid residue asparagine at amino acid position 154 of full length RaA protein (SEQ ID NO: 25), 153 of full length RaB protein (SEQ ID NO:26) or 155 of full length Rs1 protein (SEQ ID NO:24). These positions correspond to residue 155 of the amino acid sequence of Japanin (SEQ ID NO: 8). Therefore, in one embodiment the proteins of the invention have a conserved asparagine residue at a residue corresponding to any one of amino acid positions 110-120 of the sequences of any one of SEQ ID NOs: 2, 4 or 6. In another embodiment the proteins of the invention have a conserved asparagine residue at a residue corresponding to amino acid position 115 of RaA (SEQ ID NO: 2), 113 of RaB (SEQ ID NO: 4) or 116 of Rs1 (SEQ ID NO: 6). In another embodiment the proteins of the invention have a conserved asparagine residue at the amino acid position which corresponds to amino acid position 155 of the amino acid sequence of Japanin (SEQ ID NO: 8).

In one embodiment the protein of the invention or homologue or fragment thereof comprises the glycosylation site containing sequence N-Z-(S/T)-(X)$_{3-5}$-C(SEQ ID NO:50), wherein X is any amino acid and Z is any amino acid except proline.

In another embodiment the protein of the invention or homologue or fragment thereof comprises the glycosylation site containing sequence (X)$_{12-16}$-N-Z-(S/T)-(X)$_{3-5}$-C(SEQ ID NO:51), wherein X is any amino acid and Z is any amino acid except proline.

In another embodiment the protein of the invention or homologue or fragment thereof comprises the glycosylation site containing sequence W-$(X)_{12-16}$-N-Z-(S/T)-$(X)_{3-5}$-C (SEQ ID NO:52), wherein X is any amino acid and Z is any amino acid except proline.

In another embodiment the protein of the invention or homologue or fragment thereof comprises the glycosylation site containing sequence C-$(X)_2$—W-$(X)_{12-16}$-N-Z-(S/T)-$(X)_{3-5}$-C (SEQ ID NO:53), wherein X is any amino acid and Z is any amino acid except proline.

In another embodiment the protein of the invention or homologue or fragment thereof comprises the glycosylation site containing sequence C-$(X)_2$—W-$(X)_{12-16}$-N-Z-(S/T)-(F/Y)-$(X)_{2-4}$-C (SEQ ID NO:54), wherein X is any amino acid and Z is any amino acid except proline.

In another embodiment the protein of the invention or homologue or fragment thereof comprises the glycosylation site containing sequence C-$(X)_2$—W-$(X)_{7-11}$-(I/L)-P-$(X)_3$—N-Z-(S/T)-$(X)_{3-5}$-C(SEQ ID NO:55), and wherein X is any amino acid and Z is any amino acid except proline.

In another embodiment the protein of the invention or homologue or fragment thereof comprises the glycosylation site containing sequence C-$(X)_2$—W-$(X)_{7-11}$-(I/L)-P-$(X)_3$—N-Z-(S/T)-(F/Y)-$(X)_{2-4}$-C(SEQ ID NO:56), wherein X is any amino acid and Z is any amino acid except proline.

In another embodiment the protein of the invention or homologue or fragment thereof comprises the glycosylation site containing sequence C-$(X)_2$-W-$(X)_{13-15}$-N-Z-(S/T)-$(X)_4$-C (SEQ ID NO:57), wherein X is any amino acid and Z is any amino acid except proline.

Proteins of the invention may be glycosylated naturally. This may particularly be the case if the protein is produced naturally and isolated, or if the protein is produced recombinantly in a host cell which mirrors the glycosylation pattern of the organism in which the protein is naturally produced. Alternatively, it may be necessary to artificially glycosylate the protein of the invention. This may particularly be the case if the protein is chemically synthesised, or if the protein is produced recombinantly in an organism which does not mirror the natural glycosylation pattern of the protein. Further, additional glycosylation may occur in order to alter or improve the properties of the protein.

Without wishing to be bound by theory, the inventors hypothesise that it is the carbohydrate moiety of the proteins of the invention which is involved in the binding of DC modulatory proteins to their receptors. This is discussed in more detail below in the section entitled "receptor binding".

As discussed above, the present invention includes homologues and fragments of the amino acid sequences of SEQ ID NOs: 2, 4 and 6 or of SEQ ID NOs 24, 25, 26, 27, 28 or 29. Homologues or fragments of the invention may retain the glycosylation site containing sequence of the full length sequences of SEQ ID NOs: 2, 4, 6, 24, 25, 26, 27, 28 or 29. In certain embodiments the homologues or fragments may retain the glycosylation site containing sequence of the full length sequences of SEQ ID NOs: 2, 4 and 6. In other certain embodiments the homologues and fragments may retain one or more of the glycosylation site containing sequences described above.

Cysteine Distribution Pattern

The sequence homology between the proteins of the inventions and the previously identified DC modulatory protein Japanin indicates that, like Japanin, the proteins of the invention are lipocalins, or lipocalin-like molecules. The lipocalins are a family of proteins which share a similar structural fold. The characteristic lipocalin fold is an eight-stranded anti-parallel beta-barrel, which forms an internal cavity that in most cases acts as a ligand binding site. The lipocalins, in general, contain cysteine residues at spaced locations. At least some of the cysteine residues, in general, form internal disulphide bonds, which may stabilise the lipocalin fold.

The inventors have discovered that the DC modulatory proteins of the invention possess a conserved cysteine distribution pattern. This cysteine distribution pattern is believed to be required in order to form the specific lipocalin fold of the DC modulatory proteins of the present invention, and is configured to allow the binding of a lipid molecule such as cholesterol to the proteins, as discussed in more detail below. The cysteine distribution pattern may also be required in order to stabilise the specific lipocalin fold.

In one embodiment, the proteins of the invention comprise the cysteine distribution pattern C-$(X)_{82-92}$-C-$(X)_{22-26}$-C-$N_{10-12}$-C(SEQ ID NO:58), wherein X is any amino acid.

In one embodiment, the proteins of the invention comprise the cysteine distribution pattern C-$(X)_{81-91}$-C-$(X)_{22-26}$-C-$(X)_{10-12}$-C(SEQ ID NO:59), wherein X is any amino acid.

In one embodiment, the proteins of the invention comprise the cysteine distribution pattern C-$(X)_{81-92}$-C-$(X)_{22-26}$-C-$(X)_{10-12}$-C (SEQ ID NO:60), wherein X is any amino acid.

In one embodiment, the proteins of the invention comprise the cysteine distribution pattern C-$(X)_{82-92}$-C-$(X)_{23-26}$-C-$(X)_{10-12}$-C (SEQ ID NO:61), wherein X is any amino acid.

In one embodiment, the proteins of the invention comprise the cysteine distribution pattern C-$(X)_{81-91}$-C-$(X)_{22-27}$-C-$(X)_{10-12}$C (SEQ ID NO:62), wherein X is any amino acid.

In one embodiment, the proteins of the invention comprise the cysteine distribution pattern C-$(X)_{81-92}$-C-$(X)_{23-27}$-C$(X)_{10-12}$-C (SEQ ID NO:63), wherein X is any amino acid.

In one embodiment, the proteins of the invention comprise the cysteine distribution pattern C-$(X)_{82-92}$-C-$(X)_{22-26}$-C-$(X)_{11-12}$-C (SEQ ID NO:64), wherein X is any amino acid.

In one embodiment, the proteins of the invention comprise the cysteine distribution pattern C-$(X)_{81-91}$-C--$(X)_{22-26}$-C-$(X)_{10-13}$-C(SEQ ID NO:65), wherein X is any amino acid.

In one embodiment, the proteins of the invention comprise the cysteine distribution pattern C-$(X)_{81-92}$-C-$(X)_{22-26}$-C-$(X)_{10-13}$-C (SEQ ID NO:66), wherein X is any amino acid.

In one embodiment, the proteins of the invention comprise the cysteine distribution pattern C-$(X)_{82-92}$-C-$(X)_{23-26}$-C-$(X)_{11-12}$-C. (SEQ ID NO:67), wherein X is any amino acid.

In one embodiment, the proteins of the invention comprise the cysteine distribution pattern C-$(X)_{81-91}$-$(X)_{22-27}$-C-$(X)_{10-13}$-C. (SEQ ID NO:68), wherein X is any amino acid.

In one embodiment, the proteins of the invention comprise the cysteine distribution pattern C-$(X)_{81-92}$-C-$(X)_{23-27}$-C-$(X)_{11-13}$-C(SEQ ID NO:69), wherein X is any amino acid.

In one embodiment, the proteins of the invention comprise the cysteine distribution pattern C-$(X)_{82-91}$-C-$(X)_{22-26}$-C-$(X)_{10-12}$-C(SEQ ID NO:70), wherein X is any amino acid.

In another embodiment, the proteins of the invention comprise the cysteine distribution pattern C-(X)$_{82-91}$-C-(X)$_2$-W-(X)$_{19-23}$-C-(X)$_{10-12}$-C (SEQ ID NO:71), wherein X is any amino acid.

In another embodiment, the proteins of the invention comprise the cysteine distribution pattern and glycosylation site containing sequence C-(X)$_{82-91}$-C-(X)$_2$—W-(X)$_{12-16}$-N-Z-(S/T)-(X)$_4$-C-(X)$_{10-12}$-C(SEQ ID NO:72), wherein X is any amino acid and Z is any amino acid except proline.

The cysteine distribution pattern of the identified proteins has the amino acid residue tryptophan at amino acid position 101 of RaA (SEQ ID NO: 2), 100 of RaB (SEQ ID NO: 4) and 102 of Rs1 (SEQ ID NO: 6). These positions correspond to residue 141 of the amino acid sequence of Japanin (SEQ ID NO: 8). Therefore, in one embodiment the proteins of the invention have a conserved tryptophan residue at a residue corresponding to any one of amino acid positions 100-105 of the sequences of any one of SEQ ID NOs: 2, 4 and 6. In another embodiment the proteins of the invention have a conserved tryptophan residue at a residue corresponding to amino acid position 101 of RaA (SEQ ID NO: 2), 100 of RaB (SEQ ID NO: 4) or 102 of Rs1 (SEQ ID NO: 6).

Further, the cysteine distribution pattern of the identified proteins has the amino acid residue tryptophan at amino acid position 140 of full length RaA protein (SEQ ID NO: 25), position 139 of full length RaB protein (SEQ ID NO: 26) and position 141 of full length Rs1 protein (SEQ ID NO: 24). These positions correspond to residue 141 of the amino acid sequence of Japanin (SEQ ID NO: 8). Therefore, in one embodiment the proteins of the invention have a conserved tryptophan residue at a residue corresponding to any one of amino acid positions 137-143 of the sequences of any one of SEQ ID NOs: 24, 25 and 26. In another embodiment the proteins of the invention have a conserved tryptophan residue at a residue corresponding to amino acid position 140 of full length RaA protein (SEQ ID NO: 25), position 139 of full length RaB protein (SEQ ID NO: 26) and position 141 of full length Rs1 protein (SEQ ID NO: 24). In another embodiment the proteins of the invention have a conserved tryptophan residue at the amino acid position which corresponds to amino acid position 141 of the amino acid sequence of Japanin (SEQ ID NO: 8).

As discussed above, the present invention includes homologues and fragments of the amino acid sequences of SEQ ID NOs: 2, 4 and 6 or of SEQ ID NOs 24, 25, 26, 27, 28 or 29. In certain embodiments the homologues or fragments may the retain cysteine distribution pattern of the proteins of the invention, and may retain the consensus sequence described above.

Lipid Binding Properties

Given its putative lipocalin structure, the proteins of the invention are thought to be associated with a lipid or lipid-like molecule. The term "lipid" is intended to encompass any hydrophobic or amphiphilic molecule which is soluble in organic solvents but insoluble in water. This includes fats, oils, triacylglycerols, glycolipids, phospholipids and steroids, fatty acyls, fatty acids, glycerolipids, glycerophospholipids, sphingolipids, saccharolipids, polyketides, sterol lipids and prenol lipids. The term "lipid-like molecule" encompasses any molecule having similar or identical properties to a lipid. Also included within the term "lipid-like molecule" is any lipid complexed to a non-lipid molecule. This includes glycolipids, phospholipids, phosphoglycolipids, labeled lipids and acetylated lipids.

In vivo, the protein of the invention may become bound to a lipid molecule during or immediately after its folding in the endoplasmatic reticulum or at a subsequent stage after its export from this location.

Within the scope of the invention, the protein of the invention, or homologues or fragments thereof may become associated with the lipid during its production. For example, if the protein of the invention is isolated from its natural source, or produced recombinantly, the protein may automatically become associated with the lipid without any intervention being required. Alternatively, the lipid may be added to a composition comprising the protein of the invention in order to allow complex formation to occur between the lipid and the protein. In particular, if the protein has been chemically synthesised, the lipid may be added exogenously to a composition comprising the protein in order for complex formation to occur.

As described above, the protein of the invention may be "associated" or "complexed" with the lipid. These terms are used interchangeably herein to relate to any sort of contact between the lipid and the protein of the invention. In particular, there may be an interaction between the protein of the invention and the lipid. In one embodiment, this interaction may be purely structural i.e. the lipid may fit into a binding pocket within the protein through a tessellating relationship. In another embodiment, the lipid may physically interact with the protein through any attractive force. Such attractive forces may include electrostatic interactions, hydrophobic interactions, hydrophilic interactions, van der Waals forces, hydrogen bonds, and covalent interactions. The interaction between the lipid and the protein may be formed from a combination of a structural interaction and an attractive force.

In one embodiment, the protein of the invention may be associated with a lipid. In another embodiment the lipid may be a steroid or a sterol, for example cholesterol. In another embodiment, the lipid may be a metabolite of cholesterol, such as vitamin D3 or dexamethasone. The invention thus provides a complex which comprises or consists of a protein of the invention and a lipid, for example cholesterol or a metabolite of cholesterol.

As discussed above, the present invention includes homologues and fragments of the amino acid sequences of SEQ ID NOs: 2, 4 and 6 or of SEQ ID NOs 24, 25, 26, 27, 28 or 29. In certain embodiments the homologues or fragments may retain the lipid binding properties of the full length proteins of SEQ ID NOs: 2, 4 and 6. In other certain embodiments the homologues and fragments may retain the ability to bind cholesterol or a metabolite of cholesterol such as vitamin D3 or dexamethasone. Accordingly, the invention also includes a complex which comprises or consists of a homologue or fragment of a protein of the invention and a lipid, for example cholesterol or a metabolite of cholesterol.

As DC modulatory proteins of the invention are implicated in cholesterol binding, the inventors conceive that proteins which have been engineered to carry a lipid, but do not retain the biological activity of the DC modulatory proteins of the invention may have useful properties. The invention therefore includes a carrier protein which binds a lipid and targets a receptor on the surface of DCs. Such a carrier protein does not itself possess biological activity to modulate, and preferably inhibit, the maturation and differentiation of DCs. In one embodiment, a carrier protein may be produced by engineering a modulatory protein of the invention to prevent its biological activity. In another embodiment, the lipid carried by the carrier protein may confer a biological function by binding to a cellular receptor. The term "functional equivalent" as used above thus includes carrier proteins.

CXXW (SEQ ID NO:33) motif

The inventors have surprisingly discovered that all of the identified DC modulatory proteins share a CXXW (SEQ ID NO:33) motif, where X is any amino acid. The inventors have postulated that this motif is likely to be involved in the formation of the specific lipocalin structure of the DC modulatory proteins. The CXXW (SEQ ID NO:33) motif may be involved in the binding of a lipid, for example cholesterol within the barrel-like structure of the lipocalin. The lipid may become bound to one of the residues of this motif, or the motif may result in the formation of a binding pocket of suitable size to facilitate binding of a lipid within the barrel structure.

The CXXW (SEQ ID NO:33) motif of the identified proteins is present at amino acid positions 98-101 of RaA (SEQ ID NO: 2), 97-100 of RaB (SEQ ID NO: 4) and 99-102 of Rs1 (SEQ ID NO: 6). These positions correspond to residues 138-141 of the amino acid sequence of Japanin (SEQ ID NO: 8). Therefore, in one embodiment the proteins of the invention have a conserved CXXW (SEQ ID NO:33) motif at residues corresponding to any one of amino acid positions 95-105 of the sequences of any one of SEQ ID NOs: 2, 4 and 6. In another embodiment the proteins of the invention have a conserved CXXW (SEQ ID NO:33) motif at residues corresponding to amino acids 98-101 of RaA (SEQ ID NO: 2), 97-100 of RaB (SEQ ID NO: 4) or 99-102 of Rs1 (SEQ ID NO: 6). Further, the CXXW (SEQ ID NO:33) motif of the identified proteins is present at amino acid positions 137-140 of full length RaA protein (SEQ ID NO: 25), positions 136-139 of full length RaB protein (SEQ ID NO: 26) and positions 138-141 of full length Rs1 protein (SEQ ID NO: 24). These positions correspond to residues 138-141 of the amino acid sequence of Japanin (SEQ ID NO: 8). Therefore, in one embodiment the proteins of the invention have a conserved CXXW (SEQ ID NO:33) motif at residues corresponding to any one of amino acid positions 133-144 of the sequences of any one of SEQ ID NOs: 24, 25 and 26. In another embodiment the proteins of the invention have a conserved CXXW (SEQ ID NO:33) motif at residues corresponding to amino acids positions 137-140 of full length RaA protein (SEQ ID NO: 25), positions 136-139 of full length RaB protein (SEQ ID NO: 26) and positions 138-141 of full length Rs1 protein (SEQ ID NO: 24). In another embodiment the proteins of the invention have a conserved CXXW (SEQ ID NO:33) motif at the amino acid positions which corresponds to amino acids 138-141 of the amino acid sequence of Japanin (SEQ ID NO: 8).

In one embodiment, the DC modulatory protein of the invention may comprise the motif CXXW (SEQ ID NO:33), wherein X is any amino acid.

In another embodiment, the DC modulatory protein of the invention may comprise the motif CXLW (SEQ ID NO:34), wherein X is any amino acid.

In yet another embodiment the DC modulatory protein of the invention may comprise the motif CSLW (SEQ ID NO:35) or CELW (SEQ ID NO:36).

In certain embodiments the CXXW (SEQ ID NO:33) motif may be followed by a valine residue and the proteins of the invention may therefore include the motif CXXWV (SEQ ID NO:37). Within this embodiment the motif may comprise the residues CXLWV (SEQ ID NO:38), CSLWV (SEQ ID NO:39) or CELWV (SEQ ID NO:40).

The inventors have hypothesised that the motif forms part of the barrel-like structure of the lipocalin fold, and that the small size of the serine residue in the CSLW (SEQ ID NO:35) motif allows a lipid molecule, such as cholesterol to enter the barrel and become bound within the barrel structure. Therefore, in a preferred embodiment the proteins of the invention comprise a CSLW (SEQ ID NO:35) motif.

As discussed above, the present invention includes homologues and fragments of the amino acid sequences of SEQ ID NOs: 2, 4 and 6 or of SEQ ID NOs 24, 25, 26, 27, 28 or 29. In certain embodiments the homologues or fragments may retain the CXXW (SEQ ID NO:33) motif. In other certain embodiments the homologues and fragments may retain the CXLW (SEQ ID NO:34) motif or the CELW (SEQ ID NO:36) or CSLW (SEQ ID NO:35) motif.

Receptor Binding

The DC modulatory proteins of the invention are thought to bind to a $Ca^{2+}$ dependent receptor. This receptor may be a lectin receptor and in particular may be a C-type lectin cell surface receptor. This suggests that these proteins function to modulate, and preferably inhibit, the differentiation and/or maturation of dendritic cells by binding to a receptor on the surface of the target cell and triggering an internal cell signalling pathway which causes the inhibition.

The proteins of the invention may modulate directly or indirectly a target cell such as a DC.

In one embodiment, the protein may bind to a receptor on the outer surface of a target cell, for example a DC. In another embodiment, the protein may bind to a divalent cation-dependent receptor. In another embodiment the protein may bind to a $Ca^{2+}$ dependent receptor. In another embodiment the protein may bind to a lectin receptor and in particular may bind to a C-type lectin receptor. In one embodiment, the protein may bind to a receptor and mimic a natural ligand for the receptor. It will be apparent to a person skilled in the art that any part of the protein may bind to the receptor. In particular, if the protein is glycosylated and/or bound to a lipid molecule, it may be the carbohydrate moiety or the associated lipid which binds to the receptor on the target cell.

In a further embodiment, the protein may bind to a receptor that is internal to a target cell. For example, the protein may bind to an internal receptor on the surface of a lysosome or other cell organelle.

In one embodiment, the protein of the invention may indirectly modulate a DC cell by binding to one or more intermediate proteins (e.g. a plasma protein) in which the intermediate protein directly or indirectly modulates a DC. For example, the intermediate protein may directly bind to a DC receptor.

In one embodiment there is included within the invention a complex comprising or consisting of a protein of the invention and the receptor. In another embodiment, the complex may comprise or consist of a protein of the invention, the receptor, for example a divalent cation-dependent receptor such as a C-type lectin receptor and a lipid, for example cholesterol or a metabolite of cholesterol.

Antibodies

The invention also provides an antibody which binds the proteins and fragments and homologues thereof of the present invention. The antibody may be used as a reagent for the detection of proteins of the invention. It may also be an antibody that neutralises the activity of proteins of the invention in modulating or inhibiting the DC differentiation and/or maturation and is thus useful for therapeutic purposes, as described below. Included within this aspect of the invention are antibodies which bind to any of the homologues and protein fragments included within the scope of the invention, as described above.

The invention also includes antibodies which bind to a carbohydrate moiety of the protein of the invention. In particular, the invention includes antibodies which bind to one or more of the carbohydrate moieties naturally attached to the proteins of the invention and homologues and fragments thereof.

In one embodiment, the invention includes antibodies that mimic the ability of proteins of the invention to modulate, and preferably inhibit, the differentiation and/or maturation of DCs.

"Anticalins" are also included within the scope of the invention. These are molecules which are engineered from lipocalins to recognise and bind specific protein epitopes. In certain embodiments anticalins may take the form of peptides, glycopeptides or glycolipids. Herein, anticalins are included within the scope of the term "antibodies". Anticalins are non-immunoglobulin-derived molecules which nevertheless recognise protein epitopes in a manner similar to antibodies.

If polyclonal antibodies are desired, a selected mammal, such as a mouse, rabbit, pig, goat or horse, may be immunised with a protein of the invention or a homologue or fragment thereof. If desired, the protein can be conjugated to a carrier protein. Commonly used carrier proteins include bovine serum albumin, thyroglobulin and keyhole limpet haemocyanin. The coupled protein is then used to immunise the animal. Serum from the immunised animal is collected and treated according to known procedures, for example by immunoaffinity chromatography.

Monoclonal antibodies to the proteins of the invention and homologues and fragments thereof can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R. Liss, Inc. (1985).

As used herein, the term "antibody" includes full length antibodies and fragments of antibodies, such as Fab, $F(ab')_2$ and Fv fragments, which also bind specifically to a protein of the invention or a homologue or fragment thereof. The term "antibody" further includes chimeric and humanised antibody molecules having specificity for the proteins of the invention and homologues and fragments thereof. Chimeric antibodies are antibodies in which non-human variable regions are joined or fused to human constant regions (see, for example, Liu et al., Proc. Natl. Acad. Sci. USA, 84, 3439 (1987)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody (see Jones et al., Nature, 321, 522 (1986); Verhoeyen et al., Science, 239, 1534 (1988); Kabat et al., J. Immunol., 147, 1709 (1991); Queen et al., Proc. Natl. Acad. Sci. USA, 86, 10029 (1989); Gorman et al., Proc. Natl. Acad. Sci. USA, 88, 34181 (1991); and Hodgson et al., Bio/Technology, 9, 421 (1991)). Such humanised antibodies are also included within the scope of the invention.

The term "antibody" also includes a "plastic" antibody (molecularly imprinted polymer (MIP)).

In some cases, it may be desirable to attach a label group to the antibody, e.g. to facilitate detection. The label may be an enzyme, a radiolabel, a compound such as biotin, or a fluorochrome. Such labelled antibodies are also within the scope of the invention.

Fusion Proteins

The invention also includes a fusion protein comprising a protein of the invention or a homologue or fragment thereof that is genetically fused or chemically linked to one or more peptides, polypeptides or other molecules. The purpose of the additional peptide or polypeptide or molecule may be to aid detection, expression, separation or purification of the protein or it may be to confer additional properties to the protein as desired. Examples of potential fusion partners include beta-galactosidase, glutathione-S-transferase, luciferase, a polyhistidine tag, a T7 polymerase fragment and a secretion signal peptide. The fusion partner may also extend the life of the molecules in vivo, e.g. an Fc fragment.

Other potential fusion partners include potential biopharmaceuticals, such as proteins or other molecules that are being developed for use as drugs to treat specific diseases. Further potential fusion partners include antigens that will target the protein of the invention to cells within the immune system, such as DCs. For example, fusion partners may include a self or foreign antigen or an allergen which may be fused to the protein to deliver it to the DCs in vivo. Further fusion partners may include molecules that bind to a different cell surface component of the DC to facility delivery to the DC. Examples of such antigens are discussed in more detail below in relation to methods of treatment. In some cases, multiple fusion partners may be included.

Nucleic Acids

The invention also includes a nucleic acid molecule comprising a nucleic acid sequence encoding a protein of the invention. Included within the term "nucleic acid molecule" are DNA molecules, RNA molecules and mixed DNA-RNA molecules. Further included within this definition are genomic DNA, cDNA molecules, mRNA molecules and RNA and DNA molecules containing modified bases. As will be apparent to a person skilled in the art, the degeneracy of the genetic code provides that there will be a number of different nucleic acid sequences which are capable of encoding the defined protein sequence of a protein of the invention or a homologue or fragment thereof. The invention also includes a nucleic acid molecule encoding a fusion protein, such as the fusion proteins described above.

In one aspect of the invention, the nucleic acid molecule comprising a nucleic acid sequence encoding a protein of the invention may comprise or consist of the nucleotide sequence of any one of SEQ ID NOs: 1, 3, 5 or a degenerate sequence thereof. In a further aspect of the invention, the nucleic acid molecule comprising a nucleic acid sequence encoding a protein of the invention may comprise or consist of the nucleotide sequence of any one of SEQ ID NOs: 41, 42 or 43 or a degenerate sequence thereof.

The invention also provides an antisense nucleic acid molecule which hybridises under high stringency hybridisation conditions to a nucleic acid molecule comprising a nucleic acid sequence encoding a protein of the invention, or a homologue or fragment thereof, as described above. High stringency hybridisation conditions include overnight incubation at 42° C. in a solution comprising 50% formamide, 5×SSC (150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C. Antisense nucleic acid molecules include antisense DNA oligonucleotides, and RNA oligonucleotides including siRNA.

The invention also includes a vector containing a nucleic acid molecule comprising a nucleic acid sequence encoding a protein of the invention or a homologue or fragment thereof or an antisense nucleic acid molecule which hybridises under high stringency hybridisation conditions to said nucleic acid molecule. Said vectors include cloning and expression vectors. Such expression vectors may incorporate the appropriate transcriptional and translational control sequences, for example enhancer elements, promoter-operator regions, termination stop sequences, mRNA stability sequences, start and stop codons or ribosomal binding sites, linked in frame with the nucleic acid molecules of the invention. These control sequences are provided by way of example only, and are not intended to be limited.

Additionally, it may be convenient for a recombinant protein to be secreted from certain hosts. Accordingly, further components of such vectors may include nucleic acid sequences encoding secretion, signalling and processing sequences.

Vectors according to the invention may include plasmids and viruses (including both bacteriophage and eukaryotic viruses), as well as other linear or circular DNA carriers, such as those employing transposable elements or homologous recombination technology. Particularly suitable viral vectors include baculovirus-, lentivirus-, adenovirus- and vaccinia virus-based vectors.

The invention also includes a host cell containing a vector, a nucleic acid molecule or an antisense nucleic acid encoding a protein of the invention or a homologue or fragment thereof. Within the scope of the invention, any type of host cell may be utilised. In one embodiment, the host cell may be a prokaryotic host cell. Within this embodiment, the prokaryotic host cell may be an *E. coli* host cell. In another embodiment, the host cell may be a eukaryotic host cell. Within this embodiment the host cell may be a eukaryotic yeast cell. In a further embodiment the host cell may be a mammalian host cell. In a still further embodiment the host cell may be an insect cell, and within this embodiment the expression system may be the baculovirus expression system.

A variety of techniques may be used to introduce the vectors or nucleic acids of the present invention into host cells. Suitable transformation or transfection techniques are well described in the literature (Sambrook et al, 1989; Ausubel et al, 1991; Spector, Goldman & Leinwald, 1998). In eukaryotic cells, expression systems may either be transient (e.g. episomal) or permanent (chromosomal integration) according to the needs of the system.

In a further embodiment of the invention, there is provided a method of preparing a protein of the invention, or a homologue or fragment thereof comprising:
  i) culturing a host cell containing a vector comprising a nucleic acid sequence which encodes a protein of the invention or a homologue or fragment thereof under conditions whereby said protein is expressed; and
  ii) recovering said protein thus produced.

Within this aspect of the invention, the conditions required for protein expression will vary depending upon the host cell system, the vector and the subsequent method of protein recovery. One example of a particular process for production and recovery of the proteins of the invention includes infecting Sf9 insect cells with a recombinant baculovirus encoding a protein of the invention and precipitating the resulting protein from the culture supernatant by the addition either of polyethylene glycol (PEG) or ammonium sulphate. Variation in such conditions will be apparent to a person skilled in the art.

Pharmaceutical Compositions

Due to the identified activity of the proteins of the present invention in the modulation, and preferably inhibition, of the differentiation and/or maturation of DCs, the proteins, nucleic acids, antisense nucleic acids, vectors, host cells and antibodies of the present invention are intended to be used as therapeutics.

The invention provides a pharmaceutical composition comprising a DC modulatory protein which modulates, and preferably inhibits, the differentiation and/or maturation of DCs, or a functional equivalent or fragment thereof, a nucleic acid encoding such a protein, homologue or fragment, a vector containing said nucleic acid, a host cell containing said vector or an antibody which binds to said protein, homologue or fragment and a pharmaceutically acceptable carrier.

The term "pharmaceutically acceptable carrier", as used herein, includes genes, polypeptides, antibodies, liposomes, polysaccharides, polylactic acids, polyglycolic acids and inactive virus particles or indeed any other agent provided that the excipient does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. Excipients may enable the pharmaceutical compositions to be formulated into tablets, pills, dragees, capsules, liquids, gels, syrups, slurries, or suspensions to aid intake by the patient. A thorough discussion of pharmaceutically acceptable carriers is available in Remington's Pharmaceutical Sciences (Mack Pub. Co., N.J. 1991).

In one embodiment, the pharmaceutical composition may include one or more lipid molecules which interact with the protein. In one specific embodiment, this lipid molecule may be a steroid or a sterol, for example cholesterol or a metabolite of cholesterol, such as vitamin D3 or dexamethasone. In another embodiment the pharmaceutical composition may include a complex which comprises or consists of a protein of the invention and a lipid, for example cholesterol or a metabolite of cholesterol such as vitamin D3 or dexamethasone. In a further embodiment, the pharmaceutical composition may include a complex which comprises or consists of a protein of the invention, a lipid, for example cholesterol or a metabolite of cholesterol such as vitamin D3 or dexamethasone, and a receptor, for example a divalent cation-dependent receptor such as a C-type lectin receptor.

In one aspect of the invention, the pharmaceutical composition may also include one or more additional therapeutic agents. Included within this aspect of the invention are any additional therapeutic agents which the skilled person might consider would be advantageous for co-administration with the proteins of the invention. In particular, said additional therapeutic agent may comprise an anti-inflammatory agent, an immunomodulatory agent, an immunosuppressant, a cytokine, a cytokine mimetic or a cytokine binding protein. In particular embodiments, the one or more additional therapeutic agents may include an anti-inflammatory agent.

Methods of Treatment

The present invention provides a protein, which modulates, and preferably inhibits, the differentiation and/or maturation of mammalian DCs, a nucleic acid encoding such a protein, an antisense nucleic acid, a vector containing said nucleic acid or antisense nucleic acid, a host cell containing said vector, an antibody which binds to said protein or a pharmaceutical composition comprising said protein, nucleic acid, vector, host cell or antibody for use in therapy.

As used herein, the term "therapy" includes use of the proteins, nucleic acids, vectors, host cells, antibodies or pharmaceutical compositions described herein for the benefit of a human or animal patient. Specifically this term includes therapeutic treatment, prophylactic treatment, diagnosis, and vaccination. This list is provided by way of illustration only, and is not intended to be limiting.

The proteins, nucleic acids, vectors, host cells, antibodies or pharmaceutical compositions of the present invention may be used for the treatment of any animal. In some embodiments, this animal may be a fish. In some embodiments, this animal may be a mammal. In further embodiments, this mammal may be a cow, pig, sheep, cat, dog, bird such as a chicken, or rabbit. In further embodiments, the mammal may be a human. In a further embodiment, the animal may be a reptile.

In another embodiment, there is provided the use of a DC modulatory protein, a nucleic acid encoding such a protein, an antisense nucleic acid capable of binding to the nucleic acid encoding such a protein, a vector containing said nucleic acid or antisense nucleic acid, a host cell containing said vector, an antibody which binds to said protein or nucleic acid molecule or a pharmaceutical composition comprising said protein, nucleic acid, vector, host cell or antibody in the manufacture of a medicament for treating diseases associated with DC activity.

The invention also provides a method of treating an animal suffering from a disease associated with DC activity comprising administering to said animal a DC modulatory protein, a nucleic acid encoding such a protein, an antisense nucleic acid capable of binding to the nucleic acid encoding such a protein, a vector containing said nucleic acid or antisense nucleic acid, a host cell containing said vector, an antibody which binds to said protein or a pharmaceutical composition comprising said protein, nucleic acid, vector, host cell or antibody in a therapeutically effective amount.

Within the scope of the invention, the proteins, nucleic acids, vectors, host cells, antibodies or pharmaceutical compositions of the present invention may be administered to a patient using any one or more of a number of modes of administration. Such modes of administration are well known in the art and may include parenteral injection (e.g. intravenously, subcutaneously, intraperitoneally, intramuscularly, or to the interstitial space of a tissue), or by rectal, oral, vaginal, topical, transdermal, intradermal, intrathecal, intranasal, ocular, aural, pulmonary or other mucosal administration. Nanopatches may be used for transdermal administration of the proteins, nucleic acids, vectors, host cells, antibodies or pharmaceutical compositions of the present invention. Gene guns may also be used to administer the nucleic acids, vectors, or pharmaceutical compositions of the invention. The precise mode of administration will depend on the disease or condition to be treated.

In one embodiment, the proteins, nucleic acids, vectors, host cells, antibodies or pharmaceutical compositions of the invention may be used in the treatment or prevention of autoimmune disorders, allergies or other hypersensitivity disorders, transfusion reactions, transplant reactions including transplant reactions such as transplant rejection and graft-versus-host disease, and acute and chronic inflammatory diseases.

The autoimmune disorders include but are not limited to achlorhydra autoimmune chronic active hepatitis, Addison's disease, alopecia greata, amyotrophic lateral sclerosis (ALS, Lou Gehrig's Disease), ankylosing spondylitis, anti-GBM nephritis or anti-TBM nephritis, antiphospholipid syndrome, aplastic anemia, arthritis, asthma, atopic allergy, atopic dermatitis, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Balo disease, Behcet's disease, Berger's disease (IgA Nephropathy), bullous pemphigoid, cardiomyopathy, celiac disease, celiac sprue dermatitis, chronic fatigue immune deficiency syndrome (CFIDS), chronic fatigue immune dysfunction syndrome (CFIDS or chronic fatigue syndrome (CFS)), chronic inflammatory demyelinating polyneuropathy, Churg Strauss syndrome, cicatricial pemphigoid, Cogan's syndrome, cold agglutunin disease, colitis, cranial arteritis, CREST syndrome, Crohn's disease, Cushing's syndrome, Dego's disease, dermatitis, dermatomyositis, dermatomyositis—juvenile, Devic's disease, type 1 diabetes, discoid lupus, Dowling-Dego's disease, Dressler's syndrome, eosinophilic fasciitis, epidermolysis bullosa acquisita, essential mixed cryoglobulinemia, Evan's syndrome, fibromyalgia, fibromyositis, fibrosing alveolitis, gastritis, giant cell artertis, glomerulonephritis, Goodpasture's disease, Grave's disease, Guillian-Barre syndrome, Hashimoto's thyroiditis, hemolytic anemia, Henoch-Schonlein purpura, hepatitis, Hughes syndrome, idiopathic adrenal atrophy, idiopathic pulmonary fibrosis, idiopathic thrombocytopenia purpura (ITP), IgA nephropathy, inflammatory demylinating polyneuropathy, insulin dependent diabetes (Type I), irritable bowel syndrome, juvenile arthritis, Kawasaki's disease, lichen planus, Lou Gehrig's disease, lupoid hepatitis, Lyme disease, Meniere's disease, mixed connective tissue disease, multiple myeloma, multiple sclerosis, myasthenia gravis, myositis, ocular cicatricial pemphigoid, osteoporosis, pars planitis, pemphigus vulgaris, pernicious anemia, polyarteritis nodosa, polychondritis, polyglandular syndromes, polyglandular autoimmune syndromes, polymyalgia rheumatica (PMR), polymyositis, polymyositis and dermatomyositis, primary agammaglobulinemia, primary biliary cirrhois, primary biliary cirrhosis, primary sclerosing cholangitis, psoriasis, Raynaud's phenomenon, Reiter's syndrome, rheumatoid arthritis, sarcoidosis, scleritis, scleroderma, Sjogren's syndrome, sticky blood syndrome (or Hughes syndrome), stiff-man syndrome, Still's disease, Sydenham's chorea, systemic lupus erythmatosis (SLE), Takayasu's arteritis, temporal arteritis/giant cell arteritis, ulcerative colitis, uveitis, vasculitis, vitiligo, Wegener's granulomatosis, and Wilson's syndrome.

The allergy or other immune-related sensitivity may be any known hypersensitivity disease including type I, type II, type III, or type IV according to the Gell-Coombs classification, and the less commonly defined type V hypersensitivity disorders. Such disorders include but are not limited to atopy, asthma, ertyhroblastosis fetalis, Goodpasture's syndrome, autoimmune hemolytic anemia, serum sickness, Arthus reaction, systemic lupus erythematosus, contact dermatitis, tuberculin skin test, chronic transplant rejection, Graves disease, myasthenia gravis, systemic anaphylaxis, local anaphylaxis, allergic rhinitis, conjunctivitis, gastroenteritis, eczema, blood transfusion reactions, haemolytic disease of the newborn, rheumatoid arthritis, glomerulonephritis, contact dermatitis, atopic dermatitis, tubercular lesions, drug-induced hemolytic anemia, lupus nephritis, aspergillosis, polyarteritis, polymyositis, scleroderma, hypersensitivity pneumonitis, Wegener's granulomastosis, type I diabetes mellitus, urticaria/angioedema, or inflammation of the thyroid. The allergy or hypersensitivity disorder may be associated with infectious diseases including but not limited to tuberculosis, leprosy, blastomycosis, histoplasmosis, toxoplasmosis, leishmaniasis or other infections. Allergies that may be treated include but are not limited to allergic reactions to pollens (e.g. birch tree, ragweed, oil seed rape), food (e.g. nuts, eggs or seafood), drugs (e.g. penicillin or salicylates), insect products (e.g. bee or wasp venom or house dust mites) or animal hair, and man-made products such as latex. Allergies that may be treated may also include allergic reactions to arthropod products. Other inflammatory diseases that may be treated include atherosclerosis or other cardiovascular disease, Alzheimer's disease, vasculisitis, myositis, encephalitis, reperfusion injury, type 2 diabetes, fatty liver disease, and wound healing, including the inflammatory phase, the process of angiogenesis, fibroplasmia and epithelialisation, and the remodeling phase. Further inflammatory diseases that may be treated include cystic fibrosis, bronchiectasis and chronic obstructive pulmonary disease (COPD).

The proteins, nucleic acids, vectors, host cells, antibodies or pharmaceutical compositions of the invention may also be used in the treatment or prevention of nasal polyposis, pre-eclampsia pregnancy induced hypertension, Eales' disease or acute pancreatitis.

In one embodiment, the proteins, nucleic acids, vectors, host cells, antibodies or pharmaceutical compositions of the invention may be used in the treatment or prevention of harmful conditions resulting from bodily fluids or tissues coming into contact with artificial or non-mammalian materials during the course of therapeutic or diagnostic procedures. Such procedures may be temporary or permanent and include but not be limited to the use of extracorporeal circuits including renal or hepatic haemodialysis, peritoneal dialysis, cardiopulmonary bypass and haemofiltration, indwelling catheters whether placed in blood vessels, the urinary bladder, the intrathecal space or any other hollow viscus, implanted prostheses including artificial joints, heart valves, endovascular stents, CSF shunts, vascular prostheses and coronary angioplasty catheters.

The proteins, nucleic acids, vectors, host cells, antibodies or pharmaceutical compositions of the invention are likely to have an immunosuppressant effect that may be useful in preventing transplantation reactions such as transplant rejection. The transplants may be autografts between the same individual, isografts between genetically matched individuals, allografts between different members of the same species or xenografts between different species. The proteins of the invention may be useful in preventing rejection of a range of transplants including, but not limited to heart, lung, heart and lung, kidney, liver, pancreas, intestine, hand, cornea, skin graft including face replant and face transplants, islets of Langerhans, bone marrow transplants, blood transfusion, blood vessels, heart valves, bone and skin. The proteins, nucleic acids, vectors, host cells, antibodies or pharmaceutical compositions of the invention may be used to prevent graft-versus host disease following bone marrow transplantation.

Although the inventors do not wish to be bound by theory, it is postulated that the proteins of the invention may be involved in inhibiting signalling pathways involved in cancer. In a further embodiment of the present invention, the proteins, nucleic acids, vectors, host cells, antibodies or pharmaceutical compositions of the invention may be used in the treatment of cancer. The invention also provides a method of treating an animal suffering from cancer comprising administering to said animal a protein, nucleic acid, vector, antibody, or pharmaceutical composition of the invention, as described above in a therapeutically effective amount. Such treatment may involve the repolarisation or modulation of the immune response in cancer.

In particular, the cancer may be a haematological cancer such as lymphoma or leukaemia or multiple myeloma. Leukemias that may be treated according to the invention include acute lymphoblastic leukaemia (ALL), acute myelogenous leukaemia (AML), chronic myelogenous leukaemia (CML), chronic lymphocytic leukaemia (CLL) and hairy cell leukaemia. Lymphomas that may be treated according to the invention include Hodgkin's disease and non-Hodgkin's lymphoma. Related disorders may also be treated including myelodysplastic syndrome (MDS) which can culminate in ALL, myeloproliferative disease including polycythemia vera, essential thrombocytosis or myelofibrosis, and amyloid due to light-chain disease.

In further embodiments, the cancer may be a carcinoma, a sarcoma, or a blastoma. The invention contemplates the treatment of cancers of any organ including but not limited to cancers of the breast, lung, ovaries, pancreas, testes, skin, colon, brain, liver or cervix, as well as melanoma. A cancer that may be treated or prevented is histiocytoma and in particular canine cutaneous histiocytoma.

In a further embodiment of the present invention, the proteins, nucleic acids, vectors, host cells, antibodies or pharmaceutical compositions of the invention may be used in the treatment of infectious disease. In particular, such treatment may involve the repolarisation or modulation of the immune response to infections by pathogens such as viruses, bacteria and protozoa, e.g. the causative agents of HIV, TB and malaria, as well as other parasites.

Haematophagous arthropods, such as ticks are sources of infectious disease agents such as tick-borne encephalitis virus, Crimean-Congo haemorrhagic fever virus, Nairobi sheep virus, *Borrelia burgdorferi* (the agent of Lyme's disease), and *Theileria parva* (the agent of East Coast fever). It is postulated that the proteins of the invention may act to promote transmission of tick-borne diseases. The proteins of the invention and homologues and fragments thereof may therefore be useful in the vaccination of animals to induce an immune response to treat or prevent tick-borne diseases. In a further embodiment of the invention there is therefore provided a method of preventing transmission of an arthropod-borne infectious disease or treating an arthropod-borne infectious disease comprising administering to an animal a protein, nucleic acid molecule, vector, host cell, antibody or pharmaceutical composition of the invention. The invention also provides a protein, nucleic acid molecule, vector, host cell, antibody or pharmaceutical composition of the invention for use in preventing transmission of an arthropod-borne infectious disease or treating an arthropod-borne infectious disease. The arthropod may be a haematophagous arthropod. The arthropod-borne disease may be Lyme's disease, tick-borne encephalitis, Crimean-Congo haemorrhagic fever, Nairobi sheep virus or East coast fever.

The proteins of the invention and homologues and fragments thereof may also be useful as vaccines against the haematophagous arthropods themselves, as well as the diseases carried by them. The invention therefore further provides a method of vaccinating an animal against a haematophagous arthropod which may be a tick, comprising administering a protein, nucleic acid molecule, vector, host cell, antibody or pharmaceutical composition of the invention to said animal. The invention also provides a protein, nucleic acid molecule, vector, host cell, antibody or pharmaceutical composition of the invention for use in vaccinating an animal against a haematophagous arthropod which may be a tick.

As discussed above, it may be advantageous to administer proteins, nucleic acids, vectors, host cells, antibodies or pharmaceutical compositions of the invention in combination with one or more additional therapeutic agents such as an anti-inflammatory agent, an immunomodulatory agent, an immunosuppressant, a cytokine, a cytokine mimetic or a cytokine binding protein, or another biopharmaceutical developed for the treatment of any of the disorders mentioned above.

It may also be advantageous to administer the proteins, nucleic acids, vectors, host cells or antibodies of the invention with an antigen that will target them to DCs in vivo to modulate or inhibit the differentiation and maturation of DCs associated with the unwanted immune response. In this embodiment, the proteins, nucleic acids, vectors, host cells, antibodies or pharmaceutical compositions of the present invention may be administered to the patient in combination with a disease-associated element to aid targeting of the proteins, nucleic acids, vectors, host cells, antibodies or pharmaceutical compositions of the present invention to the appropriate DCs. In embodiments where the proteins, nucleic acids, vectors, host cells or antibodies of the invention already target DCs by binding to them specifically, a disease associated element may not be necessary.

The term "disease-associated element" is intended to encompass any component which is associated with the disease in a patient. The disease may include autoimmune disorders, allergies and other hypersensitivity reactions, transplant reactions such as transplant rejection and graft-versus-host disease, infectious diseases including those transmitted by ticks, cancers including haematological malignancies, and acute and chronic inflammatory diseases, as described above. The "disease associated element" may thus include: i) components associated with infectious agents, such as viruses, microbes, parasites and microbial toxins; ii) allergens that are non-self molecules associated with allergy; iii) non-self components associated with hypersensitivity reactions other than allergy; iv) self-components associated with autoimmune diseases; v) transplantation antigens from genetically-different members of the same species (alloantigens) or from different species (xenoantigens); and vi) tumour-associated antigens and tumour-specific antigens.

The term "disease associated element" also encompasses fragments and derivatives of these disease-associated elements. Such derivatives may includes detoxified agents, synthetic mimotopes and antigens comprising substitutions, additions or deletions in their structure, which are still capable of acting to direct the proteins, nucleic acids, vectors, host cells, antibodies or pharmaceutical compositions of the invention to the appropriate DCs.

Providing the animal with a disease-associated element will improve the specificity of the modulation or inhibition of DC differentiation and maturation associated with the disease. Targeting specific DCs in this manner is advantageous as it avoids the need to inhibit the overall immune response, and may therefore result in a reduced profile of side effects.

In one aspect of the invention, the proteins, nucleic acids, vectors, host cells, antibodies or pharmaceutical compositions of the invention may be administered separately from the disease associated element. Within this aspect, the proteins, nucleic acids, vectors, host cells, antibodies or pharmaceutical compositions of the invention and the disease associated element may be administered sequentially. In a another embodiment, the proteins, nucleic acids, vectors, host cells, antibodies or pharmaceutical compositions of the invention may be administered before the disease associated element. In a further embodiment, the proteins, nucleic acids, vectors, host cells, antibodies or pharmaceutical compositions of the invention may be administered after the disease associated element.

In a further embodiment, the proteins, nucleic acids, vectors, host cells, antibodies or pharmaceutical compositions of the invention and the disease associated element may be administered simultaneously. Within this aspect of the invention, the proteins, or antibodies of the invention may be bound to the disease associated element, for example in the form of a fusion protein.

The invention therefore also provides, a fusion protein comprising a protein of the invention or a homologue or fragment thereof, and a disease associated element. A nucleic acid encoding such a fusion protein is also provided.

The invention also provides a pharmaceutical composition comprising a protein, nucleic acid, vector, host cell, antibody or pharmaceutical composition of the invention, a disease associated element and a pharmaceutically acceptable carrier.

The methods describe above involve the administration of the proteins of the invention to an animal in order to modulate, and preferably inhibit, the differentiation and/or maturation of DCs in the animal in vivo. The proteins may be administered alone or in combination with additional agents, including disease associated elements that will target the protein of the invention to DCs.

An alternative approach to the treatment of the diseases described above is to use the proteins of the invention for targeted therapy ex vivo. This approach involves delivering a protein of the invention to DCs in vitro to modulate the DCs and delivering the modulated DCs to the animal in need of treatment.

In a further aspect, the invention provides a method of modulating a DC, said method comprising contacting a DC with a protein of the invention, or a homologue or fragment thereof. A modulated DC produced using this method is also provided.

The invention also provides a method of treating or preventing a disorder associated with DCs in an animal in need thereof wherein the method comprises administering the modulated DC produced by the method described above to an animal.

The DCs may be isolated directly from the animal in need of treatment. Alternatively, DC precursors, such as monocytes of bone marrow progenitors may be isolated from the animal in need of treatment and used to generate modulated DCs. Within this aspect of the invention, the DC or DC precursors may be autologous or allogeneic with respect to the animal into which the modulated DCs are to be introduced following treatment of the DCs with a protein of the invention.

The disorders associated with DCs may be any of the diseases discussed above including autoimmune disorders, allergies and other hypersensitivity reactions, transplant reactions such as transplant rejection and graft-versus-host disease, infectious diseases including those transmitted by ticks, cancers including haematological malignancies, and acute and chronic inflammatory diseases It is contemplated that this method may be used to generate modulated DCs from a transplant donor to administer to the intended recipient of a transplant prior to transplantation with the aim or inducing unresponsiveness to the graft and thus reducing the need for immunosuppressants to be given.

Within this aspect of the invention, the DCs may also be contacted with a disease associated element, as described above, in order to target the protein of the invention or the homologue or fragment thereof to the appropriate DCs. Alternatively, the modulated DCs may be administered to the animal in combination with a disease-associated element, such as those as described above.

Screening Methods

The identification of the cognate receptor of the proteins of the invention allows the receptor to be used in screening methods to identify potential agonists and antagonists of proteins of the invention in order to identify any compounds which are potentially of therapeutic or other use.

Potential agonist or antagonist compounds may be isolated from, for example, cells, cell-free preparations, chemical libraries or natural product mixtures. For a suitable review of such screening techniques, see Coligan et al., Current Protocols in Immunology 1(2): Chapter 5 (1991).

Compounds that are most likely to be good antagonists are molecules that bind to the protein of the invention's cognate receptor without inducing the biological effects induced by the proteins of the invention, and thus competitively inhibit the function of the proteins of the invention. As described above, the cognate receptor of the proteins of the invention is thought to be a divalent cation-dependent receptor which is a C-type lectin receptor which, upon binding of the proteins of the invention, induces an intracellular signalling pathway leading to inhibition of differentiation and maturation of DCs. Potential antagonists include small organic molecules, peptides, polypeptides and antibodies that bind to the receptor without activating a signalling pathway, or by activating a negative signalling pathway. In particular, suitable potential antagonists include carbohydrate moieties and engineered molecules corresponding to proteins of the invention which have been engineered to reduce their function whilst retaining their binding affinity for the receptor. In a further embodiment potential antagonists include small synthetic molecules that bind to the receptor without activating a signalling pathway or by activating a negative signalling pathway. Further suitable compounds include antibodies to the proteins of the invention and antibodies to the carbohydrate moiety associated with the proteins of the invention, and anticalins which can be engineered for target specificity.

Compounds most likely to function as good agonists are compounds which bind to the cognate receptor of the proteins of the invention and induce the same intracellular signalling pathway as the proteins of the invention, thereby functioning to modulate, and preferably inhibit, the differentiation and maturation of DCs in a similar way to the proteins of the invention. Examples of suitable potential agonists include proteins of the invention which have been engineered to increase their ability to activate the receptor and/or their binding affinity for the receptor. Further examples of suitable potential agonists include small organic molecules, synthetic molecules, peptides, polypeptides fusion proteins, antibodies or antibody fragments.

The cognate receptor (a divalent cation-dependent receptor, possibly a C-type lectin) for use in such a screening technique may be free in solution, affixed to a solid support, borne on a cell surface or located intracellularly. In general, such screening procedures may involve using appropriate cells or cell membranes that express the receptor and that are contacted with a test compound to observe binding, or stimulation or inhibition of a functional response. The functional response of the cells contacted with the test compound is then compared with control cells that were not contacted with the test compound. Such an assay may assess whether the test compound results in the generation of a signal similar to that generated by activation of the receptor by proteins of the invention, using an appropriate detection system. Since the proteins of the invention are believed to function by binding to a cell surface divalent cation-dependent receptor such as a C-type lectin receptor and inducing an intracellular signalling pathway, a screening method is likely to function most effectively if it involves the use of receptors on the cell surface, and the monitoring of the induction of an intracellular signal by the binding of the compound to the receptor.

In one embodiment, a method for identifying an agonist or antagonist compound of the proteins of the invention comprises:

(a) contacting a cell expressing the divalent cation-dependent receptor, for example a C-type lectin receptor, on its surface with a compound to be screened under conditions to permit binding to the receptor, wherein the receptor is capable of providing a detectable signal in response to the binding of a compound; and (b) determining whether the compound binds to and activates or inhibits the receptor by measuring the level of a signal generated from the interaction of the compound with the receptor.

In certain embodiments, the compounds to be screened may be contacted with the receptor in the presence of a ligand. Such a ligand may be a lipid, for example cholesterol or a metabolite of cholesterol, such as vitamin D3 or dexamethasone.

In another embodiment, a method of identifying an antagonist compound of the protein of the invention comprises:

(a) contacting a cell expressing the divalent cation-dependent receptor, for example a C-type lectin receptor, on its surface with a protein of the invention, wherein the receptor is capable of providing a detectable signal in response to the binding of a protein of the invention, under conditions which allow the protein of the invention to bind to its cognate receptor;

(b) measuring the level of a signal generated from the interaction of the protein of the invention with the receptor;

(c) adding a compound to be screened under conditions to permit binding to the receptor; and (d) determining the effect of the compound upon the binding of the protein of the invention by measuring the change in the level of a signal generated from the interaction of the compound with the receptor.

In certain embodiments, any homologue or fragment of the proteins of the invention, as discussed above, may be used in the screening methods described above.

In certain further embodiments, the compounds to be screened and/or the proteins of the invention may be contacted with the receptor in the presence of a ligand. Such a ligand may be a lipid, for example cholesterol or a metabolite of cholesterol.

The conditions indicated above may include the presence of culture medium, the presence of a solution containing a physiological concentration of $Ca^{2+}$, and/or a pH of 7-8.

The detectable signal described above may include intracellular phosphorylation, nuclear localisation, gene expression and/or cytokine release.

In certain embodiments of the methods described above, simple binding assays may be used, in which the adherence of a test compound to a surface bearing a C-type lectin receptor is detected by means of a label directly or indirectly associated with the test compound or in an assay involving competition with a labelled competitor. In another embodiment, competitive drug screening assays may be used, in which neutralising antibodies that are capable of binding the divalent cation-dependent receptor, such as the C-type lectin receptor, specifically compete with a test compound for binding. In this manner, the antibodies can be used to detect the presence of any test compound that possesses specific binding affinity for the receptor.

A person skilled in the art will be able to devise assays for identifying compounds which act on the cognate receptor of the proteins of the present application. A technique which may be used to provide for high throughput screening of compounds having suitable binding affinity to the receptor could readily be identified by those skilled in the art (see International patent application WO84/03564). In this method, large numbers of different small test compounds are synthesised on a solid substrate, which may then be reacted with the receptor and washed. One way of immobilising the polypeptide is to use non-neutralising antibodies. Bound receptor may then be detected using methods that are well known in the art. Purified receptor molecules can also be coated directly onto plates for use in the aforementioned drug screening techniques.

The present invention also includes the agonists, antagonists and other compounds which are identified by the methods that are described above. These agonists, antagonists and other compounds may be form part of the pharmaceutical compositions described above, and may be used in the methods of treatment described above.

Various aspects and embodiments of the present invention will now be described in more detail by way of example. It will be appreciated that modification of detail may be made without departing from the scope of the invention.

BRIEF DESCRIPTION OF FIGURES

FIG. 1 shows the DNA and amino acid sequence of RaA (SEQ ID NOs: 1 & 2).

FIG. 2 shows the alignment of RaA (SEQ ID NO: 2) with Japanin (SEQ ID NO: 8). The alignment of RaA with Japanin was obtained using clustalW with the following options: gap extension penalty-0.1; gap opening penalty-10.0; hydrophilic residues=G, P, S, N, D, Q, E, R or K; matrix=gonnet. Of the 131 residues that form the alignment, 61 (46.56%©) are identical [indicated by *], 26 (19.85%) are strongly similar [:] and 22 (16.79%) are weakly similar H.

FIG. 3 shows the DNA and amino acid sequence of RaB (SEQ ID NOs: 3 & 4).

FIG. 4 shows the alignment of RaB (SEQ ID NO: 4) with Japanin (SEQ ID NO: 8). The alignment of RaB with Japanin was obtained using clustalW with the following options: gap extension penalty=0.1; gap opening penalty=10.0; hydrophilic residues=G, P, S, N, D, Q, E, R or K; matrix=gonnet. Of the 138 residues that form the alignment, 73 (52.9%) are identical [indicated by *], 30 (21.74%) are strongly similar [:] and 12 (8.7%) are weakly similar [.].

FIG. 5 shows the DNA and amino acid sequence of Rs1 (SEQ ID NOs: 5 & 6).

FIG. 6 shows the alignment of Rs1 (SEQ ID NO: 6) with Japanin (SEQ ID NO: 8). The alignment of Rs1 with Japanin was obtained using clustalW with the following options: gap extension penalty=0.1; gap opening penalty=10.0; hydrophilic residues=G, P, S, N, D, Q, E, R or K; matrix=gonnet. Of the 131 residues that form the alignment, 105 (80.15%) are identical [indicated by *], 12 (9.16%) are strongly similar [:] and 7 (5.34%) are weakly similar [.].

FIG. 7 shows the alignment of RaA (SEQ ID NO: 2), RaB (SEQ ID NO: 4), Rs1 (SEQ ID NO: 6) and Japanin (SEQ ID NO: 8) and indicates the location of the conserved motifs and features. The CXXW (SEQ ID NO:33) motif is shown in italics, the conserved cysteine residues are shown in bold and the asparagine residue of the glycosylation site containing sequence is underlined. The following options were used: gap extension penalty=0.2; gap opening penalty=10.0; hydrophilic residues=G, P, S, N, D, Q, E, R or K; matrix=gonnet.

FIG. 8 shows the alignment of RaA (SEQ ID NO: 2), RaB (SEQ ID NO: 4), Rs1 (SEQ ID NO: 6), Japanin (SEQ ID NO: 8) and DA (SEQ ID NO: 10) and indicates the location of the conserved motifs and features. The CXXW SEQ ID NO:33) motif is shown in italics, the conserved cysteine residues are shown in bold and the asparagine residue of the glycosylation site containing sequence is underlined. The following options were used: gap extension penalty=0.2; gap opening penalty=10.0; hydrophilic residues=G, P, S, N, D, Q, E, R or K; matrix=gonnet.

DESCRIPTION OF THE SEQUENCES

Figure 9:
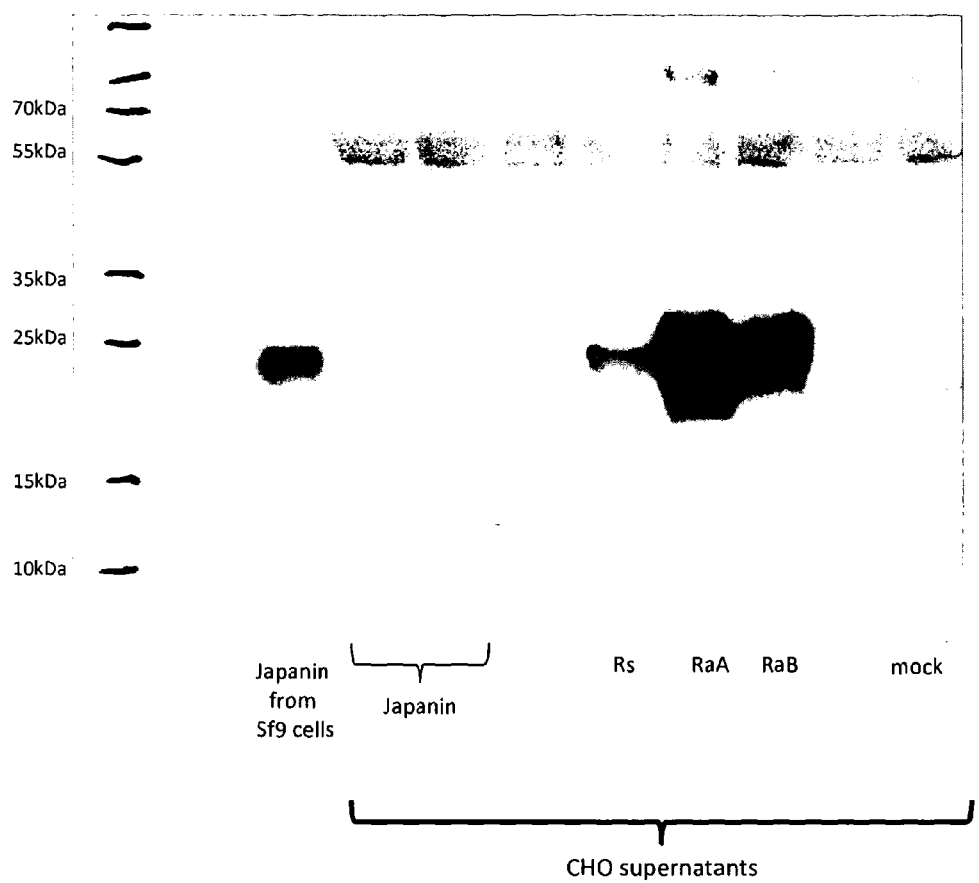
FIG. 9 shows Rs, RaA and RaB are present in CHO transfectant supernatants
Figure 10A:
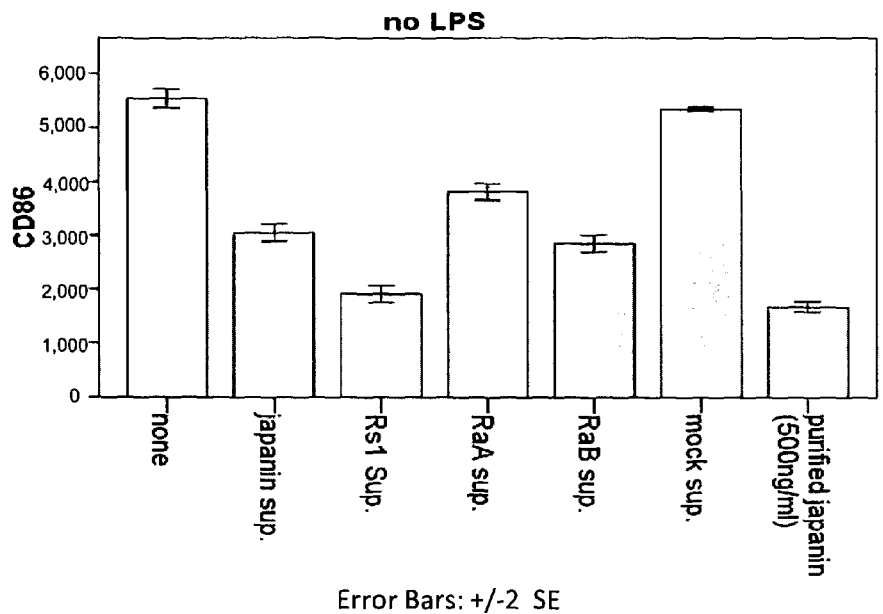
FIG. 10A shows the effect of Rs1, RaA and RaB transfectant supernatants on CD86 expression in dendritic cells that have not been treated with LPS.
Figure 10B:
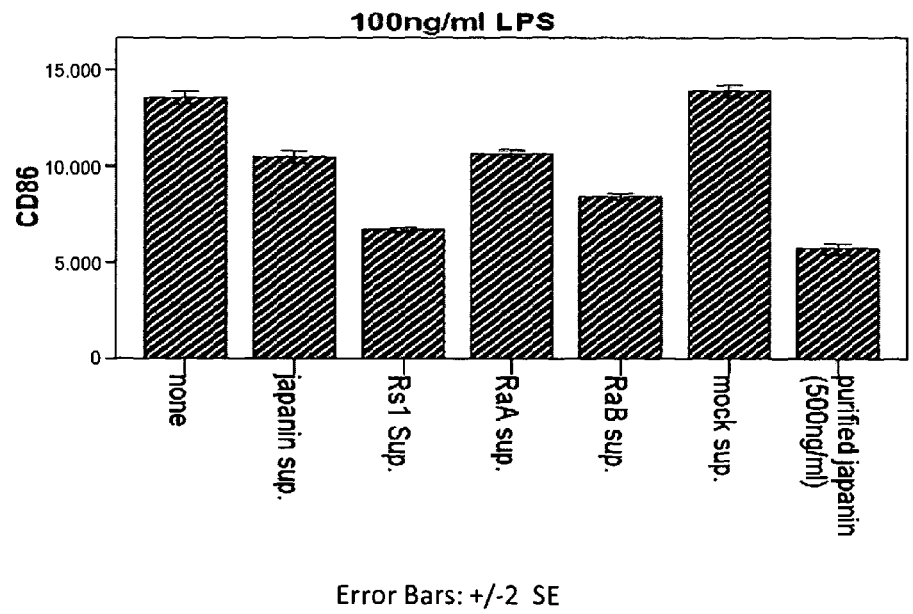
FIG. 10B shows that Rs1, RaA and RaB transfectant supernatants inhibit CD86 expression in LPS treated dendritic cells
Figure 11:
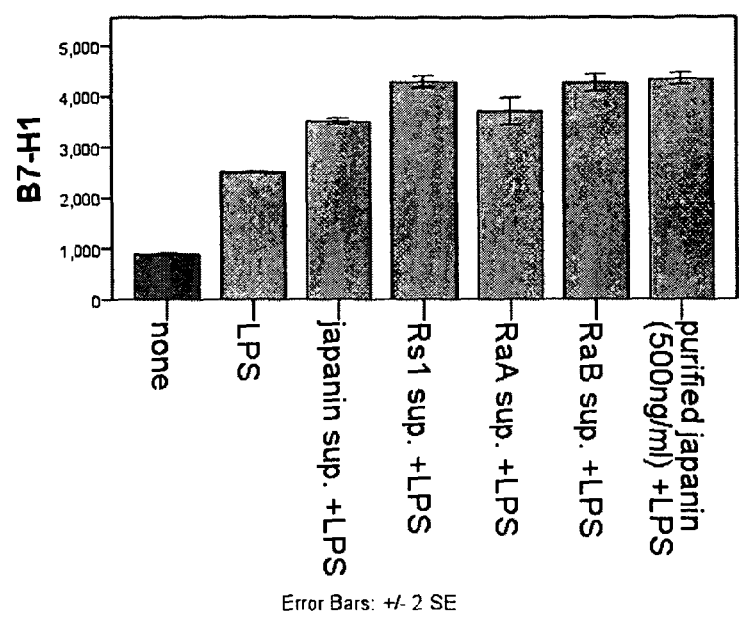
FIG. 11 shows the enhancement of B7-H1 upregulation in LPS treated dendritic cells in response to Rs1, RaA and RaB transfectant supernatants

SEQ ID NO: 1 is the nucleotide sequence of RaA
SEQ ID NO: 2 is the amino acid sequence of RaA
SEQ ID NO: 3 is the nucleotide sequence of RaB
SEQ ID NO: 4 is the amino acid sequence of RaB
SEQ ID NO: 5 is the nucleotide sequence of Rs1
SEQ ID NO: 6 is the amino acid sequence of Rs1
SEQ ID NO: 7 is the nucleotide sequence of Japanin
SEQ ID NO: 8 is the amino acid sequence of Japanin
SEQ ID NO: 9 is the nucleotide sequence of DA
SEQ ID NO: 10 is the amino acid sequence of DA
SEQ ID NO: 11 is the nucleotide sequence of RM
SEQ ID NO: 12 is the amino acid sequence of RM
SEQ ID NO: 13 is the nucleotide sequence of AM
SEQ ID NO: 14 is the amino acid sequence of AM
SEQ ID NO: 15 is the nucleotide sequence of RaC
SEQ ID NO: 16 is the amino acid sequence of RaC
SEQ ID NO: 17 is a degenerate Japanin-derived forward primer
SEQ ID NO: 18 is a vector specific reverse primer
SEQ ID NO: 19 is a Japanin-specific reverse primer
SEQ ID NO: 20 is a Rs1 specific reverse primer
SEQ ID NO: 21 is a RaA specific reverse primer
SEQ ID NO: 22 is a RaB specific reverse primer
SEQ ID NO: 23 is a vector specific forward primer
SEQ ID NO: 24 is the full amino acid sequence of Rs1
SEQ ID NO: 25 is the full length amino acid sequence of RaA
SEQ ID NO: 26 is the full length amino acid sequence of RaB
SEQ ID NO: 27 is the predicted mature peptide sequence of Rs1

SEQ ID NO: 28 is the predicted mature peptide sequence of RaA

SEQ ID NO: 29 is the predicted mature peptide sequence of RaB

SEQ ID NO: 30 is the nucleotide sequence of a Rs1 synthetic gene

SEQ ID NO: 31 is the nucleotide sequence of a RaA synthetic gene

SEQ ID NO: 32 is the nucleotide sequence of a RaB synthetic gene

SEQ ID NOs: 33-40 represent CXXW (SEQ ID NO:33) motifs

SEQ ID NO: 41 is Rs1 full length DNA/coding sequence (including the stop codon)

SEQ ID NO: 42 is RaA full length DNA/coding sequence (including the stop codon)

SEQ ID NO: 43 is RaB full length DNA/coding sequence (including the stop codon)

SEQ ID NO: 44 is a Rs1 5' DNA sequence

SEQ ID NO: 45 is a RaA 5' DNA sequence

SEQ ID NO: 46 is a RaB 5' DNA sequence

SEQ ID NO: 47 is a Rs1 specific forward primer

SEQ ID NO: 48 is a RaA specific forward primer

SEQ ID NO: 49 is a RaB specific forward primer

EXAMPLES

Example 1

Identification of RaA, RaB and Rs1

The incomplete amino acid sequence of the proteins RaA, RaB and Rs1, which are related to Japanin were obtained by amplifying *Rhipicephalus* cDNAs in expression libraries which were prepared in Lambda Zap II (Stratagene). Amplification was performed by means of the polymerase chain reaction (PCR) using a degenerate, Japanin-derived forward primer (SEQ ID NO: 17) in combination with either a vector specific reverse primer (SEQ ID NO: 18) in the case of RaB or a Japanin-specific reverse primer (SEQ ID NO: 19) in the case of RaA and Rs1.

Example 2

Alignment of Japanin with RaA, RaB and Rs1, Respectively

The amino acid sequences of RaA (SEQ ID NO: 2), RaB (SEQ ID NO: 4) and Rs1 (SEQ ID NO: 6) were each aligned with Japanin (SEQ ID NO: 8) using clustalW with the following options: gap extension penalty=0.1; gap opening penalty 10.0; hydrophilic hydrophilic residues=G, P, S, N, D, O, E, R or K; matrix=gonnet. The results of these alignments are shown in FIGS. 2, 4 and 6, respectively.

For RaA, of the 131 residues that form the alignment, 61 (46.56%) are identical, 26 (19.85%) are strongly similar and 22 (16.79%) are weakly similar.

For RaB, of the 138 residues that form the alignment, 73 (52.9%) are identical, 30 (21.74%) are strongly similar and 12 (8.7%) are weakly similar.

For Rs1, of the 131 residues that form the alignment, 105 (80.15%) are identical, 12 (9.16%) are strongly similar and 7 (5.34%) are weakly similar.

Example 3

Alignment of Japanin, RaA, RaB and Rs1

The amino acid sequences of RaA (SEQ ID NO: 2), RaB (SEQ ID NO: 4), Rs1 (SEQ ID NO: 6) and Japanin (SEQ ID NO: 8) were aligned using clustalW with the following options: gap extension penalty=0.2; gap opening penalty=10.0; hydrophilic residues=G, P, S, N, D, Q, E, R or K; matrix=gonnet. The result of this alignment is shown in FIG. 7.

Example 4

Alignment of Japanin, RaA, RaB, Rs1 and DA

The amino acid sequences of RaA (SEQ ID NO: 2), RaB (SEQ ID NO: 4), Rs1 (SEQ ID NO: 6), Japanin (SEQ ID NO: 8) and DA (SEQ ID NO: 10) were aligned using clustalW with the following options: gap extension penalty=0.2; gap opening penalty 10.0; hydrophilic residues=G, P, S, N, D, Q, E, R or K; matrix=gonnet. The result of this alignment is shown in FIG. 8.

FIG. 8 indicates that these five proteins form a distinct cluster within the tick lipocalin family. Their evolutionary relatedness and structural similarity suggest conserved functions.

The inventors have provided the amino acid and nucleotide sequences of three previously unidentified DC modulatory proteins. Based on sequence homology and alignment studies the inventors have been able to determine a number of motifs and features which may be important for the structure and function of such proteins. These results provide an insight into the workings of such molecules which is likely to be useful in designing further DC modulatory molecules for use in therapy.

The following general experimental techniques were employed for the experiments described in Examples 5-8:

Cell culture media and supplements were, unless otherwise stated, from PAA. LPS was atrichloroacetic acid-extracted preparation from *Escherichia coli* 055:B5 (Sigma, product code L4005). Human dendritic cells (DC) were generated from peripheral blood monocytes isolated from healthy adult donors. Briefly, Leucocyte cones (National Blood Service, Oxford) were mixed ~1:3 (v/v) with Ca2+/Mg2+-free Phosphate-buffered salt solution (PBS), carefully layered on to Lymphoprep (Axis Shield) and centrifuged at 800 g for 30 minutes (at 22° C.). The peripheral blood mononuclear cell (PBMC) layer formed at the interface between the PBS/Buffy coat mixture and Lymphoprep was carefully collected and washed three times with PBS to remove platelets (each time centrifuging for 10 minutes at 4° C., initially at 400 g, then 300 g, and finally 200 g).

Monocytes were isolated from PBMC by negative selection using the Easysep Human Monocyte Enrichment kit (Stemcell technologies). PBMC were resuspended in $Ca^{2+}$/$Mg^{2+}$-free PBS, and the kit was then used in accordance with the manufacturer's instructions. Purified monocytes were resuspended at $5 \times 10^5$/ml in DC-RPMI: RPMI 1640 supplemented with 10% fetal calf serum (FCS), 2 mM L-glutamine, 100 U/ml penicillin, 100 µg/ml streptomycin, 1000 U/ml human granulocyte macrophage colony-stimulating factor (GM-CSF) (Gentaur) and 250 ng/ml human interleukin 4 (IL-4) (Peprotech EC). After 3 days, one third of the media was removed and spun down, and the pellet resuspended in the same volume of fresh media containing 1000 U/ml GM-CSF and 750 ng/ml IL-4, then returned to the culture. After 5 days, the cells were either used immediately, or frozen. To freeze the cells, they were washed with HBSS/2% FCS, and resuspended in 5.5% hetastarch ("Voluven" from John Radcliffe Hospital pharmacy)/4.8% dimethyl sulfoxide (DMSO) (Hybrimax grade from Sigma)/

3.8% FCS in isotonic saline, then placing into a −80° C. freezer in a controlled freezing device (1° C./minute).

Example 5

PCR Cloning of 5' Sequence of Homologues

The missing N-terminal amino acid sequences of Rs1, RaA and RaB were obtained by amplifying cDNAs from the *Rhipicephalus* expression libraries which were used to obtain the partial sequences represented by SEQ ID NOs: 2, 4 and 6.

Amplification was performed by means of the polymerase chain reaction (PCR) using a gene-specific reverse primer (SEQ ID NOs: 20, 21 or 22) in combination with a vector specific forward primer (SEQ ID NO: 23), and employing the Phusion DNA polymerase (Finnzymes) in accordance with the manufacturer's instructions. PCR products were cloned into the pCR Blunt II TOPO cloning vector (Invitrogen) in accordance with the manufacturer's instructions, and ligated plasmid used to transform TOP10 *E. coli* cells (Invitrogen), which were then plated on to LB agar. Individual colonies were then picked for growth in liquid LB culture, and plasmid DNA prepared from them using the QIAprep system (Qiagen). Sequencing of these plasmids provided the 5' cDNA sequence of Rs1, RaA and RaB, (given in SEQ ID NOs: 44, 45 and 46 respectively).

Example 6

PCR Cloning of 3' Sequence of Homologues

The missing C-terminal amino acid sequences of Rs1 and RaA were obtained by amplifying cDNAs from the *Rhipicephalus* expression libraries which were used to obtain the partial sequences represented by SEQ ID NOs: 2, 4 and 6. The same approach was used to confirm the C-terminal sequence of RaB (previously determined; see example 1, SEQ ID NO:4).

Amplification was performed by means of the polymerase chain reaction (PCR) using a gene-specific forward primer (SEQ ID NOs: 47, 48 or 49) in combination with a vector specific reverse primer (SEQ ID NO: 23), and employing the Phusion DNA polymerase (Finnzymes) in accordance with the manufacturer's instructions. PCR products were cloned into the pT7Blue cloning vector using the Perfectly Blunt cloning kit (Novagen) in accordance with the manufacturer's instructions, and ligated plasmids used to transform TOP10 *E. coli* cells (Invitrogen), which were then plated on to LB agar. Individual colonies were picked for growth in liquid LB culture, and plasmid DNA prepared from them using the QIAprep system (Qiagen). Sequencing of these plasmids provided the 3' cDNA sequence of Rs1, RaA and RaB, and this was combined with the previously generated sequences to give full nucleotide cDNA sequences (represented by SEQ ID NOs: 41, 42 and 43 respectively), and thus the encoded peptide sequences (SEQ ID NOs: 24, 25 and 26 respectively). SignalP was used to identify likely signal peptide portions of the proteins, suggesting that the mature secreted proteins will have the amino acid sequences shown in SEQ ID NOs: 27, 28 and 29.

Example 7

Expression of Homologues in Chinese Hamster Ovary (CHO) Cells

In order to test the activity of the homologues, they were expressed in CHO cells. Synthetic genes encoding each of them were subcloned into a mammalian expression vector (pcDNA3.1), these expression constructs used to transfect CHO cells, and the presence of recombinant proteins in transfectant supernatants was confirmed by Western blotting.

a. Synthetic Genes

Synthetic genes optimised for CHO cell expression were generated by DNA2.0 (SEQ ID NOs: 30, 31 and 32). They encode the full peptide sequences of the homologues, as well as a C-terminal extension encoding a linker portion (GG) and a polyhistidine tag (HHHHHH; SEQ ID NO:73), to facilitate detection and purification. They also include non-coding DNA comprising a 5'-Kozak sequence (to allow eukaryotic expression), and restriction enzyme sites to facilitate subcloning: a 5' BamHI site and a 3' NotI site.

b. Subcloning into pcDNA3.1

As the synthetic genes were provided in a cloning vector, it was necessary to transfer them into an expression vector to produce recombinant protein. For expression in CHO cells, we selected the pcDNA3.1 mammalian expression vector, in which expression is driven by the i.e. CMV promoter.

pcDNA3.1 was prepared from parental pcDNA3.1-v5-his C (Invitrogen) by excising the multiple cloning region with BamHI and NotI restriction enyzmes (New England Biolabs), treating with FastAP alkaline phosphatase (Fermenatas) to reduce cell ligation of the vector, and gel purifying the vector backbone using the QIEx II system (Qiagen). Synthetic genes were prepared from their carrier plasmids by excising the homologue-encoding regions (including the Kozak sequence and polyhistidine tag) with BamHI and NotI restriction enyzmes, and gel purifying them using the QIEx II system. pDNA3.1-homologue constructs were generated by ligation of excised synthetic genes with prepared pDNA3.1 using T4 DNA Ligase (Fermentas). Ligated DNA was used to transform competent *E. coli* which were then plated on to LB agar to allow the selection of individual colonies for liquid culture. Plasmid DNA was extracted from these cultures using the QIAprepsystem (Qiagen), and its identity confirmed by sequencing. DNA incorporating the synthetic gene sequences was then used for transfection.

c. Transfection of CHO Cells

CHO cells were grown in RPMI supplemented with 10% FCS, 2 mM L-glutamine, 100 U/ml penicillin and 100 µg/ml streptomycin under standard cell culture conditions. For transfection, cells were seeded at an estimated 30-40% into 24 well plates, and cultured overnight. Wells with 80-95% confluency were then selected for transfection. Cells were transfected with pcDNA3.1-homologue constructs, pcDNA3.1-japanin-his (as a positive control), pcDNA3.1-lacZ-his (as a positive control for transfection and a negative control for DC-modulatory activity) or with the transfection reagent only (mock transfection control). Transfections were performed with the TransIT2020 reagent (Minis) in accordance with the manufacturer's instructions, using 1.5 µl of reagent and 500 ng of plasmid DNA per well. Supernatants were harvested after 72 hours, and either analysed or frozen immediately.

d. Western Blotting to Confirm Expression

Expression of polyhistidine-tagged proteins was confirmed by Western blotting. Lithium dodecyl sulphate (LDS) loading buffer (Invitrogen) was added 6.5 µl transfectant supernatant, along with dithiothreitol (DTT) (50 mM final concentration), and proteins denatured by heating to 70° C. for 10 minutes. Prepared samples were run on a 4-20% acrylamide Pierce Protein precast gel (Thermofisher), and then transferred to nitrocellulose membrane by wet transfer in Towbin buffer, with a constant current of 400 mA for one hour.

The membrane was blocked with StartingBlock T20 (PBS) Blocking Buffer (Thermofisher) for 30 minutes at room temperature, rinsed with PBS/0.1% Tween 20, and then incubated overnight at 6° C. in anti-pentahis-biotin (Qiagen) diluted 1/1000 in PBS/3% BSA/0.1% Tween 20. It was then washed extensively in PBS/0.1% Tween 20, and incubated for 30 minutes at room temperature in streptavidin-HRP (Jackson Immunoresearch) diluted 1/20000 in PBS/0.1% Tween 20. Further PBS/0.1% Tween 20 washes were then performed, and ECL substrate (GE Lifesciences) applied, prior to exposure of X-ray film to the membrane.

The developed film clearly reveals the presence of each polyhistine-tagged Japanin homologue in transfectant supernatant (see FIG. 9).

Example 8

Dendritic Cell Modulating Activity of Homologue Transfectant Supernatants a Inhibition of CD86 Upregulation in Response to Stimuli Screening for DC modulatory activity was performed using human monocyte-derived DC generated as previously described. DC were cultured in 96-well flat-bottomed tissue culture plates (Corning) in DC-RPMI supplemented with the samples to be screened. Transfectant supernatants were added to 10% of total volume, while purified japanin was used at 500 ng/ml. After 24 hours of culture LPS (100 ng/ml) were added to stimulate the DC. After another 18 to 24 hours of culture levels of CD86 expression were assessed by flow cytometry, following staining with anti-human CD86-PE, clone IT2.2 (eBioscience) at a 1/50 dilution. Flow cytometry was performed using a FACSCanto flow cytometer (Becton Dickinson). Supernatants from cells transfected with each of the three homologues were found to reduce CD86 expression in both LPS-treated and untreated DC, to an extent comparable to supernatant from japanin-transfectants (see FIG. 10).

b Enhancement of B7-H1 Upregulation in Response to Stimuli

DC were treated with transfectant supernatants and LPS as described in 4.1 above. Levels of B7-H1 (CD274) were then assessed by flow cytometry, following staining with anti-human B7H1-PECy7, clone MIH1 (eBioscience) at a 1/100 dilution. Flow cytometry was performed using a FACSCanto flow cytometer (Becton Dickinson). Supernatants from cells transfected with each of the three homologues, or with japanin, were found to enhance levels of B7-H1 expression over those induced by LPS alone (see FIG. 11).

This suggests that the homologues (and japanin) are driving the DC into a regulatory-type phenotype, reducing levels of (T cell costimulatory) CD86, while enhancing levels of (T cell "coinhibitory") B7-H1.

REFERENCES

Anguita, J., Ramamoorthi, N., Hovius, J., Das, S., Thomas, V., Persinski, R., Conze, D., Askenase, P., Rincon, M., Kantor, F., Fikrig, E. (2002) Salp15, an *Ixodes* scapularis salivary protein inhibits CD4+ T cell activation *Immunity* 16, 849-859.

Banchereau, J. et al. Ann N Y Acad Sci, 2003, 987, 180-187.

Bergman, D., Palmer, M., Caimano, M., Radolf, J., Wikel, S. (2000) Isolation and molecular cloning of a secreted immunosuppressant protein from *Dermacentor andersoni* salivary Gland *The Journal of Parasitology* 86(3), 516-525.

Cavassani, K., Aliberti, J., Dias, A., Silva, J., Ferreira, B. (2005) Tick saliva inhibits differentiation, maturation and function of murine bone-marrow-derived dendritic cells *Immunology* 114, 235-245.

Coligan et al., Current Protocols in Immunology 1(2): Chapter 5 (1991).

Figdor, C. G. et al. Nature medicine, 2004, 10 (5), 475-480.

Hannier, S., Liversidge, J., Sternberg, J., Bowman, A. (2004) Characterisation of the B-cell inhibitory protein factor in *Ixodes ricinus* tick saliva: a potential role in enhanced *Borrelia burgdoferi* transmission *Immunology* 113, 401-408.

Hovius, J., Ramamoorthi, N., Veer, C., Groot, K., Nijhof, A., Jongejan, F., Dam, A., Fikrig, E. (2007) Identification of Salp15 homologues in *Ixodes ricinus* ticks *Vector-bourne and Zoonotic Diseases* 7(3), 296-302.

Jaworski, D., Jasinskas, A., Metz, C., Bucala, R., Barbour, A. (2001) Identification and characterisation of a homologue of the pro-inflammatory cytokine Macrophage Migration Inhibitory Factor in the tick, *Amblyomma americanum Insect Molecular Biology* 10(4), 323-331.

Leboulle, G., Crippa, M., Decrem, Y., Mejri, N., Brossard, M., Bollen, A., Godfroid, E. (2002) Characterization of novel salivary immunosuppressive protein from *Ixodes ricinus* ticks *The Journal of Biological Chemistry* 88(12), 10083-10089.

Ribeiro J. M. C. (1995) Blood-feeding arthropods: live syringes or invertebrate pharmacologists? *Infectious Agents & Disease* 4, 143-152.

Sambrook, J. et al, (2000) Molecular Cloning, A Laboratory Manual, Cold Spring Harbor Laboratory Press, Cold Spring Harbor, N.Y.

Sa-Nunes, A., Bafica, A., Lucas, D., Conrads, T., Veenstra, T., Andersen, J., Mather, T., Ribeiro, J., Francischetti, I. (2007) Prostaglandin $E_2$ is a major inhibitor of dendritic cell maturation and function in *Ixodes* scapularis saliva *The journal of Immunology* 179, 1497-1505.

Skallova, A., Iezzi, G., Ampenberger, F., Kopf, M., Kopecky, J. (2008) Tick saliva inhibits dendritic cell migration, maturation, and function while promoting development of Th2 responses *Journal of Immunology* 180, 6186-6192.

Subklewe, N., Sebelin-Wulf, K., Beier, C., Lietz, A., Mathas, S., Dorken, B., Pezzutto, A. (2007) Dendritic cell maturation stage determines susceptibility to the proteasome inhibitor bortezomib. *Human Immunology* 68(3), 147-155.

Thompson, J. D., Higgins, D. G. and Gibson, T. J. (1994) CLUSTAL W: improving the sensitivity of progressive multiple sequence alignment through sequence weighting, positions-specific gap penalties and weight matrix choice. *Nucleic Acids Research,* 22, 4673-4680.

Yu, D., Liang, J., Yu, H., Wu, H., Xu, C., Lu, J., Lai, R. (2006) A tick B-cell inhibitory protein from salivary glands of the hard tick, *Hyalomma asiaticum asiaticum Biochemical and Biophysical research communications* 343, 585-590.

The invention claimed is:

1. A method of inhibiting the differentiation and/or maturation of dendritic cells comprising contacting said dendritic cells with a purified protein, wherein said protein comprises the amino acid sequence of SEQ ID NO:24 or SEQ ID NO:27.

2. The method of claim 1, wherein the protein is a recombinant protein.

3. The method of claim 1, wherein the protein is recovered from a cultured host cell.

4. A method of inhibiting the differentiation and/or maturation of dendritic cells in a human or an animal comprising administering to said human or animal a pharmaceutical composition comprising a pharmaceutically effective amount of an isolated protein comprising the amino acid sequence of SEQ ID NO:24 or SEQ ID NO:27.

* * * * *

UNITED STATES PATENT AND TRADEMARK OFFICE
CERTIFICATE OF CORRECTION

PATENT NO. : 9,676,832 B2  
APPLICATION NO. : 13/636469  
DATED : June 13, 2017  
INVENTOR(S) : Jonathan M. Austyn et al.

Page 1 of 1

It is certified that error appears in the above-identified patent and that said Letters Patent is hereby corrected as shown below:

On the Title Page

At item (75), change the inventor name from "Patricia Nuttal" to --Patricia Nuttall--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 73

<210> SEQ ID NO 1
<211> LENGTH: 390
<212> TYPE: DNA
<213> ORGANISM: Rhipicephalus appendiculatus
<220> FEATURE:
<223> OTHER INFORMATION: dendritic cell (DC) modulatory protein
      homologue RaA active fragment

<400> SEQUENCE: 1
ggacactcac gttcactgaa actaacgaac gttgcgtgcg taatatcgac ctacagaggc    60
caaaaggatg gatgggtcga gaggaatatg aattacgcct tttctgttgg aaaaccctgg   120
cgaggacagt cctcaactat tcatgtgcaa tggcgaccat atgctgcatt aatgaatgcg   180
aggacttcag atatcgtgag acatgatttg caaacaaagc cacagtacgt ggtacgaaat   240
tacgatgata actctttggt tctctcagac gtgaaagacg aatcgtcgcc atgctcactc   300
tgggtgacaa gaaagtatct ggataatatc ccagagacga caaacagaac attttatcac   360
caatgcccag aacctatcta cactactatt                                    390

<210> SEQ ID NO 2
<211> LENGTH: 130
<212> TYPE: PRT
<213> ORGANISM: Rhipicephalus appendiculatus
<220> FEATURE:
<223> OTHER INFORMATION: dendritic cell (DC) modulatory protein
      homologue RaA active fragment

<400> SEQUENCE: 2

Gly His Ser Arg Ser Leu Lys Leu Thr Asn Val Ala Cys Val Ile Ser
  1               5                  10                  15

Thr Tyr Arg Gly Gln Lys Asp Gly Trp Val Glu Arg Asn Met Asn Tyr
                 20                  25                  30

Ala Phe Ser Val Gly Lys Pro Trp Arg Gly Gln Ser Ser Thr Ile His
             35                  40                  45

Val Gln Trp Arg Pro Tyr Ala Ala Leu Met Asn Ala Arg Thr Ser Asp
         50                  55                  60

Ile Val Arg His Asp Leu Gln Thr Lys Pro Gln Tyr Val Val Arg Asn
 65                  70                  75                  80

Tyr Asp Asp Asn Ser Leu Val Leu Ser Asp Val Lys Asp Glu Ser Ser
                 85                  90                  95

Pro Cys Ser Leu Trp Val Thr Arg Lys Tyr Leu Asp Asn Ile Pro Glu
            100                 105                 110

Thr Thr Asn Arg Thr Phe Tyr His Gln Cys Pro Glu Pro Ile Tyr Thr
        115                 120                 125

Thr Ile
    130

<210> SEQ ID NO 3
<211> LENGTH: 420
<212> TYPE: DNA
<213> ORGANISM: Rhipicephalus appendiculatus
<220> FEATURE:
<223> OTHER INFORMATION: dendritic cell (DC) modulatory protein
      homologue RaB active fragment

<400> SEQUENCE: 3
ggatactcat ctaaaatgaa gataccaaac gttgtgtgca tcaactcaag atacttaagc    60
agcgaaggcg gctgggtgaa gaggagtgtg aattacatgt ttcccattga taaaccctgg   120

```
cgaggaaagt cctcaaccgt tgaagtgaaa tgggaaccat atgctgtatt actgcatatg      180
aagacttcat atgatgtgag ccgtgatttg caaacaaagt cgcaatacgt agtacggaat      240
tacgacgata actctttagt tctctcagac ctaaatgaag tatcatcatg ctcactctgg      300
gtgacaaagg agtatctgga taaaattcca gagacgacaa accgtacatt ttatcacctg      360
tgcccagatc ctgtctacac accgtttgat gagaactgtt atgtgaatta ataaaagcag      420
```

<210> SEQ ID NO 4
<211> LENGTH: 136
<212> TYPE: PRT
<213> ORGANISM: Rhipicephalus appendiculatus
<220> FEATURE:
<223> OTHER INFORMATION: dendritic cell (DC) modulatory protein
      homologue RaB active fragment

<400> SEQUENCE: 4

```
Gly Tyr Ser Ser Lys Met Lys Ile Pro Asn Val Val Cys Ile Asn Ser
 1               5                  10                  15

Arg Tyr Leu Ser Ser Glu Gly Gly Trp Val Lys Arg Ser Val Asn Tyr
            20                  25                  30

Met Phe Pro Ile Asp Lys Pro Trp Arg Gly Lys Ser Ser Thr Val Glu
        35                  40                  45

Val Lys Trp Glu Pro Tyr Ala Val Leu Leu His Met Lys Thr Ser Tyr
    50                  55                  60

Asp Val Ser Arg Asp Leu Gln Thr Lys Ser Gln Tyr Val Val Arg Asn
65                  70                  75                  80

Tyr Asp Asp Asn Ser Leu Val Leu Ser Asp Leu Asn Glu Val Ser Ser
                85                  90                  95

Cys Ser Leu Trp Val Thr Lys Glu Tyr Leu Asp Lys Ile Pro Glu Thr
            100                 105                 110

Thr Asn Arg Thr Phe Tyr His Leu Cys Pro Asp Pro Val Tyr Thr Pro
        115                 120                 125

Phe Asp Glu Asn Cys Tyr Val Asn
    130                 135
```

<210> SEQ ID NO 5
<211> LENGTH: 394
<212> TYPE: DNA
<213> ORGANISM: Rhipicephalus sp.
<220> FEATURE:
<223> OTHER INFORMATION: dendritic cell (DC) modulatory protein
      homologue Rs1 active fragment

<400> SEQUENCE: 5

```
gcatattcat cgaagctgtt ctcatggaat gtggggtgcg tcaaaacaag acacttaagc       60
caagaaggag attgggtgac aaggagtctg atttacgtgt ttaccttcga caaaaaaccc      120
tgggaaacaa aggccgatgc ttttaaagta aagtgggaac catattctcc actgctgcgt      180
gtgcaggctt cagattacgt gaaatataat ttgagggcga agccggaata ttttatacgg      240
acatacgacg acgactttt acttctatca gatgtgaaag agtcacgatc accatgctcg      300
ctctgggtga cactaaagta cgtggagaga attccagaga ctataaacag aacattttat      360
gcgaactgcc cagatcctgt caccgttcct tttg                                  394
```

<210> SEQ ID NO 6
<211> LENGTH: 131
<212> TYPE: PRT
<213> ORGANISM: Rhipicephalus sp.

```
<220> FEATURE:
<223> OTHER INFORMATION: dendritic cell (DC) modulatory protein
      homologue Rs1 active fragment

<400> SEQUENCE: 6

Ala Tyr Ser Ser Lys Leu Phe Ser Trp Asn Val Gly Cys Val Lys Thr
1               5                   10                  15

Arg His Leu Ser Gln Glu Gly Asp Trp Val Thr Arg Ser Leu Ile Tyr
            20                  25                  30

Val Phe Thr Phe Asp Lys Lys Pro Trp Glu Thr Lys Ala Asp Ala Phe
        35                  40                  45

Lys Val Lys Trp Glu Pro Tyr Ser Pro Leu Leu Arg Val Gln Ala Ser
    50                  55                  60

Asp Tyr Val Lys Tyr Asn Leu Arg Ala Lys Pro Glu Tyr Phe Ile Arg
65                  70                  75                  80

Thr Tyr Asp Asp Asp Phe Leu Leu Leu Ser Asp Val Lys Glu Ser Arg
                85                  90                  95

Ser Pro Cys Ser Leu Trp Val Thr Leu Lys Tyr Val Glu Arg Ile Pro
            100                 105                 110

Glu Thr Ile Asn Arg Thr Phe Tyr Ala Asn Cys Pro Asp Pro Val Thr
        115                 120                 125

Val Pro Phe
    130

<210> SEQ ID NO 7
<211> LENGTH: 531
<212> TYPE: DNA
<213> ORGANISM: Rhipicephalus appenticulatus
<220> FEATURE:
<223> OTHER INFORMATION: dendritic cell (DC) modulatory protein
      homologue Japanin active fragment

<400> SEQUENCE: 7
atgaaggtcc tgcgatgtct tgtttgctca ttttatataa ttgtatcttt gataaccacc      60
atgacaatcg gcaccccccag catgccggca atcaacacac agactctcta ccttgcggga    120
cactcatcga agctgttcga acgtaatgtg gggtgcgtca aaacaagata cttaaaccaa    180
acaggagatt gggtgacgag aagtctgatt tacgtattca cctttgacac agaaccttgg    240
gtaacacagg ccggtgcttt tcaagtaaag tgggaaccat attctccact gctgcgtgtg    300
aaggcttcag attacgtgag agataaatttg ggggcgaagc cggactactt tatacggaca    360
tacgacaacg acttttttact tctatcagat ttgaaagagg tacgatcaac atgctcgctc    420
tgggtgacac taaagtatgt ggacagaatt ccagagacta taaatagaac attttatacg    480
atctgcccag atcctgtccc cgttccttttt gacgagaggt gctatccata a             531

<210> SEQ ID NO 8
<211> LENGTH: 176
<212> TYPE: PRT
<213> ORGANISM: Rhipicephalus appendiculatus
<220> FEATURE:
<223> OTHER INFORMATION: dendritic cell (DC) modulatory protein
      homologue Japanin active fragment

<400> SEQUENCE: 8

Met Lys Val Leu Arg Cys Leu Val Cys Ser Phe Tyr Ile Ile Val Ser
1               5                   10                  15

Leu Ile Thr Thr Met Thr Ile Gly Thr Pro Ser Met Pro Ala Ile Asn
            20                  25                  30
```

Thr Gln Thr Leu Tyr Leu Ala Gly His Ser Ser Lys Leu Phe Glu Arg
        35                  40                  45

Asn Val Gly Cys Val Lys Thr Arg Tyr Leu Asn Gln Thr Gly Asp Trp
 50                  55                  60

Val Thr Arg Ser Leu Ile Tyr Val Phe Thr Phe Asp Thr Glu Pro Trp
 65                  70                  75                  80

Val Thr Gln Ala Gly Ala Phe Gln Val Lys Trp Glu Pro Tyr Ser Pro
                 85                  90                  95

Leu Leu Arg Val Lys Ala Ser Asp Tyr Val Arg Asp Asn Leu Gly Ala
                100                 105                 110

Lys Pro Asp Tyr Phe Ile Arg Thr Tyr Asp Asn Asp Phe Leu Leu Leu
            115                 120                 125

Ser Asp Leu Lys Glu Val Arg Ser Thr Cys Ser Leu Trp Val Thr Leu
        130                 135                 140

Lys Tyr Val Asp Arg Ile Pro Glu Thr Ile Asn Arg Thr Phe Tyr Thr
145                 150                 155                 160

Ile Cys Pro Asp Pro Val Pro Val Pro Phe Asp Glu Arg Cys Tyr Pro
                165                 170                 175

<210> SEQ ID NO 9
<211> LENGTH: 570
<212> TYPE: DNA
<213> ORGANISM: Dermacentor andersoni
<220> FEATURE:
<223> OTHER INFORMATION: dendritic cell (DC) modulatory protein
      homologue DA active fragment

<400> SEQUENCE: 9

```
atgaaactaa actttttgt gattcttgct gtgtacatta gcgtgtttgc catgacttac      60
gttgaaacat ctaacgaatc acctccgttt tatgagttac ctgcgaactc tactgatacc    120
ttgtatcttg ttggtcattc agtcgatctg tttcgctgga tgttaacatg cgttagaacg    180
aactatactt ctcgacaagg cgaagtggta aaccgcacac tgatttttaa ctactcgaaa    240
gagtttaacg agactccaga agagatgagc tttccttttc aagtgacggt gccagatgta    300
ccgataatgt ttgacttgga gttgaatgtg accgactcgt tagtaaacta tactggggca    360
caatccacgt accatattat ctactataac gacgaaagca tggtattggg agacaaaatg    420
cccacagtta gtgaaagggc catttgtagc ttgtgggtca aagaaaactt tacgctggaa    480
caccaaatcc cctttatggc taacttgagt tttcacacct cttgcaaaaa cgcgttgtat    540
tatggctacc tagacacgtg ttcgaaataa                                     570
```

<210> SEQ ID NO 10
<211> LENGTH: 172
<212> TYPE: PRT
<213> ORGANISM: Dermacentor andersoni
<220> FEATURE:
<223> OTHER INFORMATION: dendritic cell (DC) modulatory protein homologue DA active fragment

<400> SEQUENCE: 10

```
Met Thr Tyr Val Glu Thr Ser Asn Glu Ser Pro Pro Phe Tyr Glu Leu
 1               5                  10                  15

Pro Ala Asn Ser Thr Asp Thr Leu Tyr Leu Val Gly His Ser Val Asp
            20                  25                  30

Leu Phe Arg Trp Met Leu Thr Cys Val Arg Thr Asn Tyr Thr Ser Arg
        35                  40                  45

Gln Gly Glu Val Val Asn Arg Thr Leu Ile Phe Asn Tyr Ser Lys Glu
```

```
                    50                  55                  60
Phe Asn Glu Thr Pro Glu Met Ser Phe Pro Phe Gln Val Thr Val
 65                  70                  75                  80

Pro Asp Val Pro Ile Met Phe Asp Leu Glu Leu Asn Val Thr Asp Ser
                 85                  90                  95

Leu Val Asn Tyr Thr Gly Ala Gln Ser Thr Tyr His Ile Ile Tyr Tyr
                100                 105                 110

Asn Asp Glu Ser Met Val Leu Gly Asp Lys Met Pro Thr Val Ser Glu
            115                 120                 125

Arg Ala Ile Cys Ser Leu Trp Val Lys Glu Asn Phe Thr Leu Glu His
        130                 135                 140

Gln Ile Pro Phe Met Ala Asn Leu Ser Phe His Thr Ser Cys Lys Asn
145                 150                 155                 160

Ala Leu Tyr Tyr Gly Tyr Leu Asp Thr Cys Ser Lys
                165                 170

<210> SEQ ID NO 11
<211> LENGTH: 570
<212> TYPE: DNA
<213> ORGANISM: Rhipicephalus microplus
<220> FEATURE:
<223> OTHER INFORMATION: dendritic cell (DC) modulatory protein
      homologue RM active fragment

<400> SEQUENCE: 11
ggtgaaaagc caggcccttc ttatccgcag gaaaaataga ggcccgagaa tggagccctg      60
cggaacacca gatgccaccg gagctgaagg agaagctgtg ccatcaatga ctacacattg    120
ccgccttgac gagaggactc tcaacaagtc agagtactca tgcgtggctt ctagctacaa    180
ggaaattggg ggaggattta tccaccgcac acttctcctg aaaagggcac cgacaccagg    240
agagtactgg gacacgcaaa tacccccttca aatacaagct accatgtgct atatgacaat    300
gaacttgact ttatcctgtc cgctgataaa gctcggtgca aaggaacagt atctgatgtt    360
tcgtcagacg tggaattaca tgctgctgac cgaattgata gagttaaagg aacgaccact    420
gtgttctatt tgggcgaaga aggactttgc aagaaaaagt aaggtggacg aatatacatt    480
gacattattt cacgcaattt gcaaagatgc agtctacgac gggtacccag agtattgccc    540
gatacttgtg aaataaaacc catttccttt                                      570

<210> SEQ ID NO 12
<211> LENGTH: 168
<212> TYPE: PRT
<213> ORGANISM: Rhipicephalus microplus
<220> FEATURE:
<223> OTHER INFORMATION: dendritic cell (DC) modulatory protein
      homologue RM active fragment

<400> SEQUENCE: 12

Met Glu Pro Cys Gly Thr Pro Asp Ala Thr Gly Ala Glu Gly Glu Ala
  1               5                  10                  15

Val Pro Ser Met Thr Thr His Cys Arg Leu Asp Glu Arg Thr Leu Asn
             20                  25                  30

Lys Ser Glu Tyr Ser Cys Val Ala Ser Ser Tyr Lys Glu Ile Gly Gly
         35                  40                  45

Gly Phe Ile His Arg Thr Leu Leu Lys Arg Ala Pro Thr Pro Gly
     50                  55                  60

Glu Tyr Trp Asp Thr Gln Ile Pro Leu Gln Ile Gln Ala Thr Met Cys
 65                  70                  75                  80
```

-continued

```
Tyr Met Thr Met Asn Leu Thr Leu Ser Cys Pro Leu Ile Lys Leu Gly
                85                  90                  95

Ala Lys Glu Gln Tyr Leu Met Phe Arg Gln Thr Trp Asn Tyr Met Leu
            100                 105                 110

Leu Thr Glu Leu Ile Glu Leu Lys Glu Arg Pro Leu Cys Ser Ile Trp
        115                 120                 125

Ala Lys Lys Asp Phe Ala Arg Lys Ser Lys Val Asp Glu Tyr Thr Leu
    130                 135                 140

Thr Leu Phe His Ala Ile Cys Lys Asp Ala Val Tyr Asp Gly Tyr Pro
145                 150                 155                 160

Glu Tyr Cys Pro Ile Leu Val Lys
                165
```

```
<210> SEQ ID NO 13
<211> LENGTH: 696
<212> TYPE: DNA
<213> ORGANISM: Amblyomma americanum
<220> FEATURE:
<223> OTHER INFORMATION: dendritic cell (DC) modulatory protein
      homologue AM active fragment

<400> SEQUENCE: 13
gggccctgga aaagtgtctc caaaatgcaa aggcacggat aaatgcctgt gttatgatgg     60
gtatttccgc aagacagata cagaatgcgt ccttctgaaa agagactgcc tggatagaaa    120
atatgattcg gacgggcttt tggcagcgac ggaagacatc tacatggtga aaagttcgga    180
aacgctgaaa atggattttc ccacaaaatg tctcagatct gcattcctat cgtcgaccgg    240
taatgtaatt cgtcgcacaa tccagtacag agagaacatt ggagaacctc aggacgtgtg    300
gctgacaaag aatttcactg ttatacttaa aaaagacaaa gacacactga cggttcaaaa    360
cactgaaaca ctgaaccgtt tgacccgggc aggtaaatct cagtacagga ttgtgcattc    420
tggtggtgac tgtttgatat tgggagacca aattcccctt ggaggacaaa caacgacatg    480
cactatgtgg gtcaagcaga gctctattgg acagacgttt tctgaggagt gcgaattctt    540
ttttaaacac tactgcgcca catcgagctt gactgtgaaa gatacacggt gtgactaaca    600
cttgagcgcc caggcacgcc accgaatctg ctttcttacc accaaggaag acaatagcag    660
gctgcattca ttgcgttcca tccatctctt atatgg                              696
```

```
<210> SEQ ID NO 14
<211> LENGTH: 144
<212> TYPE: PRT
<213> ORGANISM: Amblyomma americanum
<220> FEATURE:
<223> OTHER INFORMATION: dendritic cell (DC) modulatory protein
      homologue AM active fragment

<400> SEQUENCE: 14

Met Val Lys Ser Ser Glu Thr Leu Lys Met Asp Phe Pro Thr Lys Cys
 1               5                  10                  15

Leu Arg Ser Ala Phe Leu Ser Ser Thr Gly Asn Val Ile Arg Arg Thr
            20                  25                  30

Ile Gln Tyr Arg Glu Asn Ile Gly Glu Pro Gln Asp Val Trp Leu Thr
        35                  40                  45

Lys Asn Phe Thr Val Ile Leu Lys Lys Asp Lys Asp Thr Leu Thr Val
    50                  55                  60

Gln Asn Thr Glu Thr Leu Asn Arg Leu Thr Arg Ala Gly Lys Ser Gln
65                  70                  75                  80
```

Tyr Arg Ile Val His Ser Gly Gly Asp Cys Leu Ile Leu Gly Asp Gln
            85                  90                  95

Ile Pro Leu Gly Gly Gln Thr Thr Thr Cys Thr Met Trp Val Lys Gln
        100                 105                 110

Ser Ser Ile Gly Gln Thr Phe Ser Glu Glu Cys Glu Phe Phe Phe Lys
        115                 120                 125

His Tyr Cys Ala Thr Ser Ser Leu Thr Val Lys Asp Thr Arg Cys Asp
    130                 135                 140

<210> SEQ ID NO 15
<211> LENGTH: 748
<212> TYPE: DNA
<213> ORGANISM: Rhipicephalus appendiculatus
<220> FEATURE:
<223> OTHER INFORMATION: dendritic cell (DC) modulatory protein
      homologue RaC active fragment

<400> SEQUENCE: 15

```
atggcaactt tgacagctct tatattttcg gtgcttgccg taccaataac ttccattgat      60
attcaccaat ttgtccaaga cacaattctg acaccttatc aagatccttg gaagtttatt    120
gcaaatcaca gcactgttta cctctcacgt gtatccatag caccttcgct tgaagataaa    180
ccacaatttc cttgtgtacg ttcacggtat tggagtaaat caggagaaag cgtgaaccgg    240
tcactcgaca tttataatac aacgaacgaa ggggattaca ggtccacaaa cattgatctt    300
aaggtaaaac acgagaaaag ccgcacaatt cttgatgttg acgtggaagg gggaacatct    360
tctataatga gcattcctta tatgaagaca tctagcgcgt cgaatctaac aggatacaca    420
ttccttgtac tgtatagtga ccataattgt cttattctag ccgaaacgct tcaaacagca    480
acaataaaaa aaattacctt cgctgctgga tgtggcttcc acaaagtcgt atacaaaagc    540
tacagaaatg ttgccagttc atttacacac tcctgtgcct acgtgccgct gaagatgttg    600
aagtatttca gccctcatgc cttactaata cgaccaaagc aagccattga tctggcggag    660
atcctgggac accgcctggt aactgatatg ggattttttt tgctgtttta tgatgtttcc    720
gtccatgaat aaagattttt tgtgaaag                                       748
```

<210> SEQ ID NO 16
<211> LENGTH: 224
<212> TYPE: PRT
<213> ORGANISM: Rhipicephalus appendiculatus
<220> FEATURE:
<223> OTHER INFORMATION: dendritic cell (DC) modulatory protein
      homologue RaC active fragment

<400> SEQUENCE: 16

Ile Asp Ile His Gln Phe Val Gln Asp Thr Ile Leu Thr Pro Tyr Gln
1               5                   10                  15

Asp Pro Trp Lys Phe Ile Ala Asn His Ser Thr Val Tyr Leu Ser Arg
            20                  25                  30

Val Ser Ile Ala Pro Ser Leu Glu Asp Lys Pro Gln Phe Pro Cys Val
        35                  40                  45

Arg Ser Arg Tyr Trp Ser Lys Ser Gly Glu Ser Val Asn Arg Ser Leu
    50                  55                  60

Asp Ile Tyr Asn Thr Thr Asn Glu Gly Asp Tyr Arg Ser Thr Asn Ile
65                  70                  75                  80

Asp Leu Lys Val Lys His Glu Lys Ser Arg Thr Ile Leu Asp Val Asp
                85                  90                  95

Val Glu Gly Gly Thr Ser Ser Ile Met Ser Ile Pro Tyr Met Lys Thr
            100                 105                 110

Ser Ser Ala Ser Asn Leu Thr Gly Tyr Thr Phe Leu Val Leu Tyr Ser
        115                 120                 125

Asp His Asn Cys Leu Ile Leu Ala Glu Thr Leu Gln Thr Ala Thr Ile
    130                 135                 140

Lys Lys Ile Thr Phe Ala Ala Gly Cys Gly Phe His Lys Val Val Tyr
145                 150                 155                 160

Lys Ser Tyr Arg Asn Val Ala Ser Ser Phe Thr His Ser Cys Ala Tyr
                165                 170                 175

Val Pro Leu Lys Met Leu Lys Tyr Phe Ser Pro His Ala Leu Leu Ile
            180                 185                 190

Arg Pro Lys Gln Ala Ile Asp Leu Ala Glu Ile Leu Gly His Arg Leu
        195                 200                 205

Val Thr Asp Met Gly Phe Phe Leu Leu Phe Tyr Asp Val Ser Val His
    210                 215                 220

<210> SEQ ID NO 17
<211> LENGTH: 21
<212> TYPE: DNA
<213> ORGANISM: Artificial Sequence
<220> FEATURE:
<223> OTHER INFORMATION: synthetic degenerate Japanin-derived PCR
      amplification forward primer

<400> SEQUENCE: 17
acmsakacyc tytacctygy g                                          21

<210> SEQ ID NO 18
<211> LENGTH: 18
<212> TYPE: DNA
<213> ORGANISM: Artificial Sequence
<220> FEATURE:
<223> OTHER INFORMATION: synthetic vector specific PCR amplification
      reverse primer

<400> SEQUENCE: 18
ttatgctgag tgataccc                                              18

<210> SEQ ID NO 19
<211> LENGTH: 32
<212> TYPE: DNA
<213> ORGANISM: Artificial Sequence
<220> FEATURE:
<223> OTHER INFORMATION: synthetic Japanin-specific PCR amplification
      reverse primer

<400> SEQUENCE: 19
atatgcggcc gcttatggat agcacctctc gt                              32

<210> SEQ ID NO 20
<211> LENGTH: 26
<212> TYPE: DNA
<213> ORGANISM: Artificial Sequence
<220> FEATURE:
<223> OTHER INFORMATION: synthetic Rs1 specific PCR amplification
      reverse primer

<400> SEQUENCE: 20
catgagaaca gcttcgatga atatgc                                     26

<210> SEQ ID NO 21
<211> LENGTH: 27

-continued

```
<212> TYPE: DNA
<213> ORGANISM: Artificial Sequence
<220> FEATURE:
<223> OTHER INFORMATION: synthetic RaA specific PCR amplification
      reverse primer

<400> SEQUENCE: 21
cgttagtttc agtgaacgtg agtgtcc                                          27

<210> SEQ ID NO 22
<211> LENGTH: 31
<212> TYPE: DNA
<213> ORGANISM: Artificial Sequence
<220> FEATURE:
<223> OTHER INFORMATION: synthetic RaB specific PCR amplification
      reverse primer

<400> SEQUENCE: 22
cgtttggtat cttcattta gatgagtatc c                                      31

<210> SEQ ID NO 23
<211> LENGTH: 26
<212> TYPE: DNA
<213> ORGANISM: Artificial Sequence
<220> FEATURE:
<223> OTHER INFORMATION: synthetic vector specific PCR amplification
      forward primer, vector specific PCR amplification
      reverse primer

<400> SEQUENCE: 23
cgcaattaac cctcactaaa gggaac                                           26

<210> SEQ ID NO 24
<211> LENGTH: 176
<212> TYPE: PRT
<213> ORGANISM: Rhipicephalus sp.
<220> FEATURE:
<223> OTHER INFORMATION: dendritic cell (DC) modulatory protein
      homologue full-length Rs1

<400> SEQUENCE: 24
```

Met Lys Val Leu Leu Cys Leu Val Cys Ser Phe Tyr Ile Ile Val Ser
 1               5                  10                  15

Ser Ile Thr Thr Met Thr Thr Gly Thr Pro Ser Met Pro Ala Ile Asn
            20                  25                  30

Arg Gln Thr Leu Tyr Leu Ala Ala Tyr Ser Ser Lys Leu Phe Ser Trp
        35                  40                  45

Asn Val Gly Cys Val Lys Thr Arg His Leu Ser Gln Glu Gly Asp Trp
    50                  55                  60

Val Thr Arg Ser Leu Ile Tyr Val Phe Thr Phe Asp Lys Lys Pro Trp
65                  70                  75                  80

Glu Thr Lys Ala Asp Ala Phe Lys Val Lys Trp Glu Pro Tyr Ser Pro
                85                  90                  95

Leu Leu Arg Val Gln Ala Ser Asp Tyr Val Lys Tyr Asn Leu Arg Ala
            100                 105                 110

Lys Pro Glu Tyr Phe Ile Arg Thr Tyr Asp Asp Phe Leu Leu Leu
        115                 120                 125

Ser Asp Val Lys Glu Ser Arg Ser Pro Cys Ser Leu Trp Val Thr Leu
    130                 135                 140

Lys Tyr Val Glu Arg Ile Pro Glu Thr Ile Asn Arg Thr Phe Tyr Ala
145                 150                 155                 160

Asn Cys Pro Asp Pro Val Thr Val Pro Phe Asp Glu Arg Cys Tyr Pro

```
                    165                 170                 175

<210> SEQ ID NO 25
<211> LENGTH: 177
<212> TYPE: PRT
<213> ORGANISM: Rhipicephalus appendiculatus
<220> FEATURE:
<223> OTHER INFORMATION: dendritic cell (DC) modulatory protein
      homologue full-length RaA

<400> SEQUENCE: 25

Met Gln Leu Pro Leu Ser His Leu Leu Ala Cys Tyr Ile Leu Ala Ser
1               5                   10                  15

Ser Ile Pro Ser Trp Thr Thr Ser Thr Pro Ile Met Pro Ala Ile Asn
            20                  25                  30

Lys Glu Thr Leu Tyr Leu Val Gly His Ser Arg Ser Leu Lys Leu Thr
        35                  40                  45

Asn Val Ala Cys Val Ile Ser Thr Tyr Arg Gly Gln Lys Asp Gly Trp
    50                  55                  60

Val Glu Arg Asn Met Asn Tyr Ala Phe Ser Val Gly Lys Pro Trp Arg
65                  70                  75                  80

Gly Gln Ser Ser Thr Ile His Val Gln Trp Arg Pro Tyr Ala Ala Leu
                85                  90                  95

Met Asn Ala Arg Thr Ser Asp Ile Val Arg His Asp Leu Gln Thr Lys
            100                 105                 110

Pro Gln Tyr Val Val Arg Asn Tyr Asp Asp Asn Ser Leu Val Leu Ser
        115                 120                 125

Asp Val Lys Asp Glu Ser Ser Pro Cys Ser Leu Trp Val Thr Arg Lys
    130                 135                 140

Tyr Leu Asp Asn Ile Pro Glu Thr Thr Asn Arg Thr Phe Tyr His Gln
145                 150                 155                 160

Cys Pro Glu Pro Ile Tyr Thr Thr Ile Asp Glu Lys Cys Phe Glu Asn
                165                 170                 175

Lys

<210> SEQ ID NO 26
<211> LENGTH: 175
<212> TYPE: PRT
<213> ORGANISM: Rhipicephalus appendiculatus
<220> FEATURE:
<223> OTHER INFORMATION: dendritic cell (DC) modulatory protein
      homologue full-length RaB

<400> SEQUENCE: 26

Met Lys Leu Leu Leu Ser Gly Met Leu Ala Gly Tyr Ile Leu Ala Ser
1               5                   10                  15

Ser Ile Leu Ser Met Thr Thr Gly Thr Pro Arg Met Pro Ala Ile Ser
            20                  25                  30

Arg Glu Thr Leu His Leu Val Gly Tyr Ser Ser Lys Met Lys Ile Pro
        35                  40                  45

Asn Val Val Cys Ile Asn Ser Arg Tyr Leu Ser Ser Glu Gly Gly Trp
    50                  55                  60

Val Lys Arg Ser Val Asn Tyr Met Phe Pro Ile Asp Lys Pro Trp Arg
65                  70                  75                  80

Gly Lys Ser Ser Thr Val Glu Val Lys Trp Glu Pro Tyr Ala Val Leu
                85                  90                  95

Leu His Met Lys Thr Ser Tyr Asp Val Ser Arg Asp Leu Gln Thr Lys
            100                 105                 110
```

-continued

Ser Gln Tyr Val Val Arg Asn Tyr Asp Asp Asn Ser Leu Val Leu Ser
            115                 120                 125

Asp Leu Asn Glu Val Ser Ser Cys Ser Leu Trp Val Thr Lys Glu Tyr
130                 135                 140

Leu Asp Lys Ile Pro Glu Thr Thr Asn Arg Thr Phe Tyr His Leu Cys
145                 150                 155                 160

Pro Asp Pro Val Tyr Thr Pro Phe Asp Glu Asn Cys Tyr Val Asn
                165                 170                 175

<210> SEQ ID NO 27
<211> LENGTH: 152
<212> TYPE: PRT
<213> ORGANISM: Rhipicephalus sp.
<220> FEATURE:
<223> OTHER INFORMATION: dendritic cell (DC) modulatory protein
      homologue predicted mature Rs1

<400> SEQUENCE: 27

Thr Pro Ser Met Pro Ala Ile Asn Arg Gln Thr Leu Tyr Leu Ala Ala
1               5                   10                  15

Tyr Ser Ser Lys Leu Phe Ser Trp Asn Val Gly Cys Val Lys Thr Arg
            20                  25                  30

His Leu Ser Gln Glu Gly Asp Trp Val Thr Arg Ser Leu Ile Tyr Val
        35                  40                  45

Phe Thr Phe Asp Lys Lys Pro Trp Glu Thr Lys Ala Asp Ala Phe Lys
    50                  55                  60

Val Lys Trp Glu Pro Tyr Ser Pro Leu Leu Arg Val Gln Ala Ser Asp
65                  70                  75                  80

Tyr Val Lys Tyr Asn Leu Arg Ala Lys Pro Glu Tyr Phe Ile Arg Thr
                85                  90                  95

Tyr Asp Asp Asp Phe Leu Leu Leu Ser Asp Val Lys Glu Ser Arg Ser
            100                 105                 110

Pro Cys Ser Leu Trp Val Thr Leu Lys Tyr Val Glu Arg Ile Pro Glu
        115                 120                 125

Thr Ile Asn Arg Thr Phe Tyr Ala Asn Cys Pro Asp Pro Val Thr Val
    130                 135                 140

Pro Phe Asp Glu Arg Cys Tyr Pro
145                 150

<210> SEQ ID NO 28
<211> LENGTH: 153
<212> TYPE: PRT
<213> ORGANISM: Rhipicephalus sp.
<220> FEATURE:
<223> OTHER INFORMATION: dendritic cell (DC) modulatory protein
      homologue predicted mature RaA

<400> SEQUENCE: 28

Thr Pro Ile Met Pro Ala Ile Asn Lys Glu Thr Leu Tyr Leu Val Gly
1               5                   10                  15

His Ser Arg Ser Leu Lys Leu Thr Asn Val Ala Cys Val Ile Ser Thr
            20                  25                  30

Tyr Arg Gly Gln Lys Asp Gly Trp Val Glu Arg Asn Met Asn Tyr Ala
        35                  40                  45

Phe Ser Val Gly Lys Pro Trp Arg Gly Gln Ser Ser Thr Ile His Val
    50                  55                  60

Gln Trp Arg Pro Tyr Ala Ala Leu Met Asn Ala Arg Thr Ser Asp Ile
65                  70                  75                  80

```
Val Arg His Asp Leu Gln Thr Lys Pro Gln Tyr Val Arg Asn Tyr
            85                  90                  95

Asp Asp Asn Ser Leu Val Leu Ser Asp Val Lys Asp Glu Ser Ser Pro
            100                 105                 110

Cys Ser Leu Trp Val Thr Arg Lys Tyr Leu Asp Asn Ile Pro Glu Thr
            115                 120                 125

Thr Asn Arg Thr Phe Tyr His Gln Cys Pro Glu Pro Ile Tyr Thr Thr
        130                 135                 140

Ile Asp Glu Lys Cys Phe Glu Asn Lys
145                 150
```

```
<210> SEQ ID NO 29
<211> LENGTH: 151
<212> TYPE: PRT
<213> ORGANISM: Rhipicephalus sp.
<220> FEATURE:
<223> OTHER INFORMATION: dendritic cell (DC) modulatory protein
      homologue predicted mature RaB

<400> SEQUENCE: 29
```

```
Thr Pro Arg Met Pro Ala Ile Ser Arg Glu Thr Leu His Leu Val Gly
1               5                   10                  15

Tyr Ser Ser Lys Met Lys Ile Pro Asn Val Val Cys Ile Asn Ser Arg
            20                  25                  30

Tyr Leu Ser Ser Glu Gly Gly Trp Val Lys Arg Ser Val Asn Tyr Met
            35                  40                  45

Phe Pro Ile Asp Lys Pro Trp Arg Gly Lys Ser Thr Val Glu Val
    50                  55                  60

Lys Trp Glu Pro Tyr Ala Val Leu Leu His Met Lys Thr Ser Tyr Asp
65                  70                  75                  80

Val Ser Arg Asp Leu Gln Thr Lys Ser Gln Tyr Val Val Arg Asn Tyr
            85                  90                  95

Asp Asp Asn Ser Leu Val Leu Ser Asp Leu Asn Glu Val Ser Ser Cys
            100                 105                 110

Ser Leu Trp Val Thr Lys Glu Tyr Leu Asp Lys Ile Pro Glu Thr Thr
            115                 120                 125

Asn Arg Thr Phe Tyr His Leu Cys Pro Asp Pro Val Tyr Thr Pro Phe
        130                 135                 140

Asp Glu Asn Cys Tyr Val Asn
145                 150
```

```
<210> SEQ ID NO 30
<211> LENGTH: 572
<212> TYPE: DNA
<213> ORGANISM: Artificial Sequence
<220> FEATURE:
<223> OTHER INFORMATION: synthetic Rs1 gene optimized for CHO cell
      expression

<400> SEQUENCE: 30
ggatccacca tgaaggtgtt gctctgtttg gtctgttcgt tctacatcat tgtctcctca      60
attaccacga tgacaacggg cacaccgtcc atgccggcaa tcaatcgaca dacgctgtac    120
ttggctgcgt attcatccaa gctgtttagc tggaacgtcg ggtgcgtcaa aacgcggcac    180
ttgtcacaag aaggagactg gtaactcgc tcgcttatct acgtgttcac atttgacaaa    240
aagccttggg aaactaaagc ggacgcgttc aaggtgaagt gggaaccta ctcgccgctt     300 cttagagtgc aggccagcga ctatgtaaag tacaacctca gagccaagcc cgagtatttc     360
```

```
atcaggacgt atgacgatga tttcctcctt ctctcggatg tgaaagagag cagatcaccc    420
tgtagcctct gggtaaccct gaaatacgta aacgcatcc  ctgagacaat caacaggact    480
ttctatgcaa attgccctga cccggtgacc gtgccatttg atgagcggtg ctaccccggt    540
gggcaccacc atcatcacca ctaagcggcc gc                                  572
```

<210> SEQ ID NO 31
<211> LENGTH: 575
<212> TYPE: DNA
<213> ORGANISM: Artificial Sequence
<220> FEATURE:
<223> OTHER INFORMATION: synthetic RaA gene optimized for CHO cell
      expression

<400> SEQUENCE: 31

```
ggatccacca tgcaactgcc cctttcacac ctcctggcct gctacattct cgcgtcatcg     60
atcccctcgt ggacgaccag cacaccgatt atgccggcga tcaacaagga gacattgtat    120
ttggtaggcc actcgaggag ccttaagctc actaacgtcg cgtgtgtcat ctcaacttac    180
agaggacaga aagatggatg ggtggagcgg aacatgaact atgctttctc cgtggggaag    240
ccttggcgag acagtcaag  caccatccat gtacagtgga ggccgtatgc cgcgctgatg    300
aacgcacgga catccgatat cgtgagacac gaccttcaaa ctaaaccgca gtatgtcgta    360
cggaattacg atgacaattc gttggtgctg tccgacgtca aggatgagtc atcgccttgc    420
tccctctggg tgacgcgcaa atacttggac aacatccccg agacaacgaa taggacgttc    480
taccaccagt gtccggaacc aatctacacg accattgacg aaaagtgctt tgaaaacaaa    540
gggggtcacc accatcatca ccattaagcg gccgc                               575
```

<210> SEQ ID NO 32
<211> LENGTH: 569
<212> TYPE: DNA
<213> ORGANISM: Artificial Sequence
<220> FEATURE:
<223> OTHER INFORMATION: synthetic RaB gene optimized for CHO cell
      expression

<400> SEQUENCE: 32

```
ggatccacca tgaagttgtt gctgagcgga atgttggcgg ggtacatcct cgcatcctca     60
atcctttcga tgacaaccgg taccccgagg atgccggcga tttcgagaga aacgctgcat    120
ctcgtggggt actccagcaa gatgaagatc cccaacgtgg tctgtatcaa ctcacgctac    180
ctgtcatcgg agggcggatg ggtgaaacga tccgtgaatt acatgttccc aattgataaa    240
ccttggagag ggaaatcgtc aactgtagaa gtcaaatggg agccgtatgc cgtgctcctc    300
cacatgaaaa catcgtatga cgtgtcgagg gacttgcaga ctaagagcca gtacgtcgta    360
cgcaattacg acgataactc acttgtgctc agcgatctta acgaagtatc atcctgctcg    420
ctctgggtca caaagagta tctggataag atcccagaga caacgaaccg gacgttctat    480
catttgtgtc ccgaccctgt gtatacgccc tttgacgaga attgctacgt caatggagga    540
caccatcacc accaccatta agcggccgc                                      569
```

<210> SEQ ID NO 33
<211> LENGTH: 4
<212> TYPE: PRT
<213> ORGANISM: Artificial Sequence
<220> FEATURE:
<223> OTHER INFORMATION: synthetic dendritic cell (DC) modulatory
      protein homologue conserved motif

```
<220> FEATURE:
<221> NAME/KEY: VARIANT
<222> LOCATION: (2)...(3)
<223> OTHER INFORMATION: Xaa = any amino acid

<400> SEQUENCE: 33

Cys Xaa Xaa Trp
 1

<210> SEQ ID NO 34
<211> LENGTH: 4
<212> TYPE: PRT
<213> ORGANISM: Artificial Sequence
<220> FEATURE:
<223> OTHER INFORMATION: synthetic dendritic cell (DC) modulatory
      protein homologue conserved motif
<220> FEATURE:
<221> NAME/KEY: VARIANT
<222> LOCATION: (2)...(2)
<223> OTHER INFORMATION: Xaa = any amino acid

<400> SEQUENCE: 34

Cys Xaa Leu Trp
 1

<210> SEQ ID NO 35
<211> LENGTH: 4
<212> TYPE: PRT
<213> ORGANISM: Artificial Sequence
<220> FEATURE:
<223> OTHER INFORMATION: synthetic dendritic cell (DC) modulatory
      protein homologue conserved motif

<400> SEQUENCE: 35

Cys Ser Leu Trp
 1

<210> SEQ ID NO 36
<211> LENGTH: 4
<212> TYPE: PRT
<213> ORGANISM: Artificial Sequence
<220> FEATURE:
<223> OTHER INFORMATION: synthet -continued

```
<220> FEATURE:
<223> OTHER INFORMATION: synthetic dendritic cell (DC) modulatory
      protein homolog

<400> SEQUENCE: 42

```
atgcagcttc ctctatctca cctgctcgct tgttatatac ttgcatcttc catcccctca    60
tggacgacta gcaccccat catgcctgca atcaacaagg agactcttta ccttgtggga   120
cactcacgtt cactgaaact aacgaacgtt gcgtgcgtaa tatcgaccta cagaggccaa   180
aaggatggat gggtcgagag gaatatgaat tacgcctttt ctgttggaaa accctggcga   240
ggacagtcct caactattca tgtgcaatgg cgaccatatg ctgcattaat gaatgcgagg   300
acttcagata tcgtgagaca tgatttgcaa acaaagccac agtacgtggt acgaaattac   360
gatgataact ctttggttct ctcagacgtg aaagacgaat cgtcgccatg ctcactctgg   420
gtgacaagaa agtatctgga taatatccca gagacgacaa acagaacatt ttatcaccaa   480
tgcccagaac ctatctacac tactattgat gagaagtgct ttgaaaacaa ataa         534
```

<210> SEQ ID NO 43
<211> LENGTH: 528
<212> TYPE: DNA
<213> ORGANISM: Rhipicephalus appendiculatus
<220> FEATURE:
<223> OTHER INFORMATION: dendritic cell (DC) modulatory protein homologue full-length RaB coding sequence

<400> SEQUENCE: 43

```
atgaagctcc ttctgtctgg catgctcgca ggttatatac ttgcatcttc catcctttcc    60
atgacaaccg gcacccccag aatgccagca atcagcagag agactcttca ccttgtggga   120
tactcatcta aaatgaagat accaaacgtt gtgtgcatca actcaagata cttaagcagc   180
gaaggcggct gggtgaagag gagtgtgaat tacatgtttc ccattgataa accctggcga   240
ggaaagtcct caaccgttga agtgaaatgg gaaccatatg ctgtattact gcatatgaag   300
acttcatatg atgtgagccg tgatttgcaa acaaagtcgc aatacgtagt acggaattac   360
gacgataact ctttagttct ctcagaccta aatgaagtat catcatgctc actctgggtg   420
acaaggagt atctggataa aattccagag acgacaaacc gtacattta tcacctgtgc   480
ccagatcctg tctacacacc gtttgatgag aactgttatg tgaattaa                528
```

<210> SEQ ID NO 44
<211> LENGTH: 153
<212> TYPE: DNA
<213> ORGANISM: Rhipicephalus sp.
<220> FEATURE:
<223> OTHER INFORMATION: dendritic cell (DC) modulatory protein homologue Rs1 5' DNA sequence

<400> SEQUENCE: 44

```
tcagaaaaaa atgaaggtcc tgctatgtct tgtttgctca ttttatataa ttgtatcttc    60
gataacaacc atgacaaccg gcacccccag catgccggca atcaacagac agactctcta   120
cctcgcggca tattcatcga agctgttctc atg                                 153
```

<210> SEQ ID NO 45
<211> LENGTH: 276
<212> TYPE: DNA
<213> ORGANISM: Rhipicephalus appendiculatus
<220> FEATURE:
<223> OTHER INFORMATION: dendritic cell (DC) modulatory protein homologue RaA 5' DNA sequence

<400> SEQUENCE: 45

```
tgggaagagt gcaaggactc gtggctgaaa gatcgcataa ccattttca gagagtaagt    60
```

```
tgactattgc aagtgaattt gctaaacgaa tcaagtttcc ctcaccggag tgtcaagagt    120
tttcactact tgatgcagct tcctctatct cacctgctcg cttgttatat acttgcatct    180
tccatcccct catggacgac tagcacccccc atcatgcctg caatcaacaa ggagactctt    240
taccttgtgg gacactcacg ttcactgaaa ctaacg                              276
```

<210> SEQ ID NO 46
<211> LENGTH: 290
<212> TYPE: DNA
<213> ORGANISM: Rhipicephalus appendiculatus
<220> FEATURE:
<223> OTHER INFORMATION: dendritic cell (DC) modulatory protein
      homologue RaB 5' DNA sequence

<400> SEQUENCE: 46

```
aattcggcac gaggaaaagg gcaaggactc gtggctgaaa gatcgcataa ccattctcgt     60
gagagttagt tgacaatttc aagtcaattt gctaaacgaa tcaagtttct ctcaccagag    120
tgccaagagc tgtaaccatt tgatgaagct ccttctgtct ggcatgctcg caggttatat    180
acttgcatct tccatccttt ccatgacaac cggcacccccc agaatgccag caatcagcag    240
agagactctt caccttgtgg gatactcatc taaaatgaag ataccaaacg                290
```

<210> SEQ ID NO 47
<211> LENGTH: 20
<212> TYPE: DNA
<213> ORGANISM: Artificial Sequence
<220> FEATURE:
<223> OTHER INFORMATION: synthetic Rs1 specific PCR amplification
      forward primer

<400> SEQUENCE: 47

```
ctgggaaaca aaggccgatg                                                 20
```

<210> SEQ ID NO 48
<211> LENGTH: 25
<212> TYPE: DNA
<213> ORGANISM: Artificial Sequence
<220> FEATURE:
<223> OTHER INFORMATION: synthetic RaA specific PCR amplification
      forward primer

<400> SEQUENCE: 48

```
cgaggacagt cctcaactat tcatg                                           25
```

<210> SEQ ID NO 49
<211> LENGTH: 22
<212> TYPE: DNA
<213> ORGANISM: Artificial Sequence
<220> FEATURE:
<223> OTHER INFORMATION: synthetic RaB specific PCR amplification
      forward primer

<400> SEQUENCE: 49

```
cgaggaaagt cctcaaccgt tg                                              22
```

<210> SEQ ID NO 50
<211> LENGTH: 9
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (2)...(2)

<223> OTHER INFORMATION: Xaa = any amino acid except Pro
<221> NAME/KEY: VARIANT
<222> LOCATION: (3)...(3)
<223> OTHER INFORMATION: Xaa = Ser or Thr
<220> FEATURE:
<221> NAME/KEY: VARIANT
<222> LOCATION: (4)...(6)
<223> OTHER INFORMATION: Xaa = any amino acid
<220> FEATURE:
<221> NAME/KEY: VARIANT
<222> LOCATION: (7)...(8)
<223> OTHER INFORMATION: Xaa = any amino acid, may be present or absent

<400> SEQUENCE: 50

Asn Xaa Xaa Xaa Xaa Xaa Xaa Xaa Cys
 1               5

<210> SEQ ID NO 51
<211> LENGTH: 25
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (1)...(12)
<223> OTHER INFORMATION: Xaa = any amino acid
<220> FEATURE:
<221> NAME/KEY: VARIANT
<222> LOCATION: (13)...(16)
<223> OTHER INFORMATION: Xaa = any amino acid, may be present or absent
<220> FEATURE:
<221> NAME/KEY: VARIANT
<222> LOCATION: (18)...(18)
<223> OTHER INFORMATION: Xaa = any amino acid except Pro
<220> FEATURE:
<221> NAME/KEY: VARIANT
<222> LOCATION: (19)...(19)
<223> OTHER INFORMATION: Xaa = Ser or Thr
<220> FEATURE:
<221> NAME/KEY: VARIANT
<222> LOCATION: (20)...(22)
<223> OTHER INFORMATION: Xaa = any amino acid
<220> FEATURE:
<221> NAME/KEY: VARIANT
<222> LOCATION: (23)...(24)
<223> OTHER INFORMATION: Xaa = any amino acid, may be present or absent

<400> SEQUENCE: 51

Xaa Xaa Xaa Xaa Xaa Xaa Xaa Xaa Xaa Xaa Xaa Xaa Xaa Xaa Xaa
 1               5                  10                  15

Asn Xaa Xaa Xaa Xaa Xaa Xaa Xaa Cys
            20                  25

<210> SEQ ID NO 52
<211> LENGTH: 26
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (2)...(13)
<223> OTHER INFORMATION: Xaa = any amino acid
<220> FEATURE:
<221> NAME/KEY: VARIANT
<222> LOCATION: (14)...(17)
<223> OTHER INFORMATION: Xaa = any amino acid, may be present or absent
<220> FEATURE:
<221> NAME/KEY: VARIANT
<222> LOCATION: (19)...(19)
<223> OTHER INFORMATION: Xaa = any amino acid except Pro

```
<220> FEATURE:
<220> FEATURE:
<221> NAME/KEY: VARIANT
<222> LOCATION: (20)...(20)
<223> OTHER INFORMATION: Xaa = Ser or Thr
<220> FEATURE:
<221> NAME/KEY: VARIANT
<222> LOCATION: (21)...(23)
<223> OTHER INFORMATION: Xaa = any amino acid
<220> FEATURE:
<221> NAME/KEY: VARIANT
<222> LOCATION: (24)...(25)
<223> OTHER INFORMATION: Xaa = any amino acid, may be preset or absent

<400> SEQUENCE: 52

Trp Xaa Xaa Xaa Xaa Xaa Xaa Xaa Xaa Xaa Xaa Xaa Xaa Xaa Xaa
 1               5                  10                  15

Xaa Asn Xaa Xaa Xaa Xaa Xaa Xaa Xaa Cys
            20                  25

<210> SEQ ID NO 53
<211> LENGTH: 29
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (5)...(16)
<223> OTHER INFORMATION: Xaa = any amino acid
<220> FEATURE:
<221> NAME/KEY: VARIANT
<222> LOCATION: (17)...(20)
<223> OTHER INFORMATION: Xaa = any amino acid, may be present or absent
<220> FEATURE:
<221> NAME/KEY: VARIANT
<222> LOCATION: (22)...(22)
<223> OTHER INFORMATION: Xaa = any amino acid except Pro
<220> FEATURE:
<221> NAME/KEY: VARIANT
<222> LOCATION: (23)...(23)
<223> OTHER INFORMATION: Xaa = Ser or Thr
<220> FEATURE:
<221> NAME/KEY: VARIANT
<222> LOCATION: (24)...(26)
<223> OTHER INFORMATION: Xaa = any amino acid
<220> FEATURE:
<221> NAME/KEY: VARIANT
<222> LOCATION: (27)...(28)
<223> OTHER INFORMATION: Xaa = any amino acid, may be present or absent

<400> SEQUENCE: 53

Cys Xaa Xaa Trp Xaa Xaa Xaa Xaa Xaa Xaa Xaa Xaa Xaa Xaa Xaa
 1               5                  10                  15

Xaa Xaa Xaa Xaa Asn Xaa Xaa Xaa Xaa Xaa Xaa Xaa Cys
            20                  25

<210> SEQ ID NO 54
<211> LENGTH: 29
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (2)...(3)
<223> OTHER INFORMATION: Xaa = any amino acid
<220> FEATURE:
```

```
<221> NAME/KEY: VARIANT
<222> LOCATION: (5)...(16)
<223> OTHER INFORMATION: Xaa = any amino acid
<220> FEATURE:
<221> NAME/KEY: VARIANT
<222> LOCATION: (17)...(20)
<223> OTHER INFORMATION: Xaa = any amino acid, may be present or absent
<220> FEATURE:
<221> NAME/KEY: VARIANT
<222> LOCATION: (22)...(22)
<223> OTHER INFORMATION: Xaa = any amino acid except Pro
<220> FEATURE:
<221> NAME/KEY: VARIANT
<222> LOCATION: (23)...(23)
<223> OTHER INFORMATION: Xaa = Ser or Thr
<220> FEATURE:
<221> NAME/KEY: VARIANT
<222> LOCATION: (24)...(24)
<223> OTHER INFORMATION: Xaa = Phe orTyr
<220> FEATURE:
<221> NAME/KEY: VARIANT
<222> LOCATION: (25)...(26)
<223> OTHER INFORMATION: Xaa = any amino acid
<220> FEATURE:
<221> NAME/KEY: VARIANT
<222> LOCATION: (27)...(28)
<223> OTHER INFORMATION: Xaa = any amino acid, may be present or absent

<400> SEQUENCE: 54

Cys Xaa Xaa Trp Xaa Xaa Xaa Xaa Xaa Xaa Xaa Xaa Xaa Xaa Xaa Xaa
1               5                   10                  15

Xaa Xaa Xaa Xaa Asn Xaa Xaa Xaa Xaa Xaa Xaa Xaa Cys
            20                  25

<210> SEQ ID NO 55
<211> LENGTH: 29
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (5)...(11)
<223> OTHER INFORMATION: Xaa = any amino acid
<220> FEATURE:
<221> NAME/KEY: VARIANT
<222> LOCATION: (12)...(15)
<223> OTHER INFORMATION: Xaa = any amino acid, may be present or absent
<220> FEATURE:
<221> NAME/KEY: VARIANT
<222> LOCATION: (16)...(16)
<223> OTHER INFORMATION: Xaa = Ile or Leu
<220> FEATURE:
<221> NAME/KEY: VARIANT
<222> LOCATION: (18)...(20)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid except Pro
<220> FEATURE:
<221> NAME/KEY: VARIANT
<222> LOCATION: (23)...(23)
<223> OTHER INFORMATION: Xaa = Ser or Thr
<220> FEATURE:
<221> NAME/KEY: VARIANT
<222> LOCATION: (24)...(26)
<223> OTHER INFORMATION: Xaa = any amino acid
<220> FEATURE:
<221> NAME/KEY: VARIANT
<222> LOCATION: (27)...(28)
```

<223> OTHER INFORMATION: Xaa = any amino acid, may be present or absent

<400> SEQUENCE: 55

Cys Xaa Xaa Trp Xaa Xaa Xaa Xaa Xaa Xaa Xaa Xaa Xaa Xaa Xaa Xaa
1               5                   10                  15

Pro Xaa Xaa Xaa Asn Xaa Xaa Xaa Xaa Xaa Xaa Xaa Cys
            20                  25

<210> SEQ ID NO 56
<211> LENGTH: 29
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (5)...(11)
<223> OTHER INFORMATION: Xaa = any amino acid
<220> FEATURE:
<221> NAME/KEY: VARIANT
<222> LOCATION: (12)...(15)
<223> OTHER INFORMATION: Xaa = any amino acid, may be present or absent
<220> FEATURE:
<221> NAME/KEY: VARIANT
<222> LOCATION: (18)...(20)
<223> OTHER INFORMATION: Xaa = any amino acid
<220> FEATURE:
<221> NAME/KEY: VARIANT
<222> LOCATION: (22)...(22)
<223> OTHER INFORMATION: Xaa = any amino acid except Pro
<220> FEATURE:
<221> NAME/KEY: VARIANT
<222> LOCATION: (23)...(23)
<223> OTHER INFORMATION: Xaa = Ser or Thr
<220> FEATURE:
<221> NAME/KEY: VARIANT
<222> LOCATION: (24)...(24)
<223> OTHER INFORMATION: Xaa = Phe or Tyr
<220> FEATURE:
<221> NAME/KEY: VARIANT
<222> LOCATION: (25)...(26)
<223> OTHER INFORMATION: Xaa = any amino acid
<220> FEATURE:
<221> NAME/KEY: VARIANT
<222> LOCATION: (27)...(28)
<223> OTHER INFORMATION: Xaa = any amino acid, may be present or absent

<400> SEQUENCE: 56

Cys Xaa Xaa Trp Xaa Xaa Xaa Xaa Xaa Xaa Xaa Xaa Xaa Xaa Xaa Xaa
1               5                   10                  15

Pro Xaa Xaa Xaa Asn Xaa Xaa Xaa Xaa Xaa Xaa Xaa Cys
            20                  25

<210> SEQ ID NO 57
<211> LENGTH: 27
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence
<220> FEATURE:
<221> NAME/KEY: VARIANT
<222> LOCATION: (2)...(3)
<223> OTHER INFORMATION: Xaa = any amino acid
<220> FEATURE:
<221> NAME/KEY: VARIANT
<222> LOCATION: (5)...(17)
<223> OTHER INFORMATION: Xaa = any amino acid -continued

```
<220> FEATURE:
<221> NAME/KEY: VARIANT
<222> LOCATION: (18)...(19)
<223> OTHER INFORMATION: Xaa = any amino acid, may be present or absent
<220> FEATURE:
<221> NAME/KEY: VARIANT
<222> LOCATION: (21)...(21)
<223> OTHER INFORMATION: Xaa = any amino acid except Pro
<220> FEATURE:
<221> NAME/KEY: VARIANT
<222> LOCATION: (22)...(22)
<223> OTHER INFORMATION: Xaa = Ser or Thr
<220> FEATURE:
<221> NAME/KEY: VARIANT
<222> LOCATION: (23)...(26)
<223> OTHER INFORMATION: Xaa = any amino acid

<400> SEQUENCE: 57

Cys Xaa Xaa Trp Xaa Xaa Xaa Xaa Xaa Xaa Xaa Xaa Xaa Xaa Xaa
 1               5                  10                  15

Xaa Xaa Xaa Asn Xaa Xaa Xaa Xaa Xaa Xaa Cys
            20                  25

<210> SEQ ID NO 58
<211> LENGTH: 134
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(93)
<223> OTHER INFORMATION: Xaa = any amino acid, may be present or absent
<220> FEATURE:
<221> NAME/KEY: VARIANT
<222> LOCATION: (95)...(116)
<223> OTHER INFORMATION: Xaa = any amino acid
<220> FEATURE:
<221> NAME/KEY: VARIANT
<222> LOCATION: (117)...(120)
<223> OTHER INFORMATION: Xaa = any amino acid, may be present or absent
<220> FEATURE:
<221> NAME/KEY: VARIANT
<222> LOCATION: (122)...(131)
<223> OTHER INFORMATION: Xaa = any amino acid
<220> FEATURE:
<221> NAME/KEY: VARIANT
<222> LOCATION: (132)...(133)
<223> OTHER INFORMATION: Xaa = any amino acid, may be present or absent

<400> SEQUENCE: 58

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
 65                 70                  75                  80

Xaa Xaa Xaa Xaa Xaa Xaa Xaa Xaa Xaa Xaa Xaa Xaa Cys Xaa Xaa
                85                  90                  95
```

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Cys Xaa Xaa Xaa Xaa Xaa Xaa
        115                 120                 125

Xaa Xaa Xaa Xaa Xaa Cys
    130

<210> SEQ ID NO 59
<211> LENGTH: 133
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(92)
<223> OTHER INFORMATION: Xaa = any amino acid, may be present or absent
<220> FEATURE:
<221> NAME/KEY: VARIANT
<222> LOCATION: (94)...(115)
<223> OTHER INFORMATION: Xaa = any amino acid
<220> FEATURE:
<221> NAME/KEY: VARIANT
<222> LOCATION: (116)...(119)
<223> OTHER INFORMATION: Xaa = any amino acid, may be present or absent
<220> FEATURE:
<221> NAME/KEY: VARIANT
<222> LOCATION: (121)...(130)
<223> OTHER INFORMATION: Xaa = any amino acid
<220> FEATURE:
<221> NAME/KEY: VARIANT
<222> LOCATION: (131)...(132)
<223> OTHER INFORMATION: Xaa = any amino acid, may be present or absent

<400> SEQUENCE: 59

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Cys Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Cys Xaa Xaa Xaa Xaa Xaa Xaa Xaa Xaa
        115                 120                 125

Xaa Xaa Xaa Xaa Cys
    130

<210> SEQ ID NO 60
<211> LENGTH: 134
<212> TYPE: PRT
<213> ORGANISM: Artificial Sequence
<220> FEATURE:
<223> OTHER INFORMATION: synthetic dendritic cell (DC) modulatory protein homologue lipocalin fold conserved Cys distribution
pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(93)
<223> OTHER INFORMATION: Xaa = any amino acid, may be present or
      absent
<220> FEATURE:
<221> NAME/KEY: VARIANT
<222> LOCATION: (95)...(116)
<223> OTHER INFORMATION: Xaa = any amino acid
<220> FEATURE:
<221> NAME/KEY: VARIANT
<222> LOCATION: (117)...(120)
<223> OTHER INFORMATION: Xaa = any amino acid, may be present or absent
<220> FEATURE:
<221> NAME/KEY: VARIANT
<222> LOCATION: (122)...(131)
<223> OTHER INFORMATION: Xaa = any amino acid
<220> FEATURE:
<221> NAME/KEY: VARIANT
<222> LOCATION: (132)...(133)
<223> OTHER INFORMATION: Xaa = any amino acid, may be present or absent

<400> SEQUENCE: 60

Cys Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
                50                  55                  60

Xaa Xaa Xaa Xaa Xaa Xaa Xaa Xaa Xaa Xaa Xaa Xaa Xaa Xaa Xaa
 65                 70                  75                  80

Xaa Xaa Xaa Xaa Xaa Xaa Xaa Xaa Xaa Xaa Xaa Xaa Cys Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Cys Xaa Xaa Xaa Xaa Xaa Xaa Xaa
        115                 120                 125

Xaa Xaa Xaa Xaa Xaa Cys
        130

<210> SEQ ID NO 61
<211> LENGTH: 134
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(93)
<223> OTHER INFORMATION: Xaa = any amino acid, may be present or absent
<220> FEATURE:
<221> NAME/KEY: VARIANT
<222> LOCATION: (95)...(117)
<223> OTHER INFORMATION: Xaa = any amino acid
<220> FEATURE:

<221> NAME/KEY: VARIANT
<222> LOCATION: (118)...(120)
<223> OTHER INFORMATION: Xaa = any amino acid, may be present or absent
<220> FEATURE:
<221> NAME/KEY: VARIANT
<222> LOCATION: (121)...(131)
<223> OTHER INFORMATION: Xaa = any amino acid
<220> FEATURE:
<221> NAME/KEY: VARIANT
<222> LOCATION: (132)...(133)
<223> OTHER INFORMATION: Xaa = any amino acid, may be present or absent

<400> SEQUENCE: 61

```
Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa
            50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Xaa
                85                  90                  95

Xaa Xaa Xaa Xaa Xaa Xaa Xaa Xaa Xaa Xaa Xaa Xaa Xaa Xaa Xaa
                100                 105                 110

Xaa Xaa Xaa Xaa Xaa Xaa Xaa Xaa Cys Xaa Xaa Xaa Xaa Xaa Xaa
        115                 120                 125

Xaa Xaa Xaa Xaa Xaa Cys
    130
```

<210> SEQ ID NO 62
<211> LENGTH: 134
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(92)
<223> OTHER INFORMATION: Xaa = any amino acid, may be present or absent
<220> FEATURE:
<221> NAME/KEY: VARIANT
<222> LOCATION: (94)...(115)
<223> OTHER INFORMATION: Xaa = any amino acid
<220> FEATURE:
<221> NAME/KEY: VARIANT
<222> LOCATION: (116)...(120)
<223> OTHER INFORMATION: Xaa = any amino acid, may be present or absent
<220> FEATURE:
<221> NAME/KEY: VARIANT
<222> LOCATION: (122)...(131)
<223> OTHER INFORMATION: Xaa = any amino acid
<220> FEATURE:
<221> NAME/KEY: VARIANT
<222> LOCATION: (132)...(133)
<223> OTHER INFORMATION: Xaa = any amino acid, may be present or absent

<400> SEQUENCE: 62

```
Cys Xaa Xaa Xaa Xaa Xaa Xaa Xaa Xaa Xaa Xaa Xaa Xaa Xaa Xaa
 1               5                  10                  15
```

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Cys Xaa Xaa Xaa
            85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Cys Xaa Xaa Xaa Xaa Xaa Xaa
        115                 120                 125

Xaa Xaa Xaa Xaa Xaa Cys
        130

<210> SEQ ID NO 63
<211> LENGTH: 135
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(93)
<223> OTHER INFORMATION: Xaa = any amino acid, may be present or absent
<220> FEATURE:
<221> NAME/KEY: VARIANT
<222> LOCATION: (95)...(117)
<223> OTHER INFORMATION: Xaa = any amino acid
<220> FEATURE:
<221> NAME/KEY: VARIANT
<222> LOCATION: (118)...(121)
<223> OTHER INFORMATION: Xaa = any amino acid, may be present or absent
<220> FEATURE:
<221> NAME/KEY: VARIANT
<222> LOCATION: (123)...(132)
<223> OTHER INFORMATION: Xaa = any amino acid
<220> FEATURE:
<221> NAME/KEY: VARIANT
<222> LOCATION: (133)...(134)
<223> OTHER INFORMATION: Xaa = any amino acid, may be present or absent

<400> SEQUENCE: 63

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Xaa
            85                  90                  95

```
Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Cys Xaa Xaa Xaa Xaa Xaa
    115                 120                 125

Xaa Xaa Xaa Xaa Xaa Xaa Cys
    130                 135

<210> SEQ ID NO 64
<211> LENGTH: 134
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(93)
<223> OTHER INFORMATION: Xaa = any amino acid, may be present or absent
<220> FEATURE:
<221> NAME/KEY: VARIANT
<222> LOCATION: (95)...(116)
<223> OTHER INFORMATION: Xaa = any amino acid
<220> FEATURE:
<221> NAME/KEY: VARIANT
<222> LOCATION: (117)...(120)
<223> OTHER INFORMATION: Xaa = any amino acid, may be present or absent
<220> FEATURE:
<221> NAME/KEY: VARIANT
<222> LOCATION: (122)...(131)
<223> OTHER INFORMATION: Xaa = any amino acid
<220> FEATURE:
<221> NAME/KEY: VARIANT
<222> LOCATION: (132)...(133)
<223> OTHER INFORMATION: Xaa = any amino acid, may be present or absent

<400> SEQUENCE: 64

Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Cys Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Cys Xaa Xaa Xaa Xaa Xaa Xaa
    115                 120                 125

Xaa Xaa Xaa Xaa Xaa Cys
    130

<210> SEQ ID NO 65
<211> LENGTH: 134
<212> TYPE: PRT
<213> ORGANISM: Artificial Sequence
<220> FEATURE:
<223> OTHER INFORMATION: synthetic dendritic cell (DC) modulatory
``` protein homologue lipocalin fold conserved Cys distribution
pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(92)
<223> OTHER INFORMATION: Xaa = any amino acid, may be present or absent
<220> FEATURE:
<221> NAME/KEY: VARIANT
<222> LOCATION: (94)...(115)
<223> OTHER INFORMATION: Xaa = any amino acid
<220> FEATURE:
<221> NAME/KEY: VARIANT
<222> LOCATION: (116)...(119)
<223> OTHER INFORMATION: Xaa = any amino acid, may be present or absent
<220> FEATURE:
<221> NAME/KEY: VARIANT
<222> LOCATION: (121)...(130)
<223> OTHER INFORMATION: Xaa = any amino acid
<220> FEATURE:
<221> NAME/KEY: VARIANT
<222> LOCATION: (131)...(133)
<223> OTHER INFORMATION: Xaa = any amino acid, may be present or absent

<400> SEQUENCE: 65

Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Cys Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Cys Xaa Xaa Xaa Xaa Xaa Xaa Xaa
        115                 120                 125

Xaa Xaa Xaa Xaa Xaa Cys
    130

<210> SEQ ID NO 66
<211> LENGTH: 135
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(93)
<223> OTHER INFORMATION: Xaa = any amino acid, may be present or absent
<220> FEATURE:
<221> NAME/KEY: VARIANT
<222> LOCATION: (95)...(116)
<223> OTHER INFORMATION: Xaa = any amino acid
<220> FEATURE:
<221> NAME/KEY: VARIANT

```
<222> LOCATION: (117)...(120)
<223> OTHER INFORMATION: Xaa = any amino acid, may be present or absent
<220> FEATURE:
<221> NAME/KEY: VARIANT
<222> LOCATION: (122)...(131)
<223> OTHER INFORMATION: Xaa = any amino acid
<220> FEATURE:
<221> NAME/KEY: VARIANT
<222> LOCATION: (132)...(134)
<223> OTHER INFORMATION: Xaa = any amino acid, may be present or absent

<400> SEQUENCE: 66

Cys Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Cys Xaa Xaa Xaa Xaa Xaa Xaa Xaa
        115                 120                 125

Xaa Xaa Xaa Xaa Xaa Xaa Cys
    130                 135

<210> SEQ ID NO 67
<211> LENGTH: 134
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(93)
<223> OTHER INFORMATION: Xaa = any amino acid, may be present or absent
<220> FEATURE:
<221> NAME/KEY: VARIANT
<222> LOCATION: (95)...(117)
<223> OTHER INFORMATION: Xaa = any amino acid
<220> FEATURE:
<221> NAME/KEY: VARIANT
<222> LOCATION: (118)...(120)
<223> OTHER INFORMATION: Xaa = any amino acid, may be present or absent
<220> FEATURE:
<221> NAME/KEY: VARIANT
<222> LOCATION: (122)...(132)
<223> OTHER INFORMATION: Xaa = any amino acid
<220> FEATURE:
<221> NAME/KEY: VARIANT
<222> LOCATION: (133)...(133)
<223> OTHER INFORMATION: Xaa = any amino acid, may be present or absent

<400> SEQUENCE: 67

Cys Xaa Xaa Xaa Xaa Xaa Xaa Xaa Xaa Xaa Xaa Xaa Xaa Xaa Xaa
 1               5                   10                  15
```

Xaa Xaa Xaa Xaa Xaa Xaa Xaa Xaa Xaa Xaa Xaa Xaa Xaa
       20                  25                  30

Xaa Xaa Xaa Xaa Xaa Xaa Xaa Xaa Xaa Xaa Xaa Xaa Xaa
       35                  40                  45

Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Cys Xaa
             85                  90                  95

Xaa Xaa Xaa Xaa Xaa Xaa Xaa Xaa Xaa Xaa Xaa Xaa Xaa
       100                 105                 110

Xaa Xaa Xaa Xaa Xaa Xaa Xaa Cys Xaa Xaa Xaa Xaa Xaa Xaa
       115                 120                 125

Xaa Xaa Xaa Xaa Xaa Cys
       130

<210> SEQ ID NO 68
<211> LENGTH: 135
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(92)
<223> OTHER INFORMATION: Xaa = any amino acid, may be present or absent
<220> FEATURE:
<221> NAME/KEY: VARIANT
<222> LOCATION: (94)...(115)
<223> OTHER INFORMATION: Xaa = any amino acid
<220> FEATURE:
<221> NAME/KEY: VARIANT
<222> LOCATION: (116)...(120)
<223> OTHER INFORMATION: Xaa = any amino acid, may be present or absent
<220> FEATURE:
<221> NAME/KEY: VARIANT
<222> LOCATION: (122)...(131)
<223> OTHER INFORMATION: Xaa = any amino acid
<220> FEATURE:
<221> NAME/KEY: VARIANT
<222> LOCATION: (132)...(134)
<223> OTHER INFORMATION: Xaa = any amino acid, may be present or absent

<400> SEQUENCE: 68

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa
       20                  25                  30

Xaa Xaa Xaa Xaa Xaa Xaa Xaa Xaa Xaa Xaa Xaa Xaa Xaa
       35                  40                  45

Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Cys Xaa Xaa
             85                  90                  95

Xaa Xaa Xaa Xaa Xaa Xaa Xaa Xaa Xaa Xaa Xaa Xaa Xaa Xaa

```
                  100             105             110
Xaa Xaa Xaa Xaa Xaa Xaa Xaa Xaa Cys Xaa Xaa Xaa Xaa Xaa Xaa
        115             120             125

Xaa Xaa Xaa Xaa Xaa Xaa Cys
        130             135
```

<210> SEQ ID NO 69
<211> LENGTH: 136
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(82)
<223> OTHER INFORMATION: Xaa = any amino acid
<220> FEATURE:
<221> NAME/KEY: VARIANT
<222> LOCATION: (83)...(93)
<223> OTHER INFORMATION: Xaa = any amino acid, may be present or absent
<220> FEATURE:
<221> NAME/KEY: VARIANT
<222> LOCATION: (95)...(117)
<223> OTHER INFORMATION: Xaa = any amino acid
<220> FEATURE:
<221> NAME/KEY: VARIANT
<222> LOCATION: (118)...(121)
<223> OTHER INFORMATION: Xaa = any amino acid, may be present or absent
<220> FEATURE:
<221> NAME/KEY: VARIANT
<222> LOCATION: (123)...(133)
<223> OTHER INFORMATION: Xaa = any amino acid
<220> FEATURE:
<221> NAME/KEY: VARIANT
<222> LOCATION: (134)...(135)
<223> OTHER INFORMATION: Xaa = any amino acid, may be present or absent

<400> SEQUENCE: 69

```
Cys Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
        20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Cys Xaa Xaa Xaa Xaa Xaa Xaa
        115                 120                 125

Xaa Xaa Xaa Xaa Xaa Xaa Xaa Cys
        130                 135
```

<210> SEQ ID NO 70
<211> LENGTH: 133
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution

```
        pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(92)
<223> OTHER INFORMATION: Xaa = any amino acid, may be present or absent
<220> FEATURE:
<221> NAME/KEY: VARIANT
<222> LOCATION: (94)...(115)
<223> OTHER INFORMATION: Xaa = any amino acid
<220> FEATURE:
<221> NAME/KEY: VARIANT
<222> LOCATION: (116)...(119)
<223> OTHER INFORMATION: Xaa = any amino acid, may be present or absent
<220> FEATURE:
<221> NAME/KEY: VARIANT
<222> LOCATION: (121)...(130)
<223> OTHER INFORMATION: Xaa = any amino acid
<220> FEATURE:
<221> NAME/KEY: VARIANT
<222> LOCATION: (131)...(132)
<223> OTHER INFORMATION: Xaa = any amino acid, may be present or absent

<400> SEQUENCE: 70

Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Cys Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Cys Xaa Xaa Xaa Xaa Xaa Xaa Xaa Xaa
        115                 120                 125

Xaa Xaa Xaa Xaa Cys
        130

<210> SEQ ID NO 71
<211> LENGTH: 133
<212> TYPE: PRT
<213> ORGANISM: Artificial Sequence
<220> FEATURE:
<223> OTHER INFORMATION: synthetic dendritic cell (DC) modulatory
      protein homologue lipocalin fold conserved Cys distribution
      pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(92)
<223> OTHER INFORMATION: Xaa = any amino acid, may be present or absent
<220> FEATURE:
<221> NAME/KEY: VARIANT
<222> LOCATION: (94)...(95)
<223> OTHER INFORMATION: Xaa = any amino acid
<220> FEATURE:
<221> NAME/KEY: VARIANT
<222> LOCATION: (97)...(115)
```

<223> OTHER INFORMATION: Xaa = any amino acid
<220> FEATURE:
<221> NAME/KEY: VARIANT
<222> LOCATION: (116)...(119)
<223> OTHER INFORMATION: Xaa = any amino acid, may be present or absent
<220> FEATURE:
<221> NAME/KEY: VARIANT
<222> LOCATION: (121)...(130)
<223> OTHER INFORMATION: Xaa = any amino acid
<220> FEATURE:
<221> NAME/KEY: VARIANT
<222> LOCATION: (131)...(132)
<223> OTHER INFORMATION: Xaa = any amino acid, may be present or absent

<400> SEQUENCE: 71

Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Cys Xaa Xaa Trp
            85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Cys Xaa Xaa Xaa Xaa Xaa Xaa Xaa Xaa
    115                 120                 125

Xaa Xaa Xaa Xaa Cys
    130

<210> SEQ ID NO 72
<211> LENGTH: 133
<212> TYPE: PRT
<213> ORGANISM: Artificial Sequence
<220> FEATURE:
<223> OTHER INFORMATION: synthetic dendritic cell (DC) modulatory
      protein homologue glycosylation site consensus sequence and
      lipocalin fold conserved Cys distribution pattern
<220> FEATURE:
<221> NAME/KEY: VARIANT
<222> LOCATION: (2)...(83)
<223> OTHER INFORMATION: Xaa = any amino acid
<220> FEATURE:
<221> NAME/KEY: VARIANT
<222> LOCATION: (84)...(92)
<223> OTHER INFORMATION: Xaa = any amino acid, may be present or absent
<220> FEATURE:
<221> NAME/KEY: VARIANT
<222> LOCATION: (94)...(95)
<223> OTHER INFORMATION: Xaa = any amino acid
<220> FEATURE:
<221> NAME/KEY: VARIANT
<222> LOCATION: (97)...(115)
<223> OTHER INFORMATION: Xaa = any amino acid
<220> FEATURE:
<221> NAME/KEY: VARIANT
<222> LOCATION: (116)...(119)
<223> OTHER INFORMATION: Xaa = any amino acid, may be present or absent
<220> FEATURE:
<221> NAME/KEY: VARIANT
<222> LOCATION: (121)...(130)
<223> OTHER INFORMATION: Xaa = any amino acid
<220> FEATURE:
<221> NAME/KEY: VARIANT
<222> LOCATION: (131)...(132)

```
<223> OTHER INFORMATION: Xaa = any amino acid, may be present or absent

<400> SEQUENCE: 72

Cys Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Cys Xaa Xaa Trp
                85                  90                  95

Xaa Xaa Xaa Xaa Xaa Xaa Xaa Xaa Xaa Xaa Xaa Xaa Xaa Xaa Xaa
            100                 105                 110

Asn Xaa Xaa Xaa Xaa Xaa Xaa Cys Xaa Xaa Xaa Xaa Xaa Xaa Xaa
        115                 120                 125

Xaa Xaa Xaa Xaa Cys
    130

<210> SEQ ID NO 73
<211> LENGTH: 6
<212> TYPE: PRT
<213> ORGANISM: Artificial Sequence
<220> FEATURE:
<223> OTHER INFORMATION: synthetic polyhistidine tag C-terminal
      extension

<400> SEQUENCE: 73

His His His His His His
 1               5
```